(12) United States Patent
Young et al.

(10) Patent No.: US 9,181,580 B2
(45) Date of Patent: Nov. 10, 2015

(54) SUPER-ENHANCERS AND METHODS OF USE THEREOF

(71) Applicant: Whitehead Institute for Biomedical Research, Cambridge, MA (US)

(72) Inventors: Richard A. Young, Boston, MA (US); Warren Whyte, Chelsea, MA (US); Denes Hnisz, Cambridge, MA (US); Jakob Loven, Belmont, MA (US); Heather Hoke, Cambridge, MA (US); David Orlando, Somerville, MA (US); Charles Y. Lin, Boston, MA (US); Tony Lee, Somerville, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/523,560

(22) Filed: Oct. 24, 2014

(65) Prior Publication Data
US 2015/0111761 A1 Apr. 23, 2015

Related U.S. Application Data

(63) Continuation of application No. 14/063,337, filed on Oct. 25, 2013, now abandoned.

(60) Provisional application No. 61/718,697, filed on Oct. 25, 2012, provisional application No. 61/799,646, filed on Mar. 15, 2013.

(51) Int. Cl.
| | |
|---|---|
| *A01N 25/00* | (2006.01) |
| *A61K 47/00* | (2006.01) |
| *C12Q 1/68* | (2006.01) |
| *C12N 15/85* | (2006.01) |

(52) U.S. Cl.
CPC .............. *C12Q 1/6804* (2013.01); *C12N 15/85* (2013.01); *C12Q 1/6869* (2013.01); *C12Q 1/6897* (2013.01); *C12N 2830/00* (2013.01)

(58) Field of Classification Search
None
See application file for complete search history.

(56) References Cited

U.S. PATENT DOCUMENTS

| | | |
|---|---|---|
| 2005/0188432 A1 | 8/2005 | Li et al. |
| 2010/0256008 A1 | 10/2010 | Ren et al. |
| 2010/0311048 A1 | 12/2010 | Sauka-spengler et al. |
| 2014/0287932 A1 | 9/2014 | Young et al. |
| 2014/0296218 A1 | 10/2014 | Young et al. |

FOREIGN PATENT DOCUMENTS

WO   WO 2014/066848    5/2014

OTHER PUBLICATIONS

Delmore et al., BET Bromodomain Inhibition as a Therapeutic Strategy to Target c-Myc, Cell, vol. 146, Issue 6, Sep. 16, 2011, pp. 904-917.*

(Continued)

*Primary Examiner* — Reza Ghafoorian
(74) *Attorney, Agent, or Firm* — Lisa M. Warren, Esq.; Morse, Barnes-Brown & Pendleton, P.C.

(57) ABSTRACT

The present invention relates in some aspects to super-enhancers and related compositions, methods, and agents that are useful for modulating expression of cell type-specific genes that are required for maintenance of cell identity (e.g., embryonic stem cell identity) or maintenance of a disease state (e.g., cancer).

30 Claims, 10 Drawing Sheets

(56) References Cited

OTHER PUBLICATIONS

Blow et al., ChIP-seq Identification of Weakly Conserved Heart Enhancers, Nat Genet. Sep. 2010 ; 42(9): 806-810. doi:10.1038/ng.650.*

Barrera et al., Genome-wide mapping and analysis of active promoters in mouse embryonic stem cells and adult organs, Genome Res. Jan. 2008; 18(1): 46-59.*

Zeng et al., In vivo dual cross-linking for identification of indirect DNA-associated proteins by chromatin immunoprecipitation, BioTechniques, vol. 41, No. 6, 2006, pp. 694, 696 and 698.*

Li et al., A global transcriptional regulatory role for c-Myc in Burkitt's lymphoma cells, PNAS, Jul. 8, 2003, vol. 100, No. 14, p. 8164-8169.*

Creyghton et al., "Histone H3K27ac separates active from poised enhancers and predicts developmental state," PNAS 107(50): 21931-21936 (2010).

Kagey et al., "Mediator and Cohesin Connect Gene Expression and Chromatin Architecture," Nature 467:430-435 (2010).

Ong et al., "Enhancer Function: New Insights into the Regulation of Tissue Specific Gene Expression," Nature Reviews Genetics 12(4):283-293 (2011).

Sakabe et al., "Transcriptional Enhancers in Development and Disease," Genome Biology 13(238): 1-12 (2012).

Chen, et al., "Enhancer Identification in Mouse Embryonic Stem Cells Using Integrative Modeling of Chromatin and Genomic Features," BMC Genomics 13(152): 1-19 (2012).

Zhang, et al., "Bromodomain-containing protein 4 (BRD4) Regulates RNA Polymerase II Serine 2 Phosphorylation in Human CD4+ T cells," JBC 287:43137-43155 (2012).

Delmore, et al., "BET Bromodomain Inhibition as a Therapeutic Strategy to Target c-Myc," Cell 146: 904-917 (2011).

Ho, et al., "An embroyonic stem cell chromatin remodeling complex, esBAF, is an essential component of the core pluripotency transcriptional network," PNAS 106(13): 5187-5191 (2009).

International Search Report for International Application PCT/US2013/066957, dated Feb. 27, 2014.

Chen, et al., Phospho-MED1-enhanced UBE2C locus looping drives castration-resistant prostate cancer growth *The Embo Journal*, 30(12): 2405-2419; 2011.

Visel, et al., "Functional autonomy of distant-acting human enhancers", *Genomics*, 93, 509-513: 2008.

Non-Final Office Action for U.S. Appl. No. 14/063,337, dated Feb. 20, 2015.

* cited by examiner

Super-enhancers are associated with key ESC genes

2A

2B

2C

2D

Super-enhancers confer high enhancer activity

3A

3B

3C

Loss of ESC super-enhancers during ESC differentiation

4A

4B

Mediator and BRD4 co-occupy promoters of active genes in multiple myeloma

6A
Brd4 occupancy at gene XBP1

6C Mediator and BRD4 occupancy correlate with one another at both enhancers and transcription start sites 6B
Brd4 occupancy at enhancers and core promoters genome-wide 6D
Mediator and BRD4 occupancy at genes correlates with RNAPII levels FIGS. 7A, 7B, 7C and 7D Super-enhancers are associated with key multiple myeloma genes 7A The sizes of enhancers occupied by Mediator show an unusual distribution

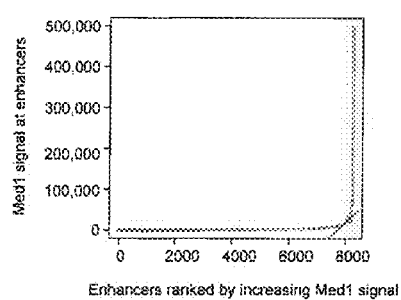

7B Super-enhancers are bound by exceptional levels of BRD4

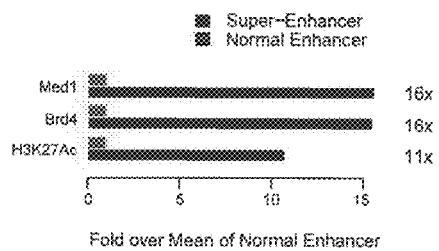

7C In MM.1S, super-enhancers are associated with highly expressed, cell type specific genes

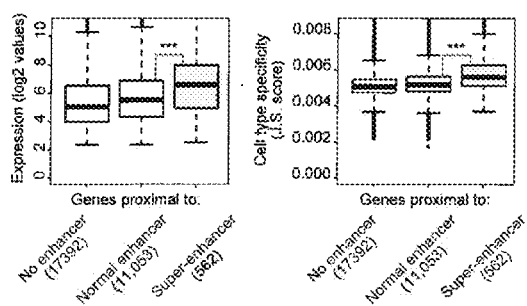

7D The *IGH-MYC* locus contains a large, 40 kB super-enhancer, occupied by high levels of BRD4 and MED1

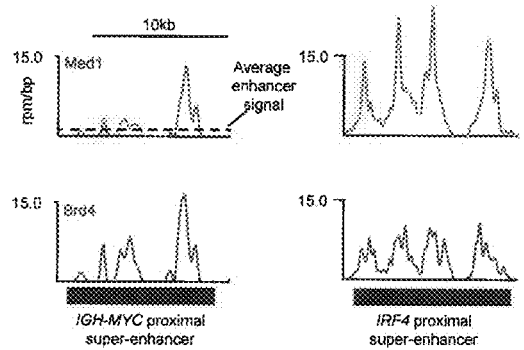

FIGS. 8A, 8B, 8C, 8D, 8E and 8F

BRD4 occupancy at super-enhancers is highly sensitive to bromodomain inhibition

8A Measuring the effects of various concentrations of JQ1 on genome-wide on BRD4 occupancy

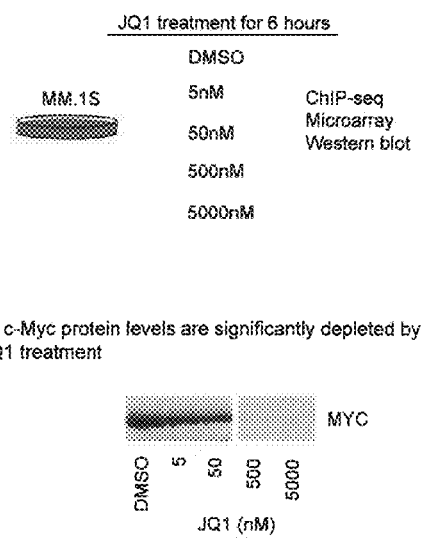

8B Short-term JQ1 treatment (6 hours) has little effect on MM1.S cell viability

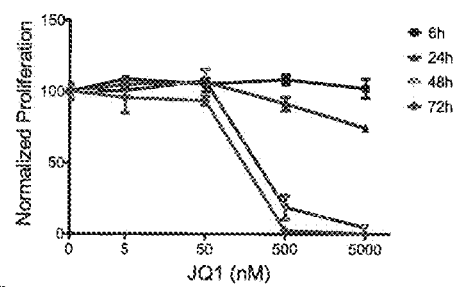

8C c-Myc protein levels are significantly depleted by JQ1 treatment

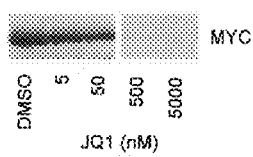

8D JQ1 does not alter BRD4 levels or ChIP-efficency

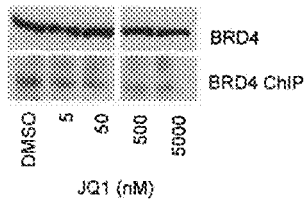

8E Super-enhancers show a greater loss of BRD4 occupancy when compared to regions with average or low amounts of BRD4

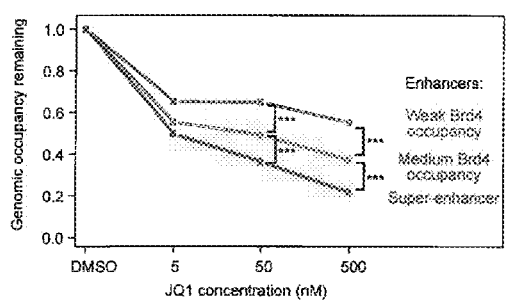

8F The IgH enhancer shows significantly greater loss of BRD4 than regions with lower BRD4 occupancy

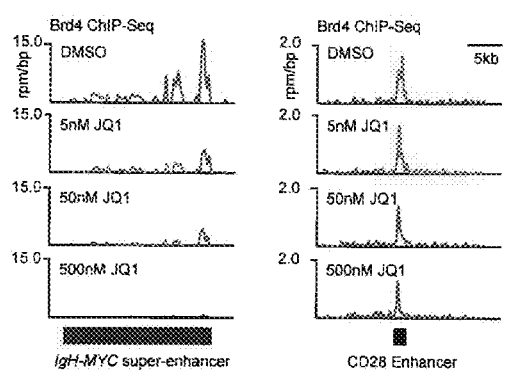

Loss of P-TEFb accompanies BRD4 inhibition

9A P-TEFb generally occupies sites bound by Mediator and BRD4 in MM1.S cells

9B Loss of BRD4 following JQ1 treatment is accompanied by loss of P-TEFb at enhancers 9C P-TEFb is disproportionally lost at super-enhancers JQ1 causes disproportionate loss of transcription at super-enhancer genes 10A
JQ1 treatment causes a global defect in transcription elongation 10B
Elongation defect at the MYC gene 10C
Genes associated with super-enhancers show a larger increase in TR

SUPER-ENHANCERS AND METHODS OF USE THEREOF

RELATED APPLICATION(S)

This application is a continuation of U.S. application Ser. No. 14/063,337, filed on Oct. 25, 2013, which claims benefit of U.S. Provisional Application Nos. 61/718,697, filed Oct. 25, 2012 and 61/799,646, filed Mar. 15, 2013. The entire teachings of the above application(s) are incorporated herein by reference.

GOVERNMENT SUPPORT

This invention was made with government support under RO1-HG002668 and RO1-CA146445 awarded by the National Institutes of Health. The government has certain rights in the invention.

BACKGROUND OF THE INVENTION

Regulatory elements (e.g., transcription factors, cis-acting enhancer elements, transcriptional coactivators and chromatin regulators) activate gene expression programs in cells ranging from embryonic stem cells (ESCs) to tumor cells. Regulatory elements are important for maintenance of cell identity (e.g., ESC identity) and of some disease states (e.g., cancer). The mechanisms underlying how regulatory elements contribute to maintenance of cell identity and of disease state are not entirely understood.

SUMMARY OF THE INVENTION

The present invention relates in some aspects to super-enhancers and related compositions, methods, and agents that are useful for modulating expression of cell type-specific genes that are required for maintenance of cell identity (e.g., embryonic stem cell identity) or maintenance of a disease state (e.g., cancer).

In some aspects, the invention provides an isolated super-enhancer, or functional fragment and/or variant thereof, comprising a genomic region of deoxyribonucleic acid (DNA) that contains at least two enhancers, wherein the genomic region is occupied when present within a cell by more, e.g., 2, 3, 4, 5, 10, or 15 fold more super-enhancer component, e.g., chromatin associated protein, e.g., a transcriptional coactivator, than the average single enhancer within the cell.

A super-enhancer component, as used herein, is a component, typically a protein, that has a higher local concentration, or exhibits a higher occupancy, at a super-enhancer, as opposed to a normal enhancer or an enhancer outside a super-enhancer, and in embodiments, contributes to increased expression of the associated gene.

In an embodiment the super-enhancer comprises all or part of a gene under its control. In an embodiment does not contain a complete associated gene.

In some embodiments the transcriptional coactivator is Mediator. In some embodiments the transcriptional coactivator is Med1.

In some embodiments the genomic region is occupied when present within a cell by more super-enhancer component, e.g., more chromatin regulator than the average single or normal enhancer within the cell.

In some embodiments the chromatin regulator is a BET bromodomain protein. In some embodiments the BET bromodomain protein is BRD4.

In some embodiments the genomic region spans between about 4 kilobases and about 40 kilobases in length.

In some embodiments the genomic region spans sufficient nucleic acid, or the super-enhancer is of sufficient size or structure, such that, when associated with a gene, the gene has substantially greater expression than in the absence of the super-enhancer.

In some embodiments the at least two enhancers are clustered together.

In some embodiments each enhancer comprises a binding site for a cognate transcription factor.

In some embodiments the cognate transcription factor comprises an embryonic stem cell master transcription factor. In some embodiments the embryonic stem cell master transcription factor is selected from the group consisting of Oct4, Sox2, Nanog, Esrrb, Utf1, Klf4, mir-290-295 microRNA gene cluster, Tbx3, Sgk1, and combinations thereof.

In some embodiments a super-enhancer component comprises an enzyme that, adds, detects or reads, or removes a functional group, e.g., a methyl or acetyl group, from a chromatin component, e.g., DNA or histones.

In some embodiments a super-enhancer component comprises an enzyme that alters, reads, or detects the structure of a chromatin component, e.g., DNA or histones, e.g., a DNA methylase or demythylase, a histone methylase or demethylase, or a histone acetylase or de-acetylase that write, read or erase histone marks, e.g., H3K4me1 or H3K27Ac.

In some embodiments a super-enhancer component comprises an enzyme, adds, detects or reads, or removes a functional group, e.g., a methyl or acetyl group, from a chromatin component, e.g., DNA or histones.

In some embodiments the super-enhancer component comprises a protein needed for development into, or maintenance of, a selected cellular state or property, e.g., a state of differentiation, development or disease, e.g., a cancerous state, or the propensity to proliferate or the propensity or the propensity to undergo apoptosis.

In some embodiments the cognate transcription factor comprises an oncogenic transcription factors. In some embodiments the oncogenic transcription factor is selected from the group consisting of c-Myc, IRF4, p53, AP-1, Bcr-Ab1, c-Fos, c-Jun and combinations thereof. In some embodiments the cognate transcription factor comprises a muscle cell transcription factor. In some embodiments the transcription factor is MyoD.

In some embodiments the cognate transcription factor comprises a B cell transcription factor. In some embodiments the transcription factor is Pu.1.

In some embodiments the genomic region is occupied when present within the cell by an order of magnitude more super-enhancer component, e.g., transcriptional coactivator than the average single enhancer within the cell. In some embodiments the order of magnitude is at least about 2-fold. In some embodiments the order of magnitude is at least about 10-fold. In some embodiments the order of magnitude is at least about 15-fold. In some embodiments the order of magnitude is at least about 16-fold.

In some aspects, the invention provides a composition comprising a super-enhancer of the present invention.

In some aspects, the invention provides a nucleic acid construct comprising a super-enhancer, or functional fragment and/or variant thereof, of the present invention. In some embodiments the nucleic acid construct includes a nucleotide sequence encoding a target gene operatively linked to the super-enhancer. In some embodiments the nucleic acid construct includes a reporter construct.

In some aspects, the invention provides a cell transfected with a nucleic acid construct comprising a super-enhancer, or functional fragment and/or variant thereof, operatively linked to a target gene wherein upon transfection of the cell with the nucleic acid construct endogenous transcriptional coactivators and chromatin regulators within the cell co-occupy the enhancers and the active transcription start sites of the target gene to stimulate high levels of expression of the target gene within the cell.

In some embodiments the cell is a mammalian cell. In some embodiments the cell is a human cell. In some embodiments the cell is an embryonic stem cell or embryonic stem cell-like cell. In some embodiments the cell is a muscle cell. In some embodiments the muscle cell is a myotube. In some embodiments the cell is a B cell. In some embodiments the B cell is a Pro-B cell.

In some aspects, the invention provides a method of increasing the level of expression of a target gene in a cell, comprising transfecting a cell under conditions suitable for expression of the target gene with a nucleic acid expression construct comprising a nucleic acid sequence encoding the target gene operatively linked to a super enhancer, or functional fragment and/or variant thereof, wherein upon transfection of the cell endogenous transcriptional coactivators and chromatin regulators within the cell co-occupy enhancers clustered within the super enhancer, or functional fragment and/or variant thereof, and active transcription start sites of the target gene to increase the level of expression of the target gene within the cell. In some embodiments the level of expression of the target gene is increased 2-fold, 3-fold, 4-fold, 5-fold, 6-fold, or more within the cell.

In some aspects the invention provides a kit for increasing the expression of a target gene in a cell, comprising: (a) a nucleic acid construct comprising an artificial super enhancer, or functional fragment and/or variant thereof, operatively linked to the target gene; (b) a population of cells suitable for expression of said target gene; and (c) a reagent for transfecting said population of cells with said nucleic acid construct.

In some aspects the invention provides a method of identifying a super enhancer, or functional fragment and/or variant thereof, in a cell, comprising: (a) identifying a genomic region of DNA within said cell characterized by a cluster of enhancers each of which bind a cognate transcription factor capable of interacting with Mediator to stimulate transcription of the target gene within said cell; (b) measuring in the identified genomic region a level of Mediator; and (c) identifying the genomic region as a super enhancer, or functional fragment and/or variant thereof, if the level of Mediator greater than the level of Mediator occupying the average single enhancer.

In some embodiments the level of Mediator identified in the genomic region is an order of magnitude more than the level of Mediator occupying the average single enhancer. In some embodiments the order of magnitude is at least 2-fold, at least 10-fold, at least 15-fold, at least 16-fold, or more.

In some embodiments the super enhancer, or functional fragment and/or variant thereof, is identified by performing chromatin immunoprecipitation high-throughput sequencing (ChIP-Seq).

In some aspects, the invention provides a method of selectively inhibiting expression of an aberrantly expressed gene comprising disrupting the function of a super-enhancer associated with the aberrantly expressed gene.

In some embodiments the gene is an oncogene. In some embodiments the oncogene is selected from the group consisting of c-MYC and IRF4.

In some embodiments disrupting the function of the super-enhancer comprises contacting said super-enhancer region with an effective amount of an agent that interferes with occupancy of the super-enhancer region by a cognate transcription factor for the gene, a transcriptional coactivator, or a chromatin regulator. In some embodiments the agent is a bromodomain inhibitor. In some embodiments the agent is a BRD4 inhibitor.

In some embodiments the agent is JQ1.

In some embodiments the agent is iBET. In some embodiments the agent interferes with a binding site on the super-enhancer for the cognate transcription factor, interferes with interaction between the cognate transcription factor and a transcriptional coactivator, inhibits the transcription coactivator, or interferes with or inhibits the chromatin regulator.

In some aspects the invention provides a method of treating a proliferative disorder in a patient in need of such treatment, said proliferative disorder characterized by an oncogene-associated super-enhancer occupied by more Mediator or BRD4 than an average single enhancer, comprising administering to the patient an effective amount of an agent that disrupts the function of the oncogene-associated super-enhancer, thereby selectively inhibiting proliferation of the oncogene in the patient.

In some embodiments the proliferative disorder is a hematological malignancy.

In some embodiments the proliferative disorder is selected from the group consisting of acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

In some embodiments the agent is a BRD4 inhibitor. In some embodiments the agent is JQ1. In some embodiments the agent is iBET.

In some aspects, the invention provides a method of treating multiple myeloma involving an IGH-MYC locus that results in aberrant expression of oncogene c-Myc, comprising administering to a patient in need of such treatment an effective amount of an agent that decreases occupancy levels of BRD4 and MED1 at a super-enhancer region associated with the IGH-MYC locus, wherein decreased occupancy levels of BRD4 and MED1 at the super-enhancer disrupt function of the super-enhancer thereby decreasing aberrant expression of oncogene c-Myc such that the multiple myeloma is treated. In some embodiments the agent is JQ1 or iBET.

In some aspects the invention provides a method of identifying an agent that disrupts a super-enhancer associated with a gene, e.g., a super-enhancer identified by a method described herein, comprising:

(a) providing a cell or cell-free system having a super-enhancer, or functional fragment and/or variant thereof, associated with a gene, e.g., a gene which is heterologous to one or both of the cell or the super-enhancer, e.g., a reporter construct;

(b) contacting the cell with a test agent, e.g., under conditions suitable for the super-enhancer, or functional fragment and/or variant thereof, to drive high levels of expression of the associated gene; and (c) measuring the level of expression of the associated gene, e.g., a reporter construct.

In an embodiment decreased expression of the associated gene in the presence of the test agent indicates that the test agent is as an agent that disrupts the super-enhancer associated with the gene.

In an embodiment the method comprises comparing the level of expression with a reference, e.g., a similar cell or cell-free system not contacted with the test agent.

In an embodiment the method comprises confirming disruption of the super-enhancer, or functional fragment and/or variant thereof, e.g., by analysis of the presence of one or more super-enhancer component.

In an embodiment the method is first performed in a cell-free system or a cell preparation, e.g., a cultured cell, and repeated in an animal.

In an embodiment the super-enhancer is associated with a gene that is expressed in a disease state cell, e.g., a cancer cell.

The method, as well as any other method described herein, can include memorializing the results.

In some aspects the invention provides a method of identifying an agent that disrupts a super-enhancer associated with a gene, comprising:

(a) providing a cell or cell-free system having a heterologous super-enhancer, or functional fragment and/or variant thereof, associated with a gene, e.g., a gene which is heterologous to one or both of the cell or the super-enhancer, e.g., a reporter construct;

(b) contacting the cell or cell-free system with a test agent, e.g., under conditions suitable for the super-enhancer, or functional fragment and/or variant thereof, to drive high levels of expression of the associated gene;

(c) and measuring the level of expression of the associated gene, e.g., a reporter construct.

In an embodiment decreased expression of the associated gene in the presence of the test agent indicates that the test agent is as an agent that disrupts the super-enhancer associated with the gene.

In an embodiment the method comprises comparing the level of expression with a reference, e.g., a similar cell or cell-free system not contacted with the test agent.

In an embodiment the method comprises confirming disruption of the super-enhancer, or functional fragment and/or variant thereof, e.g., by analysis of the presence of one or more epigenetic super-enhancer component.

In an embodiment the method is first performed in a cell-free system or a cell preparation, e.g., a cultured cell, and repeated in an animal.

In an embodiment the super-enhancer is associated with a gene that is expressed in a disease state cell, e.g., a cancer cell.

In some aspects the invention provides a method of identifying an agent that disrupts a super-enhancer associated with a gene, comprising: (a) transfecting a cell with a super-enhancer, or functional fragment and/or variant thereof, and the associated gene under conditions suitable for the super-enhancer to drive high levels of expression of the associated gene; (b) contacting the cell with a test agent; (c) and measuring the level of expression of the associated gene, wherein decreased expression of the associated gene in the presence of the test agent indicates that the test agent is as an agent that disrupts the super-enhancer associated with the gene.

In an embodiment the method comprises comparing the level of expression with a reference, e.g., a similar cell not contacted with the test agent. In an embodiment the method comprises confirming disruption of the super-enhancer, or functional fragment and/or variant thereof, e.g., by analysis of the presence of one or more super-enhancer component. In an embodiment the method is first performed in a cell-free system or a cell preparation, e.g., a cultured cell, and repeated in an animal.

In an embodiment the super-enhancer is associated with a gene that is expressed in a disease state cell, e.g., a cancer cell.

In some aspects the invention provides a method of identifying an agent that disrupts a super-enhancer comprising: (a) transfecting a cell with a super-enhancer operably linked to a reporter construct comprising a reporter gene under conditions suitable for the super-enhancer to drive high levels of expression of the reporter gene; (b) contacting the cell with a test agent; (c) and measuring the level of expression of the reporter gene, wherein decreased expression of the reporter gene in the presence of the test agent indicates that the test agent is as an agent that disrupts the super-enhancer.

In some embodiments the super-enhancer is naturally associated with a gene of interest, wherein the gene of interest is optionally a disease-associated gene, optionally an oncogene. In some embodiments expression is measured at least in part by measuring the level of a gene product encoded by the gene or by measuring activity of a gene product encoded by the gene. In some embodiments a gene product is mRNA or polypeptide encoded by the gene.

In some aspects, the invention relates to a method of identifying a super-enhancer, or a gene associated with a super-enhancer, comprising:

cross-linking, e.g., covalently cross-linking, chromatin, such that chromosomal nucleic acid is cross-linked to a super-enhancer component, e.g., a chromatin associated protein, e.g., one or more of a Mediator protein, Med1, Oct4, Sox2, Nanog, or NOS, to form a cross-linked complex;

contacting said cross-linked complex with a ligand having affinity for the super-enhancer component, e.g., an antibody or small molecule with affinity for the super-enhancer component to form a complex between the cross-linked complex and the ligand;

optionally, identifying or sequencing chromosomal nucleic acid in the complex between the cross-linked complex and the ligand, thereby identifying a super-enhancer, or a gene associated with a super-enhancer.

In an embodiment the method comprises fragmenting the chromosomal nucleic acid, e.g., after the step of forming a cross-linked complex, or after forming the complex between the cross-linked complex and the ligand.

In embodiments the method comprises identifying a gene associated with the super-enhancer.

In embodiments the method comprises classifying an enhancer as having a first or second level of occupancy, wherein said first level is higher, e.g., 2, 5, 10, or 100 times higher than the second level.

In some aspects, the invention relates to a method of identifying a super-enhancer, or a gene associated with a super-enhancer, comprising:

identifying sites on a segment of chromosome that are hypersensitive to reaction with an agent, e.g., a nuclease, e.g., a DNase, e.g., DNase I;

identifying or sequencing chromosomal nucleic acid adjacent the sites; thereby identifying a super-enhancer, or a gene associated with a super-enhancer.

In an embodiment the method comprises fragmenting the chromosomal nucleic acid, e.g., after the step of forming a cross-linked complex, or after forming the complex between the cross-linked complex and the ligand.

In embodiments the method comprises identifying a gene associated with the super-enhancer.

In an embodiment, the method comprises confirming, e.g., by sequencing, that a candidate super-enhancer site comprises a plurality of enhancers.

In embodiments the method comprises classifying an enhancer as having a first or second level of occupancy, wherein said first level is higher, e.g., 2, 5, 10, or 100 times higher than the second level.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning; A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A depicts an example enhancer upstream of the Hkt2 gene. FIG. 1B depicts an example of super-enhancer upstream of the Klf4 gene. FIG. 1C is a scatter plot showing Mediator occupancy across the ~6,400 ESC enhancers. FIG. 1D illustrates metagenes of Med1 at typical and super-enhancers in ESCs.

FIG. 2A demonstrates that super-enhancers drive highly expressed genes. FIG. 2B depicts an example of typical enhancer-associated gene (with RNA-seq). FIG. 2C depicts an example of a super-enhancer-associated gene (with RNA-seq). FIG. 2D illustrates that super-enhancers associate with the ESC master regulators Oct4, Sox2 and Nanog.

FIG. 3A shows OSN and Mediator gene tracks at enhancers near Klf4 (super-enhancer associated gene), and Egln3 (typical enhancer-associated gene), and corresponding DNA binding motifs. FIG. 3B demonstrates that super-enhancers have high enhancer activity in vitro. 3000 bp genomic fragments were cloned into a luciferase reporter plasmid. Luciferase activity was measured 24 hours post transfection, and was normalized to a co-transfected control plasmid. FIG. 3C depicts the creation of artificial super-enhancers by clustering. Single enhancers were genetically oligomerized and cloned into luciferase reporters. Luciferase activity was measured 24 hours post transfection, and was normalized to a co-transfected control plasmid.

FIG. 4A is a cartoon diagram depicting treatment of ZHBTc4 ESCs with doxycycline leading to loss of Oct4 proteins, loss of ESC state, and formation of early trophectoderm cells. FIG. 4B illustrates that Mediator is rapidly lost at key ESC super-enhancers compared to median enhancers. Bar graphs of mean normalized Med1 density before and during ESC differentiation at selected ESC super-enhancers and median enhancers. The associated genes were identified based on their proximity to the enhancers. Asterisks denote enhancers displaying at least two-fold reduction in Mediator.

FIG. 5A demonstrates that Pro-B enhancers are associated with the gene Rag1. ChIP-Seq binding profiles (normalized reads/million) for the pro-B transcription factor (Pu.1), and the Mediator coactivator (Med1) at the Rag1 locus in pro-B cells, with the y-axis floor set to 1. Gene model, and previously described enhancer regions are depicted below the binding profiles. FIG. 5B demonstrates that pro-B super-enhancers are associated with the key pro-B gene Inpp5d. ChIP-Seq binding profiles (normalized reads/million) for the pro-B transcription factor (Pu.1), and the Mediator coactivator (Med1) at the Inpp5d locus in pro-B cells, with the y-axis floor set to 1. Gene model, and previously described enhancer regions are depicted below the binding profiles. FIG. 5C is a scatter plot of Mediator occupancy across the ~13000 pro-B enhancers. FIG. 5D demonstrates that master transcription factors (Oct4 for ESCs; Pu.1 for pro-B cells) and Mediator occupy approximately super-enhancer regions that are specific for ESCs and pro-B cells. Density maps of the Mediator coactivator (Med1) in ESCs and pro-B cells. Color scale reflects ChIP-Seq signal in reads per million. FIG. 5E demonstrates that super-enhancer associated genes display highly cell-type specific patterns of expression. Venn diagram of ESC super-enhancer-associated genes and pro-B super-enhancer-associated genes.

FIG. 6A depicts gene tracks of BRD4, MED1, H3K27ac, and H3K4me3 binding at the XBP1 gene in MM.1S multiple myeloma. FIG. 6B is a meta-gene representation of global BRD4, MED1, H3K27ac, and H3K4me3 occupancy at enhancers and promoters. The top 5,000 active enhancers are defined by MED1 occupancy, and TSS includes all transcriptionally active promoters defined by H3K4me3 and POL2. FIG. 6C demonstrates that Mediator and BRD4 occupancy correlate with one another at both enhancers and transcription start sites. Scatter plots depicting MED1 and BRD4 aggregate signal +/− 5kb from enhancers and promoters (as defined in 1B). FIG. 6D demonstrates that BRD4 occupancy at genes correlates with RNAPII levels.

FIGS. 7A, 7B, 7C and 7D demonstrate that super-enhancers are associated with key multiple myeloma genes. FIG. 7A demonstrates that the sizes of enhancers occupied by Mediator show an unusual distribution. FIG. 7B depicts occupancy of MED1, BRD4, and H3K27ac at super-enhancers compared to normal enhancers. FIG. 7C demonstrates that super-enhancers are associated with highly expressed, cell type specific genes. FIG. 7D demonstrates that the IgH-MYC locus and IRF4 contain a large super-enhancers occupied by high levels of BRD4 and MED1.

FIGS. 8A, 8B, 8C, 8D, 8E and 8F demonstrate that BRD4 occupancy at super-enhancers is highly sensitive to bromodomain inhibition. FIG. 8A depicts measuring the effects of various concentrations of JQ1 on genome-wide on BRD4 occupancy. Schematic depicting the experimental procedure. FIG. 8B demonstrates that short-term JQ1 treatment (6 hours) has little effect on MM.1 S cell viability. JQ1 sensitivity of MM.1S cells by measurement of ATP levels (CellTiterGlo) after 6 hours of treatment. FIG. 8C illustrates that c-Myc protein levels are significantly depleted by JQ1 treatment. Western blot of relative c-MYC levels after 6 hours of JQ1 or DMSO treatment. FIG. 8D demonstrates that JQ1 does not alter BRD4 levels or ChIP-efficency. Western blot of relative BRD4 levels after 6 hours of JQ1 or DMSO treatment. ChIP-Western blot of the relative levels of immunoprecipitated BRD4 after 6 hours of JQ1 or DMSO treatment. FIG. 8E demonstrates that super-enhancers show a greater loss of BRD4 occupancy when compared to regions with average or low amounts of BRD4. FIG. 8F demonstrates that the IgH enhancer shows significantly greater loss of BRD4 than regions with lower BRD4 occupancy. Gene tracks of BRD4 at the IGH super enhancer and the average, CD28 enhancer after 6 hours of DMSO or JQ1 treatment.

FIG. 9A demonstrates that P-TEFb generally occupies enhancers bound by Mediator and BRD4 in MM1.S cells. FIG. 9B demonstrates that the loss of BRD4 following JQ1 treatment is accompanied by loss of P-TEFb at enhancers. FIG. 9C demonstrates that P-TEFb is disproportionally lost at super-enhancers.

FIG. 10A demonstrates that JQ1 leads to a global defect in transcription elongation. FIG. 10B demonstrates that genes associated with super-enhancers show a dramatic defect in elongation. Gene tracks of RNA PolII occupancy at the MYC gene after 6 hour treatment with JQ1. FIG. 10C demonstrates that genes associated with super enhancers show a larger increase in travelling ratio in response to JQ1 compared to genes associated with normal enhancers.

DETAILED DESCRIPTION OF THE INVENTION

Figures 1A, 1B, 1C, 1D:
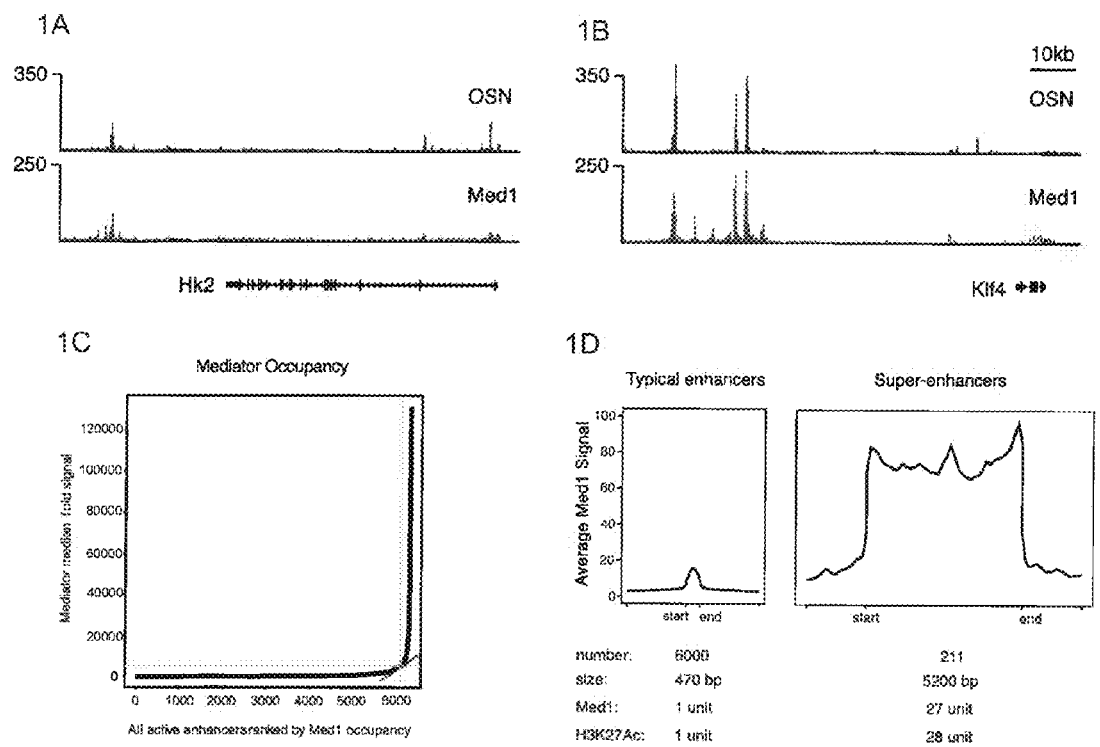
FIGS. 1A, 1B, 1C and 1D demonstrate that Oct4/Sox2/Nanog define enhancers in ES cells.

The present invention relates in some aspects to super-enhancers and related compositions, methods, and agents that are useful for modulating expression of cell type-specific genes that are required for maintenance of cell identity (e.g., embryonic stem cell identity) or maintenance of a disease state (e.g., cancer). In some aspects, the present invention relates to methods of identifying super-enhancers, super-enhancer-associated genes, and disease-related genes in cells, tissues, organs and individuals, and kits comprising reagents for performing those methods.

During the course of work described herein, more than 200 genomic regions that contained tightly spaced clusters of enhancers spanning extraordinarily large domains were discovered. These "super-enhancers" are occupied by more transcriptional coactivator (e.g., Mediator) than the average or median enhancers, exhibit greater activity than average enhancers, and are sufficient to drive high expression of key, cell type-specific genes required to maintain cell identity or disease state.

Accordingly, in some aspects, the present invention relates to an isolated super-enhancer, or functional fragment and/or variant thereof, comprising a genomic region of DNA that contains at least two enhancers, wherein the genomic region is occupied when present within a cell by more super-enhancer component, e.g., transcriptional coactivator than the average single enhancer within the cell. As used herein, "enhancer" refers to a short region of DNA to which proteins (e.g., transcription factors) bind to enhance transcription of a gene. As used herein, "transcriptional coactivator" refers to a protein or complex of proteins that interacts with transcription factors to stimulate transcription of a gene. In some embodiments, the transcriptional coactivator is Mediator. In some embodiments, the transcriptional coactivator is Med1 (Gene ID: 5469). In some embodiments, the transcriptional coactivator is a Mediator component. As used herein, "Mediator component" comprises or consists of a polypeptide whose amino acid sequence is identical to the amino acid sequence of a naturally occurring Mediator complex polypeptide. The naturally occurring Mediator complex polypeptide can be, e.g., any of the approximately 30 polypeptides found in a Mediator complex that occurs in a cell or is purified from a cell (see, e.g., Conaway et al., 2005; Kornberg, 2005; Malik and Roeder, 2005). In some embodiments a naturally occurring Mediator component is any of Med1-Med31 or any naturally occurring Mediator polypeptide known in the art. For example, a naturally occurring Mediator complex polypeptide can be Med6, Med7, Med10, Med12, Med14, Med15, Med17, Med21, Med24, Med27, Med28 or Med30. In some embodiments a Mediator polypeptide is a subunit found in a Med11, Med17, Med20, Med22, Med8, Med18, Med19, Med6, Med30, Med21, Med4, Med7, Med31, Med10, Med1, Med27, Med26, Med14, Med15 complex. In some embodiments a Mediator polypeptide is a subunit found in a Med12/Med13/CDK8/cyclin complex. Mediator is described in further detail in PCT International Application No. WO 2011/100374, the teachings of which are incorporated herein by reference in their entirety. In some embodiments, Mediator occupation of an enhancer, e.g., a superenhancer, may be detected by detecting one or more Mediator components. It is to be understood that a Mediator inhibitor may inhibit one or more Mediator components or inhibit interaction(s) between them or inhibit interaction with a transcription factor.

In some embodiments a "naturally occurring polypeptide" is a polypeptide that naturally occurs in a eukaryote, e.g., a vertebrate, e.g., a mammal. In some embodiments the mammal is a human. In some embodiments the vertebrate is a non-human vertebrate, e.g., a non-human mammal, e.g., rodent, e.g., a mouse, rat, or rabbit. In some embodiments the vertebrate is a fish, e.g., a zebrafish. In some embodiments the eukaryote is a fungus, e.g., a yeast. In some embodiments the eukaryote is an invertebrate, e.g., an insect, e.g., a *Drosophila*, or a nematode, e.g., C. elegans. Any eukaryotic species is encompassed in various embodiments of the invention. Similarly a cell or subject can be of any eukaryotic species in various embodiments of the invention. In some embodiments, the sequence of the naturally occurring polypeptide is the sequence most commonly found in the members of a particular species of interest. One of skill in the art can readily obtain sequences of naturally occurring polypeptides, e.g., from publicly available databases such as those available at the National Center for Biotechnology Information (NCBI) website (e.g., GenBank, OMIM, Gene).

In some embodiments, the transcriptional coactivator is a component of Mediator. In some embodiments, the Mediator component comprises a Med1 or a Med12 polypeptide. In some embodiments, the at least one Mediator component comprises Med6, Med7, Med10, Med12, Med14, Med15, Med17, Med21, Med24, Med27, Med28 and Med30 polypeptides.

In some embodiments, the genomic region of the super-enhancer is occupied when present within a cell by more chromatin regulator than the average single enhancer within the cell. As used herein, "chromatin regulator" refers to a protein or complex of proteins that is involved in regulating gene expression by interacting with transcription factors, transcriptional coactivators, and/or acetylated histone residues in a way that modulates expression of a super-enhancer-associated gene. In some instances, the chromatin regulator possesses histone acetyltransferase (HAT) activity. HATs are responsible for acetylating lysine residues on histone tails of nucleosomes, thereby relaxing the chromatin and increasing access to DNA. In some embodiments, the chromatin regulator is a BET bromodomain protein. In some embodiments, the BET bromodomain protein is BRD4 (Gene ID: 23476).

Generally, super-enhancers formed by the at least two enhancers in the genomic region of DNA are of greater length than the average single enhancer. In some embodiments, the length of the genomic region that forms the super-enhancer is at least an order of magnitude greater than the average single enhancer. In some embodiments, the genomic region spans between about 4 kilobases and about 40 kilobases in length. It should be appreciated, however, that super-enhancers may comprise genomic regions less than 4 kilobases or greater than 40 kilobases in length, as long as the genomic region contains clusters of enhancers that can be occupied when present within a cell by extremely high levels of a transcriptional coactivator (e.g., Mediator).

Table 1 (relating to nucleotide sequences of super-enhancers found within embryonic stem cells) and Table 2 (relating to nucleotide sequences of super-enhancers found within multiple myeloma cells); Table 3 (relating to nucleotide sequences of super-enhancers found in glioblastoma cells); and Table 4 (relating to nucleotide sequences of super-enhancers found in SCLC cells) disclose information that can be relied upon by one of skill in the art to obtain the specific nucleotide sequences for exemplary super-enhancers of the invention. For example, using the chromosomal number, and start and stop positions, as well as the sense orientation (e.g. +) of the sequence provided in Tables 1 and 2, one of skill in the art would be able to utilize a publicly available database (e.g., USCS Genome Browser, available at genome.ucsc.edu/) to obtain the nucleotide sequences of the specified super-enhancers. For the embryonic stem cell super-enhancer nucleotide sequences specified in Table 1, the mm9 genome build was used. This corresponds to NCBI build 37. For the multiple myeloma cell super-enhancer nucleotide sequences specified in Table 2, the hg 18 genome build was used. This corresponds to NCBI build 36. Tables 3 and 4 are also based on the hg 18 genome build. In some embodiments, the invention comprises a super-enhancer, or functional fragment and/or variant thereof, having a nucleotide sequence specified in Tables 1, 2, 3 or 4.

The at least two enhancers which form the super-enhancers, or functional fragment and/or variant thereof, are clustered together.

It should be appreciated that the each of the at least two enhancers can be the same type of enhancer or the at least two enhancers can be different types of enhancers. Each enhancer of the at least two enhancers comprises a binding site for a cognate transcription factor that interacts with the transcriptional coactivator to stimulate transcription of the gene associated with the super-enhancer. In some embodiments, the cognate transcription factor comprises an embryonic stem cell master transcription factor. Examples of suitable embryonic stem cell master transcription factors include, but are not limited to Oct4, Sox2, Nanog, Esrrb, Utf1, Klf4, mir-290-295 gene cluster, Tbx3, Sgk1, and combinations thereof. In some embodiments, the cognate transcription factor comprises an oncogenic transcription factor. Examples of suitable oncogenic transcription factors include, but are not limited to c-Myc, IRF4, p53, AP-1, Bcr-Abl, c-Fos, c-Jun and combinations thereof. In some embodiments, the cognate transcription factor comprises a muscle cell transcription factor, for example, transcription factor MyoD. In some embodiments, the cognate transcription factor comprises a B cell transcription factor, for example Pu.1.

As noted above, the genomic region of the super-enhancers are occupied when present within a cell by more transcriptional coactivator (e.g., Mediator) and/or more chromatin regulator (e.g., BRD4) than the average single enhancer within the cell. In some embodiments, the genomic region of a super-enhancers is occupied when present within the cell by an order of magnitude more transcriptional coactivator or chromatin regulator than the average single enhancer in the cell. As used herein, "order of magnitude" refers to the relative fold difference in a feature or classification of one object as compared to a feature or classification of another object (e.g., a level or an amount of transcriptional coactivator occupying a super-enhancer associated with a gene as compared to the level or the amount of transcriptional coactivator occupying the average or median enhancer associated with the gene). In some embodiments, the order of magnitude is at least 1-fold, 2-fold, 3-fold, 4-fold, 5-fold, 6-fold, 7-fold, 8-fold, 9-fold, 10-fold or more. In some embodiments, the order of magnitude is at least 2-fold (i.e., there is a 2-fold greater amount of transcriptional coactivator occupying the super-enhancer associated with a gene than the amount of transcriptional coactivator occupying the average enhancer in the gene). In some embodiments, the order of magnitude is at least 10-fold. In some embodiments, the order of magnitude is at least 15-fold. In some embodiments, the order of magnitude is at least 16-fold.

Work described herein suggests that super-enhancers are a common feature of mammalian cells. Accordingly, the present invention contemplates that super-enhancers can be isolated from any mammalian cell type. Such isolation can be achieved by routine methods well known to those skilled in the art.

In some embodiments, super-enhancers of the present invention can be used drive high levels of expression of cell type specific genes. A cell type specific gene is typically expressed selectively in one or a small number of cells types relative to expression in many or most other cell types. One of skill in the art will be aware of numerous genes that are considered cell type specific. A cell type specific gene need not be expressed only in a single cell type but may be expressed in one or several, e.g., up to about 5, or about 10 different cell types out of the approximately 200 commonly recognized (e.g., in standard histology textbooks) and/or most abundant cell types in an adult vertebrate, e.g., mammal, e.g., human. In some embodiments, a cell type specific gene is one whose expression level can be used to distinguish a cell of one of the following types from cells of the other cell types: adipocyte (e.g., white fat cell or brown fat cell), cardiac myocyte, chondrocyte, endothelial cell, exocrine gland cell, fibroblast, glial cell, hepatocyte, keratinocyte, macrophage, monocyte, melanocyte, neuron, neutrophil, osteoblast, osteoclast, pancreatic islet cell (e.g., a beta cell), skeletal myocyte, smooth muscle cell, B cell, plasma cell, T cell (e.g., regulatory, cytotoxic, helper), or dendritic cell. In some embodiments a cell type specific gene is lineage specific, e.g., it is specific to a particular lineage (e.g., hematopoietic, neural, muscle, etc.) In some embodiments, a cell-type specific gene is a gene that is more highly expressed in a given cell type than in most (e.g., at least 80%, at least 90%) or all other cell types. Thus specificity may relate to level of expression, e.g., a gene that is widely expressed at low levels but is highly expressed in certain cell types could be considered cell type specific to those cell types in which it is highly expressed. It will be understood that expression can be normalized based on total mRNA expression (optionally including miRNA transcripts, long non-coding RNA transcripts, and/or other RNA transcripts) and/or based on expression of a housekeeping gene in a cell. In some embodiments, a gene is considered cell type specific for a particular cell type if it is expressed at levels at least 2, 5, or at least 10-fold greater in that cell than it is, on average, in at least 25%, at least 50%, at least 75%, at least 90% or more of the cell types of an adult of that species, or in a representative set of cell types. One of skill in the art will be aware of databases containing expression data for various cell types, which may be used to select cell type specific genes. In some embodiments a cell type specific gene is a transcription factor.

In some aspects, the present invention relates to a composition comprising a super-enhancer of the present invention or a functional variant thereof. Such compositions may be useful for stimulating the expression of a gene or genes in a specific cell type, for example, to stimulate the expression of embryonic stem cell master transcription factors to maintain the cell in an embryonic stem cell-like state. In some instances, such compositions may be useful for stimulating the expression of a gene or genes in a specific cell type to change the identity of a specific cell-type, for example, by introducing a super-enhancer associated with a differentiated state to change the identity of an embryonic stem cell to a more differentiated state. In some embodiments, the super-enhancer can be used to stimulate expression of a target gene that is to be transfected into a cell for in vitro expression of that target gene. In some embodiments, the super-enhancer can be used to simulate a disease like state. By way of example, and not of limitation, an super-enhancer can be constructed using enhancers of an oncogene and transfection of the oncogene with the artificial enhancer can be useful to simulate the disease associated with the oncogene. Another exemplary use of a super-enhancer of the present invention is to identify genes that are prone to lead to disease upon aberrant expression. Such super-enhancers may be used in cells, tissues, organs, and whole organisms to artificially increase the expression of certain genes and examine the biological effects that the increased expression of the gene has on the cell, the tissue, organ, or animal.

It should be appreciated that any enhancer associated with the target gene can be cloned and used to form the super-enhancers. In some embodiments, the super-enhancer is engineered to mimic a super-enhancer identified in vivo, such as a super-enhancer that is responsible for maintaining embryonic stem cell identity, i.e., a super-enhancer comprising a plurality of Oct4, Sox2, and Nanog binding motifs oligomerized to form a concatemer.

In some aspects, the present invention relates to a nucleic acid construct comprising a super-enhancer, or functional fragment thereof, of the present invention. Methods of forming nucleic acid constructs are known to those skilled in the art. It should be understood that the nucleic acid constructs of the present invention are artificial or engineered constructs not to be confused with native genomic sequences. Such nucleic acid constructs can be used, for example, to increase the expression of a gene or genes associated with or regulated by the super-enhancer in the nucleic acid construct. In some instances, a nucleic acid construct comprising the super-enhancer can be introduced into a target cell and the super-enhancer can interact with endogenous cellular components to drive expression of an endogenous gene within the cell. In some embodiments, the nucleic acid construct includes a nucleotide sequence encoding a target gene operatively linked to the super-enhancer. In such instances, the nucleic acid can be transfected into a cell and interact with endogenous cellular components to drive expression of the exogenous target gene associated with the super-enhancer. In other embodiments, the nucleic acid construct can include a nucleic acid sequence encoding a transcriptional coactivator or chromatin regulator that can be expressed within the cell to produce transcriptional coactivator or chromatin regulator that can occupy the genomic region of the super-enhancer and increase expression of the gene associated with the super-enhancer in the cell. In some embodiments, the nucleic acid can include a reporter.

In some embodiments a reporter comprises a nucleic acid sequence that encodes a detectable marker, e.g., a fluorescent protein such as green fluorescent protein (GFP), blue, sapphire, yellow, red, orange, and cyan fluorescent proteins and fluorescent variants such as enhanced GFP (eGFP), mFruits such as mCherry, mTomato, mStrawberry; R-Phycoerythrin, etc. Enzymes useful as reporters include, e.g., enzymes that act on a substrate to produce a colored, fluorescent, or luminescent substance. Examples include luciferases, beta-galactosidase, horseradish peroxidase, and alkaline phosphatase. In some embodiments, alteration (e.g., reduction) in the level of a reporter may be used to identify a compound that modulates (e.g., inhibits) activity of a super-enhancer.

In some aspects, the present invention relates to a kit for increasing the expression of a gene, the kit including one or more or all of: (a) a population of cells; (b) reagents suitable for culturing said population of cells; (c) a nucleic acid construct comprising a super-enhancer enhancer or functional fragment and/or variant thereof, and a gene associated with the super-enhancer enhancer or functional fragment and/or variant thereof, that is capable of being expressed within said population of cells; and optionally (d) transcriptional coactivator or chromatin regulator e.g., excess levels of transcriptional coactivator or chromatin regulator that, e.g., can be introduced into said population of cells such that an order of magnitude more transcriptional coactivator or chromatin regulator occupies enhancers clustered within the super-enhancer and increases the expression of the gene within the cells.

In some aspects, the present invention relates to a cell, or cell-free system, into which a super-enhancer is introduced, for example by transfection of a nucleic acid construct comprising the super-enhancer, wherein upon introduction of super-enhancer into the cell, or cell-free system, endogenous transcriptional coactivators and chromatin regulators within the cell co-occupy the enhancer clusters of the super-enhancer and the active transcription start sites of the target gene to stimulate expression of the target gene within the cell. It should be appreciated that the super enhancer, or functional fragment and/or variant thereof, may be associated with and regulate an endogenous gene within the transfected cell. In such instances, the gene regulated by the super-enhancer, or functional fragment and/or variant thereof, need not be introduced into the cell with the super-enhancer, for example a nucleic acid construct need not include a target gene for expression within the transfected cell. In other instances, such as when an exogenous gene is desired to be introduced within the transfected cell, or cell-free system, the exogenous gene can be introduced into the cell with the super-enhancer, or functional fragment and/or variant thereof, or functional fragment and/or variant thereof. It should be appreciated that the exogenous gene and the super-enhancer or functional fragment and/or variant thereof, can be introduced into the cell by any method and in any form (e.g., protein or nucleic acid). The exogenous gene and the super-enhancer, or functional fragment and/or variant thereof, can be introduced into the cell, or cell-free system, together or separately, for example a nucleic acid construct comprising the super enhancer, or functional fragment and/or variant thereof, may be further engineered to include an exogenous gene operatively linked to the super-enhancer, or functional fragment and/or variant thereof, and which is also capable of being expressed within the transfected cell, or cell-free system. In some embodiments, exogenous transcriptional coactivators and/or chromatin regulators can be introduced into the transfected cell, or cell-free system to ensure that the enhancer clusters of the super-enhancer and the active transcription start sites are co-occupied within the transfected cell, or cell-free system by more transcriptional coactivator and/or the chromatin regulator and thereby drive high levels of expression of either an exogenous or endogenous gene in the transfected cell, or cell-free system.

The super-enhancer and/or a nucleic acid construct comprising the super-enhancer, or functional fragment and/or variant thereof, can be transfected into any cell suitable for expressing the gene associated with the super-enhancer. In some embodiments, the cell is a mammalian cell. In some embodiments, the cell is a human cell. In some embodiments, the cell is an embryonic stem cell or embryonic stem cell-like cell. In some embodiments, the cell is a muscle cell. In some embodiments, the muscle cell is a myotube. In some embodiments, the cell is a B cell. In some embodiments, the B cell is a Pro-B cell.

In some aspects, the present invention relates to a functional variant of a super-enhancer. A variant may be shorter or longer than the original super-enhancer. The term "variant" encompasses "fragments" or "functional fragments" of super-enhancers, or functional sequence variants, of super-enhancers. A "fragment" is a continuous portion of a polypeptide or polynucleotide that is shorter than the original polypeptide or polynucleotide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. A functional fragment of a super-enhancer can have one or more of the following properties:

a) when associated with a gene, e.g., a gene with which it is normally associated, it provides at least 10, 20, 30, 40, 50, 60, 70, 80, or 90% of the level of expression as is seen with the intact super-enhancer;

b) when associated with a gene, e.g., a gene with which it is normally associated, it provides at least 10, 20, 30, 40, 50, 60, 70, 80, or 90% of the level of binding of an super-enhancer component;

c) when associated with a gene, e.g., a gene with which it is normally associated, it provides at least 10, 20, 30, 40, 50, 60, 70, 80, or 90% of the level of binding of a mediator protein, e.g., Med1;

d) it comprises at least 10, 20, 30, 40, 5, 60, 70, 80 or 90% of the enhancers of the super-enhancer of which it is a functional fragment; or e) it is at least 10, 20, 30, 40, 5, 60, 70, 80 or 90% as long as the super-enhancer of which it is a functional fragment.

The term variant also encompasses "sequence variants," e.g., "functional sequence variants," of a super enhancer or fragment or functional fragment of a super-enhancer. A functional sequence variant of a super-enhancer can have one or more of the following properties:

a) it comprises sufficient nucleotide sequence homology or identity with a reference super-enhancer, e.g., the super-enhancer from which it is derived, that when associated with a gene, e.g., a gene with which the reference super-enhancer is normally associated, it provides at least 10, 20, 30, 40, 50, 60, 70, 80, or 90% of the level of expression as is seen with the reference super-enhancer;

b) when associated with a gene, e.g., a gene with which the reference super-enhancer, e.g., the super-enhancer from which it is derived, is normally associated, it provides at least 10, 20, 30, 40, 50, 60, 70, 80, or 90% of the level of binding of an super-enhancer component as is seen with the reference super-enhancer;

c) when associated with a gene, e.g., a gene with which the reference super-enhancer, e.g., the super-enhancer from which it is derived, is normally associated, it provides at least 10, 20, 30, 40, 50, 60, 70, 80, or 90% of the level of binding of a mediator protein, e.g., Med1 as is seen with the reference super-enhancer;

d) it comprises at least 10, 20, 30, 40, 5, 60, 70, 80 or 90% of the number of functional enhancers as is seen with the reference super-enhancer, e.g., the super-enhancer from which it is derived;

e) it comprises at least 40, 50, 60, 70, 80, 90, 95, 97, or 99% sequence homology or identity with a reference super-enhancer, e.g., the super-enhancer from which it is derived;

f) it comprises at least 40, 50, 60, 70, 80, 90, 95, 97, or 99% sequence homology or identity, across its encompassed enhancer elements, with a reference super-enhancer, e.g., the super-enhancer from which it is derived; or f) it comprises a first level or sequence or homology or identity across its encompassed enhancer elements and/or associated protein encoding element, and a second level of homology across untranslated and/or untranscribed regions between its encompassed enhancers, with a reference super-enhancer, e.g., the super-enhancer from which it is derived, wherein the first and second levels are independently selected from at least 40, 50, 60, 70, 80, 90, 95, 97, or 99% sequence homology or identity, and, e.g., the first level is higher than the second level, e.g., the first level is at least 80, 90, 95, 97, or 99% and the second level is at least 40, 50, or 60%.

In some embodiments a variant polypeptide comprises or consists of at least one domain of an original polypeptide. In some embodiments a variant polynucleotide hybridizes to an original polynucleotide under stringent conditions, e.g., high stringency conditions, for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the original polypeptide over at least 20%, 30%, 40%, 50%, 60%, 70%, 80%, 90%, 95%, 96%, 97%, 98%, 99%, or 100% of the original polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the original polypeptide over at least 20%, 30%, 40%, 50%, 60%, 70%, 80%, 90%, 95%, 96%, 97%, 98%, 99%, or 100% of the original polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to an original sequence, wherein N is any integer between 1 and 10 or between 1 and 20 or any integer up to 1%, 2%, 5%, or 10% of the number of amino acids in the original polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
| | | I L V |
| | Polar - uncharged | C S T M |
| | | N Q |
| | Polar - charged | D E |
| | | K R |
| Aromatic | | H F W Y |

In some aspects, the present invention relates to a method of increasing the level of expression of a target gene in a cell, the method including transfecting a cell under conditions suitable for expression of the target gene with a nucleic acid expression construct comprising a nucleic acid sequence encoding the target gene operatively linked to a super-enhancer, wherein upon transfection of the cell endogenous transcriptional coactivators and chromatin regulators within the cell co-occupy enhancers clustered within the super-enhancer and active transcription start sites of the target gene to increase the level of expression of the target gene within the cell. Those skilled in the art will appreciate that the step of transfecting can be achieved in a variety of ways according to well-known and routine methods, for example, by using a transfection reagent, such as a plasmid or a lipid based transfection reagent. In some instances, it may be desirable to introduce into the cell exogenous transcriptional coactivators and chromatin regulators to ensure that enhancers clustered within the super-enhancer and the activate transcription start sites of the target gene are co-occupied by an order of magnitude more of the transcriptional coactivators and chromatin regulators than the average enhancer of the target gene. The exogenous transcriptional coactivators and chromatin regulators can be introduced into the target cell in the form of nucleic acids that can be transfected into the cell for expression within the cell or in the form of proteins, for example, by microinjecting the proteins into the cell. Other ways of introducing nucleic acids and proteins into a cell are apparent to those skilled in the art. Upon transfection of the cell with the nucleic acid construct containing the super enhancer, or functional fragment and/or variant thereof, it is expected that the level of expression of the target gene will increase significantly, for example, the level of expression of the target gene is increased 2-fold, 3-fold, 4-fold, 5-fold, 6-fold or more within the cell.

In some aspects, the present invention relates to a kit for increasing the expression of a target gene in a cell, comprising one or more or all of: (a) a super-enhancer operatively linked to a target gene; (b) a population of cells suitable for expression of said target gene; and (c) a reagent for introducing the super-enhancer and the target gene into said population of cells. In some embodiments, the reagent comprises a transfection reagent, e.g., a plasmid.

In some aspects, the present invention relates to a kit for increasing the expression of a target gene in a cell, comprising one or more or all of: (a) a nucleic acid construct comprising an artificial super-enhancer operatively linked to the target gene; (b) a population of cells suitable for expression of said target gene; and (c) a reagent for transfecting said population of cells with said nucleic acid construct.

In some aspects, the invention relates to a nucleic acid vector comprising a super-enhancer, or functional fragment and/or variant thereof, and a site, e.g., a restriction enzyme site, disposed such that insertion of a structural gene at the site places the structural gene under the control of the super-enhancer, or functional fragment and/or variant thereof. In embodiments the vector further comprise one or more of a first selectable marker, a second selectable marker, and an origin of replication.

In some aspects, the invention relates to a nucleic acid vector comprising a super-enhancer or functional fragment and/or variant thereof, functionally linked to a heterologous reporter gene, e.g., a fluorescent protein e.g., GFP, or an enzyme, e.g., horse radish peroxidase. In embodiments the vector further comprise one or more of a first selectable marker, a second selectable marker, and an origin of replication. In some aspects, the invention relates to a kit comprising one or both of:

a first nucleic acid comprising a reference super-enhancer or functional fragment and/or variant thereof, optionally, coupled to a reporter gene; and a second nuclide acid comprising a site for insertion of an SE, or functional fragment and/or variant thereof, optionally, coupled to a reporter gene.

In some aspects, the invention relates to a kit comprising one or both of:

a nucleic acid vector comprising a super-enhancer, or functional fragment and/or variant thereof, functional linked to a heterologous reporter gene, e.g., a fluorescent protein e.g., GFP, or an enzyme, e.g., horse radish peroxidase. In embodiments the vector further comprise one or more of a first selectable marker, a second selectable marker, and an origin of replication; and a nucleic acid vector comprising an site, e.g., an restriction enzyme site, and a reporter gene, e.g., a fluorescent protein e.g., GFP, or an enzyme, e.g., horse radish peroxidase, wherein said site is disposed such that insertion into the site of a super-enhancer, or functional fragment and/or variant thereof, will place the reporter gene under the control of the super-enhancer, or functional fragment and/or variant thereof. In embodiments the vector further comprise one or more of a first selectable marker, a second selectable marker, and an origin of replication.

In some aspects, the present invention relates to a method of identifying a super-enhancer in a cell, or cell-free system, comprising: (a) identifying a genomic region of a target gene within said cell, or cell-free system characterized by clusters of enhancers for binding cognate transcription factors capable of interacting with Mediator to stimulate transcription of the target gene within said cell, or cell-free system; (b) measuring in the identified genomic region a level of Mediator occupying said enhancers; and (c) identifying the genomic region as a super-enhancer if the level of Mediator occupying the clusters of enhancers is an order of magnitude more than the level of Mediator occupying the average enhancer of the target gene.

In other aspects, the present invention relates to a method of identifying a super-enhancer associated with a target gene, comprising: (a) analyzing the target gene for a genomic region comprising clusters of enhancers occupied by an order of magnitude more Mediator than an average enhancer of the target gene; and (b) identifying the genomic region as a super-enhancer associated with the target gene if said clusters of enhancers are occupied by the order of magnitude more Mediator than the average enhancer of the target gene In some embodiments, the order of magnitude is at least 2-fold, 10-fold, at least 15-fold, at least 16-fold, or more.

In some aspects, the present invention relates to a method of identifying a gene, e.g., a key gene or genes, that control a cell state or identity, e.g., contributes to unwanted proliferation, e.g., which contributes to a cancerous cell state, comprising:
(a) identifying a super-enhancer, e.g., within an animal, cell, or cell-free system; and
(b) identifying a gene or genes associated with the super-enhancer, e.g., a gene or genes within a range of proximity to the super-enhancer.

In an embodiment gene or genes that are within a certain proximity to the super-enhancer are identified as a putative key gene or genes that control the cell state or identity.

In an embodiment the method is performed in a cell-free system.

In an embodiment the method is performed in a cell preparation, e.g., a cultured cell preparation.

In an embodiment the method is performed in an animal model.

In an embodiment the method is first performed in a cell-free system, and repeated in a cell preparation, e.g., a cultured cell preparation.

In an embodiment the method is first performed in a cell-free system, or a cell preparation, e.g., a cultured cell preparation, and repeated in an animal.

In an embodiment the cell is a disease state cell, e.g., a cancer cell.

In an embodiment the cell-free system is derived from a disease state cell, e.g., a cancer cell.

In an embodiment, the identified gene is tested as a target for therapy, e.g., by administering an antagonist or inhibitor, e.g., an siRNA, of the product of the gene, to a cell or animal.

The range of proximity to the super-enhancer can extend as far as about 10 megabases (mb) upstream to one end of the super-enhancer to as far as about 10 mb downstream to the other end of the super-enhancer, and any range therebetween, for example 9 mb upstream to 9 mb downstream, 8 mb upstream to 8 mb downstream, 7 mb upstream to 7 mb downstream, 6 mb upstream to 6 mb downstream, 5 mb upstream to 5 mb downstream, 4 mb upstream to 4 mb downstream, 3 mb upstream to 3 mb downstream, 2 mb upstream to 2 mb downstream to 1 mb upstream to 1 mb downstream, or between 0.5 mb upstream and 0.5 mb downstream, 0.1 mb upstream to 0.1 mb downstream. It should be appreciated that the key genes could also, in some instances, overlap with the super-enhancer region. It is also to be understood that the range of proximity will increase or decrease depending on the length or size of the super-enhancer region, for example, if the super-enhancer is 10 kb in length, then the upstream range of proximity extends as far as about 10 mb upstream to the most upstream portion of the 10 kb super-enhancer. Similarly, the downstream range of proximity would extend as far as about 10 mb downstream from the most downstream portion of the 10 kb super-enhancer. In some embodiments, the method of identifying key genes that control the cell state or identity involves measuring the expression of those genes in the cell in the presence and absence of an agent that disrupts the function of the super-enhancer identified, as well as assaying the cell for changes in its cell state or identity (e.g., from a more differentiated state to a less differentiated state, or from a healthy state to a diseased state). If the expression of a gene within the range of proximity is statistically significant when the super-enhancer is properly functioning but its expression decreases or becomes unremarkable in the presence of the agent that disrupts the super-enhancer function, then it is likely that the particular gene is a key gene that controls the cell state or identity, especially if its absence of expression is correlated to a change in the state or identity of the cell.

The aforementioned methods of identifying super-enhancers within a cell and identifying a super-enhancer associated with a target gene can be achieved by a variety of different methods, as would be understood by a person skilled in the art. In some embodiments, the super-enhancer is identified by performing chromatin immunoprecipitation high-throughput sequencing (ChIP-Seq). Example 1 below describes an example of a protocol that can be used to carry out such methods in normal cells, such as embryonic stem cells, for example. Example 2 below describes an example of a protocol that can be used to carry out such methods in tumor cells, such as MM.1S cells, for example.

In certain aspects, the present invention relates to a method of identifying a disease related super-enhancer in a cell, tissue, or organ of an individual suspected of having said disease, comprising: (a) identifying a super-enhancer in said cell, tissue, or organ; (b) identifying a gene associated with said super-enhancer; and (c) and correlating said super-enhancer to said disease.

In certain aspects, the present invention relates to a method of characterizing a subject, e.g, a subject having or suspected of having a disorder, e.g., a proliferative disorder, e.g., cancer, comprising:
acquiring a subject tissue sample;

determining if a super-enhancer is associated with a gene, e.g., a preselected gene, thereby characterizing said subject.

In an embodiment the method comprises determining the genes in the sample that are associated with a super-enhancer.

In an embodiment, the patient is selected, classified, diagnosed, treated, or prognosed, responsive to the pattern of genes, e.g., a preselected pattern, associated with a super-enhancers, e.g., where a plurality of genes, e.g., a plurality of preselected genes, are associated with super-enhancers.

In an embodiment, the determination comprises: crosslinking chromatin from the sample, and selecting, e.g., by immunoprecipitation, a target protein, e.g., an super-enhancer component.

In an embodiment the target protein is a Mediator protein.

In an embodiment the gene or preselected gene is an oncogene, a kinase, a gene that controls cell proliferation, e.g., a myc gene.

In an embodiment the gene or preselected gene is other than an oncogene, a kinase, a gene that controls cell proliferation, e.g., a myc gene.

In an embodiment the method comprises classifying the subject as having a super-enhancer associated with a gene, e.g., a preselected gene.

In an embodiment the sample comprises cancer cells.

In an embodiment the method comprises characterizing a subject by:
acquiring a subject tissue sample;
determining a gene in the sample is associated with a super-enhancer, thereby characterizing said subject.

In an embodiment, responsive to said determination, the method comprises selecting and/or administering a therapy to said subject.

In an embodiment, responsive to said determination, the method comprises selecting, classifying, diagnosing, or prognosing said subject.

In an embodiment, responsive to said determination, the method comprises classifying the subject for treatment with an agent that antagonizes or inhibits the product of the gene or preselected gene.

In an embodiment, responsive to said determination, the method comprises administering to the subject an agent that antagonizes or inhibits the product of the gene or preselected gene.

A reaction mixture comprising a patient sample comprising chromatin from a cancer cell and a probe capable of determining if a preselected gene is associated with an super-enhancer.

In certain aspects, the present invention relates to a method of modifying a cell state or identity, comprising introducing into the cell a super-enhancer that is required to stabilize the cell state or identity. It is to be understood that the super-enhancers of the present invention are capable of modifying the cell state or identity of any cell in which it has been shown that the super-enhancer is required to stabilize the cell state or identity. In some embodiments, the cell state is an embryonic-stem cell like state. Upon introduction of the super-enhancer into the cell, the super-enhancer drives expression of genes that are required to maintain the cell state or identity associated with the super-enhancer.

In some aspects, cell state reflects the fact that cells of a particular type can exhibit variability with regard to one or more features and/or can exist in a variety of different conditions, while retaining the features of their particular cell type and not gaining features that would cause them to be classified as a different cell type. The different states or conditions in which a cell can exist may be characteristic of a particular cell type (e.g., they may involve properties or characteristics exhibited only by that cell type and/or involve functions performed only or primarily by that cell type) or may occur in multiple different cell types. Sometimes a cell state reflects the capability of a cell to respond to a particular stimulus or environmental condition (e.g., whether or not the cell will respond, or the type of response that will be elicited) or is a condition of the cell brought about by a stimulus or environmental condition. Cells in different cell states may be distinguished from one another in a variety of ways. For example, they may express, produce, or secrete one or more different genes, proteins, or other molecules ("markers"), exhibit differences in protein modifications such as phosphorylation, acetylation, etc., or may exhibit differences in appearance. Thus a cell state may be a condition of the cell in which the cell expresses, produces, or secretes one or more markers, exhibits particular protein modification(s), has a particular appearance, and/or will or will not exhibit one or more biological response(s) to a stimulus or environmental condition. Markers can be assessed using methods well known in the art, e.g., gene expression can be assessed at the mRNA level using Northern blots, cDNA or oligonucleotide microarrays, or sequencing (e.g., RNA-Seq), or at the level of protein expression using protein microarrays, Western blots, flow cytometry, immunohistochemistry, etc. Modifications can be assessesed, e.g., using antibodies that are specific for a particular modified form of a protein, e.g., phospho-specific antibodies, or mass spectrometry.

Another example of cell state is "activated" state as compared with "resting" or "non-activated" state. Many cell types in the body have the capacity to respond to a stimulus by modifying their state to an activated state. The particular alterations in state may differ depending on the cell type and/or the particular stimulus. A stimulus could be any biological, chemical, or physical agent to which a cell may be exposed. A stimulus could originate outside an organism (e.g., a pathogen such as virus, bacteria, or fungi (or a component or product thereof such as a protein, carbohydrate, or nucleic acid, cell wall constituent such as bacterial lipopolysaccharide, etc) or may be internally generated (e.g., a cytokine, chemokine, growth factor, or hormone produced by other cells in the body or by the cell itself). For example, stimuli can include interleukins, interferons, or TNF alpha. Immune system cells, for example, can become activated upon encountering foreign (or in some instances host cell) molecules. Cells of the adaptive immune system can become activated upon encountering a cognate antigen (e.g., containing an epitope specifically recognized by the cell's T cell or B cell receptor) and, optionally, appropriate co-stimulating signals. Activation can result in changes in gene expression, production and/or secretion of molecules (e.g., cytokines, inflammatory mediators), and a variety of other changes that, for example, aid in defense against pathogens but can, e.g., if excessive, prolonged, or directed against host cells or host cell molecules, contribute to diseases. Fibroblasts are another cell type that can become activated in response to a variety of stimuli (e.g., injury (e.g., trauma, surgery), exposure to certain compounds including a variety of pharmacological agents, radiation, etc.) leading them, for example, to secrete extracellular matrix components. In the case of response to injury, such ECM components can contribute to wound healing. However, fibroblast activation, e.g., if prolonged, inappropriate, or excessive, can lead to a range of fibrotic conditions affecting diverse tissues and organs (e.g., heart, kidney, liver, intestine, blood vessels, skin) and/or contribute to cancer. The presence of abnormally large amounts of ECM components can result in decreased tissue and organ function, e.g., by increasing stiffness and/or disrupting normal structure and connectivity.

Another example of cell state reflects the condition of cell (e.g., a muscle cell or adipose cell) as either sensitive or resistant to insulin. Insulin resistant cells exhibit decreased respose to circulating insulin; for example insulin-resistant skeletal muscle cells exhibit markedly reduced insulin-stimulated glucose uptake and a variety of other metabolic abnormalities that distinguish these cells from cells with normal insulin sensitivity.

As used herein, a "cell state associated gene" is a gene the expression of which is associated with or characteristic of a cell state of interest (and is often not associated with or is significantly lower in many or most other cell states) and may at least in part be responsible for establishing and/or maintaining the cell state. For example, expression of the gene may be necessary or sufficient to cause the cell to enter or remain in a particular cell state.

In some aspects, modulating a super-enhancer function shifts a cell from an "abnormal" state towards a more "normal" state. In some embodiments, modulating a super-enhancer function shifts a cell from a "disease-associated" state towards a state that is not associated with disease. A "disease-associated state" is a state that is typically found in subjects suffering from a disease (and usually not found in subjects not suffering from the disease) and/or a state in which the cell is abnormal, unhealthy, or contributing to a disease.

In some embodiments, the methods and compounds herein are of use to reprogram a somatic cell, e.g., to a pluripotent state. In some embodiments the methods and compounds are of use to reprogram a somatic cell of a first cell type into a different cell type. In some embodiments, the methods and compounds herein are of use to differentiate a pluripotent cell to a desired cell type.

In an embodiment, the method of modifying a cell state or identity can be used to reprogram a cell to a less differentiated state, such method comprising the steps of:
(a) contacting a differentiated cell or population of cells with at least one reprogramming agent capable of reprogramming said cell to less differentiated state;
(b) maintaining said cell or population of cells under conditions appropriate for proliferation of said cell population and for activity of said at least one reprogramming agent for a period of time sufficient to begin reprogramming of said cell or population of cells; and (c) transfecting said cell or population of cells with a nucleic acid construct comprising a super-enhancer having a plurality of binding sites for cognate transcription factors Oct4, Sox2, and Nanog, wherein transfection of said cell drives high levels of expression of embryonic stem cell genes required to reprogram and maintain the cell in a less differentiated state. In an embodiment, the less differentiated state is an embryonic stem cell-like state. Reprogramming of cells and suitable reprogramming agents (e.g., Oct4, Sox2, Nanog, etc.) are described in further detail in U.S. Patent Application Publication No. 2011/0076678, U.S. Pat. No. 7,682,828, U.S. Pat. No. 8,071,369, U.S. Patent Application Publication No. 2012/0028821, U.S. Patent Application Ser. No. 61/098,327, the teachings of all of which are incorporated herein by reference in their entirety.

In certain aspects, the present invention relates to a kit for reprogramming a differentiated somatic cell population to an embryonic stem-cell like state, comprising: (a) a population of differentiated somatic cells; (b) at least one reprogramming agent capable of reprogramming said cell to an embryonic stem cell-like state; and (c) a nucleic acid construct comprising a super-enhancer containing clusters of enhancers having binding sites for cognate transcription factors Oct4, Sox2, and Nanog; and (d) a reagent for transfecting said population of cells with said nucleic acid construct.

In some embodiments, modulating a function (activity) of a super-enhancer is of use to treat, e.g., a metabolic, neurodegenerative, inflammatory, auto-immune, proliferative, infectious, cardiovascular, musculoskeletal, or other disease. It will be understood that diseases can involve multiple pathologic processes and mechanisms and/or affect multiple body systems. Discussion herein of a particular disease in the context of a particular pathologic process, mechanism, cell state, cell type, or affected organ, tissue, or system, should not be considered limiting. For example, a number of different tumors (e.g., hematologic neoplasms such as leukemias) arise from undifferentiated progenitor cells and/or are composed largely of undifferentiated or poorly differentiated cells that retain few if any distinctive features characteristic of differentiated cell types. These tumors, which are sometimes termed undifferentiated or anaplastic tumors, may be particularly aggressive and/or difficult to treat. In some embodiments of the invention, a method of the invention is used to modify such cells to a more differentiated state, which may be less highly proliferative and/or more amenable to a variety of therapies, e.g., chemotherapeutic agents. In another embodiment, an inventive method is used to treat insulin resistance which occurs, for example, in individuals suffering from type II diabetes and pre-diabetic individuals. It would be beneficial to modify the state of insulin-resistant cells towards a more insulin-sensitive state, e.g., for purposes of treating individuals who are developing or have developed insulin resistance. In another embodiment, an inventive method is used to treat obesity.

Many inflammatory and/or autoimmune conditions may occur at least in part as a result of excessive and/or inappropriate activation of immune system cells. Autoimmune diseases include, e.g., Graves disease, Hashimoto's thyroiditis, myasthenia gravis, rheumatoid arthritis, sarcoidosis, Sjögren's syndrome, scleroderma, ankylosing spondylitis, type I diabetes, vasculitis, and lupus erythematosus. Furthermore, immune-mediated rejection is a significant risk in organ and tissue transplantation. Inflammation plays a role in a large number of diseases and conditions. Inflammation can be acute (and may be recurrent) or chronic. In general, inflammation can affect almost any organ, tissue, or body system. For example, inflammation can affect the cardiovascular system (e.g., heart), musculoskeletal system, respiratory system (e.g., bronchi, lungs), renal system, (e.g., kidneys), eyes, nervous system, gastrointestinal system (e.g., colon), integumentary system (e.g., skin), musculoskeletal system (e.g., joints, muscles), resulting in a wide variety of conditions and diseases. Chronic inflammation is increasingly recognized as an important factor contributing to atherosclerosis and degenerative diseases of many types. Inflammation influences the microenvironment around tumours and contributes, e.g., to tumor cell proliferation, survival and migration. Furthermore, chronic inflammation can eventually lead to fibrosis.

Exemplary inflammatory diseases include, e.g., adult respiratory distress syndrome (ARDS), atherosclerosis (e.g., coronary artery disease, cerebrovascular disease), allergies, asthma, cancer, demyleinating diseases, dermatomyositis, inflammatory bowel disease (e.g., Crohn's disease, ulcerative colitis), inflammatory myopathies, multiple sclerosis, glomerulonephritis, psoriasis, pancreatitis, rheumatoid arthritis, sepsis, vasculitis (including phlebitis and arteritis, e.g., polyarteritis nodosa, Wegener's granulomatosis, Buerger's disease, Takayasu's arteritis, etc.). In some embodiments, a method of the invention is used to modify immune cell state to reduce activation of immune system cells involved in such conditions and/or render immune system cells tolerant to one or more antigens. In one embodiment, dendritic cell state is altered. Promoting immune system activation using a method of the invention (e.g., in individuals who have immunodeficiencies or have been treated with drugs that deplete or damage immune system cells), potentially for limited periods of time, may be of benefit in the treatment of infectious diseases.

In other embodiments, activated fibroblasts are modified to a less activated cell state to reduce or inhibit fibrotic conditions or treat cancer.

Post-surgical adhesions can be a complication of, e.g., abdominal, gynecologic, orthopedic, and cardiothoracic surgeries. Adhesions are associated with considerable morbidity and can be fatal. Development of adhesions involves inflammatory and fibrotic processes. In some embodiments, a method of the invention is used to modify state of immune system cells and/or fibroblasts to prevent or reduce adhesion formation or maintenance.

In other embodiments, modifying cells to a more or less differentiated state is of use to generate a population of cells in vivo that aid in repair or regeneration of a diseased or damaged organ or tissue, or to generate a population of cells ex vivo that is then administered to a subject to aid in repair or regeneration of a diseased or damaged organ or tissue.

In some embodiments, cell type and/or cell state becomes modified over the course of multiple cell cycle(s). In some embodiments, cell type and/or cell state is stably modified. In some embodiments, a modified type or state may persist for varying periods of time (e.g., days, weeks, months, or indefinitely) after the cell is no longer exposed to the agent(s) that caused the modification. In some embodiments, continued or at intermittent exposure to the agent(s) is required or helpful to maintain the modified state or type.

Cells may be in living animal, e.g., a mammal, or may be isolated cells. Isolated cells may be primary cells, such as those recently isolated from an animal (e.g., cells that have undergone none or only a few population doublings and/or passages following isolation), or may be a cell of a cell line that is capable of prolonged proliferation in culture (e.g., for longer than 3 months) or indefinite proliferation in culture (immortalized cells). In many embodiments, a cell is a somatic cell. Somatic cells may be obtained from an individual, e.g., a human, and cultured according to standard cell culture protocols known to those of ordinary skill in the art. Cells may be obtained from surgical specimens, tissue or cell biopsies, etc. Cells may be obtained from any organ or tissue of interest. In some embodiments, cells are obtained from skin, lung, cartilage, breast, blood, blood vessel (e.g., artery or vein), fat, pancreas, liver, muscle, gastrointestinal tract, heart, bladder, kidney, urethra, prostate gland. Cells may be maintained in cell culture following their isolation. In certain embodiments, the cells are passaged or allowed to double once or more following their isolation from the individual (e.g., between 2-5, 5-10, 10-20, 20-50, 50-100 times, or more) prior to their use in a method of the invention. They may be frozen and subsequently thawed prior to use. In some embodiments, the cells will have been passaged or permitted to double no more than 1, 2, 5, 10, 20, or 50 times following their isolation from the individual prior to their use in a method of the invention. Cells may be genetically modified or not genetically modified in various embodiments of the invention. Cells may be obtained from normal or diseased tissue. In some embodiments, cells are obtained from a donor, and their state or type is modified ex vivo using a method of the invention. The modified cells are administered to a recipient, e.g., for cell therapy purposes. In some embodiments, the cells are obtained from the individual to whom they are subsequently administered.

A population of isolated cells in any embodiment of the invention may be composed mainly or essentially entirely of a particular cell type or of cells in a particular state. In some embodiments, an isolated population of cells consists of at least 30%, 40%, 50%, 60%, 70%, 80%, 90%, 95%, 96%, 97%, 98%, 99%, or 100% cells of a particular type or state (i.e., the population is at least 30%, 40%, 50%, 60%, 70%, 80%, 90%, 95%, 96%, 97%, 98%, 99%, or 100% pure), e.g., as determined by expression of one or more markers or any other suitable method.

In certain aspects, the present invention relates to a method of selectively inhibiting expression of an aberrantly expressed gene comprising disrupting the function of a super-enhancer associated with the gene. In certain embodiments, the gene comprises an oncogene. During the course of work described herein, the present inventors have observed that disruption of super-enhancers by BRD4 inhibition led to a dramatic loss of expression of critical tumor genes, accompanied by a potent anti-proliferative effect. Given the fact that super-enhancers are common features of mammalian cells, and that super-enhancers have been shown to drive high levels of gene expression, it is reasonable to expect that super-enhancer disruption can be used to selectively inhibit expression of any gene (e.g., any gene that is overexpressed in a diseased cell, wherein the gene is associated with a super-enhancer) by disrupting the super-enhancer associated with the oncogene. In an embodiment, the oncogene is MYC. In an embodiment, the oncogene is IRF4.

It should be appreciated that the present invention contemplates the use of any technique or any agent that is capable of disrupting the function of the super-enhancer. Generally, disrupting the function of the super-enhancer involves contacting said super-enhancer region with an effective amount of an agent that interferes with occupancy of the super-enhancer region by a cognate transcription factor for the gene, a transcriptional coactivator, or a chromatin regulator. In some embodiments, disrupting the function of the super-enhancer can be achieved by contacting the super-enhancer region with a pause release agent. In certain embodiments, the agent interferes with a binding site on the super-enhancer for the cognate transcription factor, interferes with interaction between the cognate transcription factor and a transcriptional coactivator, inhibits the transcription coactivator, or interferes with or inhibits the chromatin regulator. In some embodiments, the agent is a bromodomain inhibitor. In some embodiments, the agent is a BRD4 inhibitor. In some embodiments, the agent is the compound JQ1. In some embodiments, the agent is iBET.

Any of a wide variety of agents (also termed "compounds") can be used to disrupt the function of the super-enhancer, such as BET bromodomain inhibitors, P-TEFb inhibitors or compounds that interfere with binding of the cognate transcription factors to the binding sites of the super-enhancer associated with the gene (e.g, if the gene is an oncogene, such as MYC, a c-Myc inhibitor can be used to disrupt the function of the super-enhancer). An inhibitor could be any compound that, when contacted with a cell, results in decreased functional activity of a molecule or complex, e.g., transcriptional coactivator (e.g., Mediator), a chromatin regulator (e.g., BRD4), an elongation factor (e.g., P-TEFb), or cognate transcription factor (e.g., a cognate oncogenic transcription factor), in the cell. An inhibitor could act directly, e.g., by physically interacting with a molecule or complex to be inhibited, or a component thereof, or indirectly such as by interacting with a different molecule or complex required for activity of the molecule or complex to be inhibited, or by interfering with expression or localization.

Compounds of use in various embodiments of the invention can comprise, e.g., small molecules, peptides, polypeptides, nucleic acids, oligonucleotides, etc. Certain non-limiting examples are presented below.

A small molecule is often an organic compound having a molecular weight equal to or less than 2.0 kD, e.g., equal to or less than 1.5 kD, e.g., equal to or less than 1 kD, e.g., equal to or less than 500 daltons and usually multiple carbon-carbon bonds. Small molecules often comprise one or more functional groups that mediate structural interactions with proteins, e.g., hydrogen bonding, and typically include at least an amine, carbonyl, hydroxyl or carboxyl group, and in some embodiments at least two of the functional chemical groups. A small molecule may comprise cyclic carbon or heterocyclic structures and/or aromatic or polyaromatic structures substituted with one or more chemical functional groups and/or heteroatoms. In some embodiments a small molecule satisfies at least 3, 4, or all criteria of Lipinski's "Rule of Five". In some embodiments, a compound is cell-permeable, e.g., within the range of typical compounds that act intracellularly, e.g., within mammalian cells. In some embodiments, the IC50 of a compound, e.g., a small molecule, for a target to be inhibited is less than or equal to about 5 nM, 10 nM, 50 nM, 100 nM, 500 nM, 1 µM, 10 µM, 50 µM, or 100 µM, Nucleic acids, e.g., oligonucleotides (which typically refers to short nucleic acids, e.g., 50 nucleotides in length or less), the invention contemplates use of oligonucleotides that are single-stranded, double-stranded (ds), blunt-ended, or double-stranded with overhangs, in various embodiments of the invention. The full spectrum of modifications (e.g., nucleoside and/or backbone modifications), non-standard nucleotides, delivery vehicles and systems, etc., known in the art as being useful in the context of siRNA or antisense-based molecules for research or therapeutic purposes is contemplated for use in various embodiments of the instant invention. In some embodiments a compound is an RNAi agent, antisense oligonucleotide, or aptamer. The term "RNAi agent" encompasses nucleic acids that can be used to achieve RNA silencing in mammalian cells. As used herein RNA silencing, also termed RNA interference (RNAi), encompasses processes in which sequence-specific silencing of gene expression is effected by an RNA-induced silencing complex (RISC) that has a short RNA strand incorporated therein, which strand directs or "guides" sequence-specific degradation or translational repression of mRNA to which it has complementarity. The complementarity between the short RNA and mRNA need not be perfect (100%) but need only be sufficient to result in inhibition of gene expression. For example, the degree of complementarity and/or the characteristics of the structure formed by hybridization of the mRNA and the short RNA strand can be such that the strand can (i) guide cleavage of the mRNA in the RNA-induced silencing complex (RISC) and/or (ii) cause translational repression of the mRNA by RISC. The short RNA is often incorporated into RISC as part of a short double-stranded RNA (dsRNA). RNAi may be achieved artificially in eukaryotic, e.g., mammalian, cells in a variety of ways. For example, RNAi may be achieved by introducing an appropriate short double-stranded nucleic acid into the cells or expressing in the cells a nucleic acid that is processed intracellularly to yield such short dsRNA. Exemplary RNAi agents are a short hairpin RNA (shRNA), a short interfering RNA (siRNA), micrRNA (miRNA) and a miRNA precursor. siRNAs typically comprise two separate nucleic acid strands that are hybridized to each other to form a duplex. They can be synthesized in vitro, e.g., using standard nucleic acid synthesis techniques. A nucleic acid may contain one or more non-standard nucleotides, modified nucleosides (e.g., having modified bases and/or sugars) or nucleotide analogs, and/or have a modified backbone. Any modification or analog recognized in the art as being useful for RNAi, aptamers, antisense molecules or other uses of oligonucleotides can be used. Some modifications result in increased stability, cell uptake, potency, etc. Exemplary compound can comprise morpholinos or locked nucleic acids. In some embodiments the nucleic acid differs from standard RNA or DNA by having partial or complete 2'-O-methylation or 2'-O-methoxyethyl modification of sugar, phosphorothioate backbone, and/or a cholesterol-moiety at the 3'-end. In certain embodiments the siRNA or shRNA comprises a duplex about 19 nucleotides in length, wherein one or both strands has a 3' overhang of 1-5 nucleotides in length (e.g., 2 nucleotides), which may be composed of deoxyribonucleo tides. shRNA comprise a single nucleic acid strand that contains two complementary portions separated by a predominantly non-self-complementary region. The complementary portions hybridize to form a duplex structure and the non-self-complementary region forms a loop connecting the 3' end of one strand of the duplex and the 5' end of the other strand. shRNAs can undergo intracellular processing to generate siRNAs. In certain embodiments the term "RNAi agent" also encompasses vectors, e.g., expression vectors, that comprise templates for transcription of an siRNA (e.g., as two separate strands that can hybridize), shRNA, or microRNA precursor, and can be used to introduce such template into mammalian cells and result in transient or stable expression thereof.

In some embodiments an RNAi agent, aptamer, antisense oligonucleotide, other nucleic acid, peptide, polypeptide, or small molecule is physically associated with a moiety that increases cell uptake, such as a cell-penetrating peptide, or a delivery agent. In some embodiments a delivery agent at least in part protects the compound from degradation, metabolism, or elimination from the body (e.g., increases the half-life). A variety of compositions and methods can be used to deliver agents to cells in vitro or in vivo. For example, compounds can be attached to a polyalkylene oxide, e.g., polyethylene glycol (PEG) or a derivative thereof, or incorporated into or attached to various types of molecules or particles such as liposomes, lipoplexes, or polymer-based particles, e.g., microparticles or nanoparticles composed at least in part of one or more biocompatible polymers or copolymers comprising poly(lactide-glycolide), copolyoxalates, polycaprolactones, polyesterar des, polyorthoesters, polyhydroxybutyric acid, and/or polyanhydrides.

In some embodiments, an agent comprises a polypeptide. A "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. In some embodiments, a non-standard, naturally occurring amino acid is found in mammals. For example, ornithine, citrulline, and homocysteine are naturally occurring non-standard amino acids that have important roles in mammalian metabolism. Exemplary non-standard amino acids include, e.g., singly or multiply halogenated (e.g., fluorinated) amino acids, D-amino acids, homo-amino acids, N-alkyl amino acids (other than proline), dehydroamino acids, aromatic amino acids (other than histidine, phenylalanine, tyrosine and tryptophan), and α,α disubstituted amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, etc. Modifications may occur anywhere in a polypeptide, e.g., the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like. Modification may occur prior to or after an amino acid is incorporated into a polypeptide in various embodiments. Polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing.

One of ordinary skill in the art will understand that a protein may be composed of a single amino acid chain or multiple chains associated covalently or noncovalently. In some embodiments, the agent is a non-functional mutant of the cognate oncogenic transcription factor, the transcriptional coactivator, or the chromatin regulator that mimics interactions of the cognate oncogenic transcription factor, the transcriptional coactivator, or the chromatin regulator but lacks the ability to activate transcription of the oncogene. For example, a polypeptide can be a dominant negative version of Mediator, an elongation factor (e.g., P-TEFb subunit) or a dominant negative version of a cognate oncogenic transcription factor (e.g., a c-Myc or Max). A polypeptide that binds to and inhibits Mediator or P-TEFb or c-Myc could be identified, e.g., using phage display.

In some embodiments a compound comprises an antibody. The term "antibody" encompasses immunoglobulins and derivatives thereof containing an immunoglobulin domain capable of binding to an antigen. An antibody can originate from any mammalian or avian species, e.g., human, rodent (e.g., mouse, rabbit), goat, chicken, etc., or can be generated using, e.g., phage display. The antibody may be a member of any immunoglobulin class, e.g., IgG, IgM, IgA, IgD, IgE, or subclasses thereof such as IgG1, IgG2, etc. In various embodiments of the invention "antibody" refers to an antibody fragment such as an Fab', F(ab')2, scFv (single-chain variable) or other fragment that retains an antigen binding site, or a recombinantly produced scFv fragment, including recombinantly produced fragments. An antibody can be monovalent, bivalent or multivalent in various embodiments. The antibody may be a chimeric or "humanized" antibody, which can be generated using methods known in the art. An antibody may be polyclonal or monoclonal, though monoclonal antibodies may be preferred. Methods for producing antibodies that specifically bind to virtually any molecule of interest are known in the art. In some aspects the antibody is an intrabody, which may be expressed intracellularly. In some embodiments a compound comprises a single-chain antibody and a protein transduction domain (e.g., as a fusion polypeptide).

In some embodiments, a composition or method of the invention employs a transcriptional coactivator inhibitor, a chromatin regulator inhibitor, an elongation factor or pause release inhibitor, or a cognate transcription factor inhibitor that are small molecules.

In some embodiments, the agent is a BET bromodomain inhibitor. In some embodiments, the agent is a BRD4 inhibitor. In some embodiments, the agent is JQ1. In some embodiments, the agent is iBET. In some embodiments, the elongation factor or pause release inhibitor is a P-TEFb inhibitor. In some embodiments, the cognate oncogenic transcription factor inhibitor is a c-Myc inhibitor. In some embodiments, a composition or method employs a Mediator inhibitor, a BRD4 inhibitor, a P-TEFb inhibitor and a c-Myc inhibitor that each comprise a nucleic acid, e.g., RNAi agents. In some embodiments, a composition or method employs a Mediator inhibitor, a P-TEFb inhibitor that comprises a nucleic acid, e.g., RNAi agents, e.g., siRNAs. In some embodiments, the Mediator inhibitor may bind to a Mediator component, Mediator complex, or a Mediator associated protein, for example, an antibody directed against the Mediator component, Mediator complex, or the Mediator associated protein. Examples of suitable antibodies can be found in PCT International Application No. WO 2011/100374, the teachings of which are incorporated herein by reference in their entirety.

In some embodiments the material is isolated using an agent (e.g., an antibody) that binds to a Mediator component, Mediator complex, or that binds to a Mediator-associated protein.

In some embodiments, the agent is a nucleic acid that hybridizes to a binding site on the super-enhancer for the cognate transcription factor.

Compounds can be produced using any suitable method known in the art. The skilled artisan will select an appropriate method based, e.g., on the nature of the compound. The production method can be partially or completely synthetic in various embodiments. In some embodiments a compound (or starting material for synthesis) is purified from an organism or other natural source, e.g., a plant, microbe, fermentation broth, etc. A compound of use in the invention may be provided as part of a composition, which may contain, e.g., anion, salt, aqueous or non-aqueous diluent or carrier, buffer, preservative, etc. It is noted that although combined use of compounds is of particular interest, the use of compounds disclosed herein is not limited to their use in combination. In some embodiments of the invention, a compound may be used as a single agent.

In some embodiments, a P-TEFb inhibitor inhibits CDK9 kinase activity. The compound may inhibit one or more additional kinases, e.g., CDKs, in addition to CDK9. Often a kinase inhibitor acts by binding to an ATP binding pocket of a kinase. Thus in some embodiments a CDK9 inhibitor binds to the ATP binding pocket of CDK9. In some embodiments the P-TEFb inhibitor is selective for CDKs relative to many, most, or all other kinase families. In some embodiments the CDK inhibitor is selective for CDKs 1, 4, and 9 versus CDK2. In some embodiments the P-TEFb inhibitor is a CDK inhibitor that is selective for CDK9 versus CDK2. In some embodiments the P-TEFb inhibitor is a CDK inhibitor that is selective for CDK9 versus CDK1 and CDK4. It will be appreciated that kinase inhibitory activity is tested against CKDs in complex with a preferred cyclin partner. For example, in some embodiments CDK2 activity can be tested using cyclin A. It will also be appreciated that a kinase assay can employ a relevant substrate, e.g., a physiologically relevant substrate or portion thereof comprising a phosphoryation site for the kinase.

In some embodiments, the compound is an N-methylpiperidinyl, chlorophenyl flavone. In some embodiments, the compound is flavopiridol or a flavopiridol analog.

Flavopiridol (−)-2-(2-Chlorophenyl)-5,7-dihydroxy-8-[(3S,4R)-3-hydroxy-1-methyl-4-piperidinyl]-4H-1-benzopyran-4-one hydrochloride is a synthetic flavone that inhibits multiple CDKs, including CDK9. Its structure is shown below.

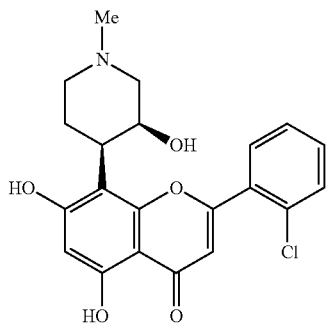 [SMILES: CN1CC[C@H](c2c(O)cc(O)c3c(=O)cc(-c4ccccc4Cl)oc23)[C@H](O)C1]

Flavopiridol has been shown to have antitumor activity against various tumor cells lines and to inhibit tumor growth in xenograft models. It has undergone clinical trials in a number of different cancer types including various solid tumors and leukemias. As described further in the examples, flavopiridol was shown to inhibit pause release. Without wishing to be bound by theory, this may help counteract the effects of Myc overexpression, and this may be the basis for the therapeutic effect of flavopiridol on some tumors.

Flavopiridol analogs include compounds designed based on flavopiridol, e.g., by modifying one or more of the rings of the flavopiridol structure at one or more positions. In some embodiments, a flavopiridol analog is a 2-thio or 2-oxo flavopiridol analog. For example, PCT/US 1997/007610 describes compounds of formula I:

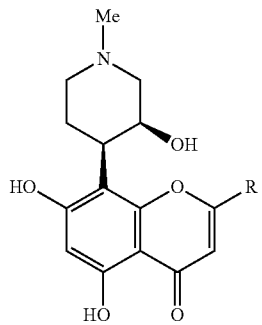

wherein X is oxygen or sulfur; $R^1$, $R^2$, $R^3$, $R^4$, $R^5$, $R^6$, m, and n are as defined in PCT/US1997/007610.

Additional flavopiridol analogs are disclosed in Murthi, K. K., et al., Bioorg Med Chem Lett. 10(10): 1037-41, 2000, which describes modifications of the 3-hydroxy-1-methylpiperidinyl (D ring) of flavopiridol.

In some embodiments, a flavopiridol analog has the following structure:

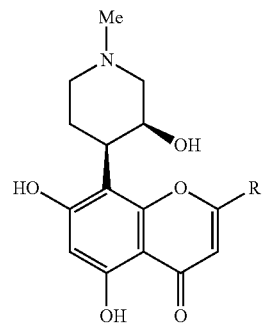

In some embodiments R is phenyl or substituted phenyl, e.g., halogenated phenyl. In some embodiments, R is selected from the group consisting of: 3-chlorophenyl, 4-chlorophenyl, 2-fluorophenyl, 4-fluorophenyl, 4-bromophenyl, 4-t-butylphenyl, 4-trifluoromethylphenyl, 4-hydroxyphenyl, 2-pyridyl, 3-pyridyl, 4-pyridyl, 4-chloro-3-pyridyl, 5-methylisoxazole, 3-vinylphenyl, 4-vinylphenyl, 2-chlorophenyl, 4-fluorophenyl, 2-bromophenyl, and 3-pyridyl. In some embodiments the compound displays increased selectivity for CDK9 than does flavopiridol. See, e.g., Ali, A., et al., Chembiochem, 10(12):2072-80, 2009, for additional information regarding these compound.

In some embodiments, a CDK9 inhibitor has the following structure:

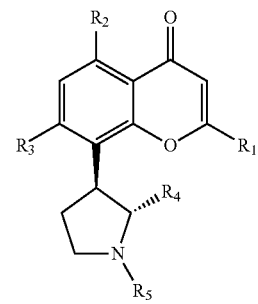

wherein R1, R2, R3, R4, and R9 are as defined in PCT/IB 2006/052002 (WO/2007/148158). In some embodiments (i) RI comprises an aromatic group; (ii) R4 comprises an R—(OH) group, wherein R is a $C_{1-6}$ aliphatic group; (iii) R9 comprises a $C_{1-6}$ aliphatic group, e.g, a methyl group; or (iv) any combination of (i), (ii), and (iii). In some embodiments, the compound may have the following structure:

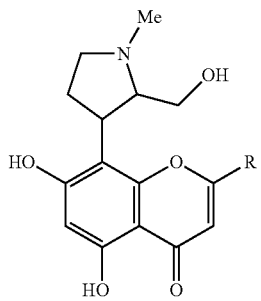

wherein R comprises an aromatic group.

Crystal structures of P-TEFb (CDK9/cyclin T1) alone and in a complex with flavopiridol are available (Baumli, S., et al., EMBO J. 27(13): 1907-18, 2008). Flavopiridol was shown to bind to the ATP binding pocket of CDK9. Structural information can be used in the design of additional P-TEFb inhibitors including, but not limited to, additional analogs of flavopiridol. Furthermore, virtual screening can be performed using structural information regarding diverse chemical compounds to identify candidate P-TEFb inhibitors. In some embodiments, a P-TEFb inhibitor is a compound that makes similar intermolecular contacts with CDK9 as does flavopiridol. Similar approaches can be used to design analogs of other CDK9 inhibitors.

In some embodiments, a flavopiridol analog exhibiting reduced binding to human serum relative to flavopiridol is used.

In some embodiments, the P-TEFb inhibitor is a purine or purine analog, e.g., a biaryl purine analog. In some embodiments, the purine analog is a 2,6,9-substituted purine analog. In some embodiments, the compound is roscovitine, e.g., S-roscovitine or R-roscovitine. Unless otherwise indicated, where roscovitine is mentioned herein, the roscovitine can be R-roscovitine (also called Seliciclib or CYC202; 2-(R)-(1-Ethyl-2-hydroxyethy lamino)-6-benzylamino-9-isopropyl purine). Roscovitine is a CDK inhibitor that preferentially inhibit multiple enzyme targets including CDK1, CDK2, CDK7 and CDK9 and has been studied in clinical trials for treatment of a variety of proliferative diseases.

In some embodiments the compound is a roscovatine analog. Exemplary roscovitine analogs are oloumicine (2-(2-hydroxyethylamino)-6-benzylamino-9-methylpurine), olomoucine II (6-[(2-hydroxybenzyfiamino]-2-[[1-(hydroxymethyl)propyl]amino]-9-isopropylpurine) and LGR1406 (N-5-(2-aminocyclohexyl)-N-7-benzyl-3-isopropyl-1(2)H-pyrazolo[4,3-d]pyrimidine-5,7-di-amine). Roscovitine analogs generated by introduction of an aryl ring onto the 4-position of the C-6 benzyl amino group of roscovitine, and a series of C-6 biarylmethylamino derivatives prepared with modifications on the C-6 biaryl rings, N-9 and C-2 positions, are described in Trova, M P, et. al., Bioorg Med Chem Lett. 19(23):6608-12, 2009.

Many additional CDK inhibitors are known in the art that may inhibit CDK9, optionally with at least some selectivity relative to inhibition of one or more other CDKs. For example, PCT/US2009/049637 (WO/2010/003133) discloses compounds that are reported to inhibit CDK9. In some aspects, the compounds have the following structure, where R1 and R3 are as defined therein.

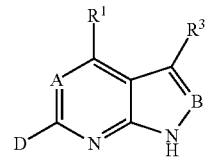

PCT/EP2008/063715 (WO 2009047359) discloses additional compounds that are reported to inhibit CDK9. In some aspects, the compounds have the following structure, wherein R1, R2, Ra, and (R3)$_x$ are as defined therein.

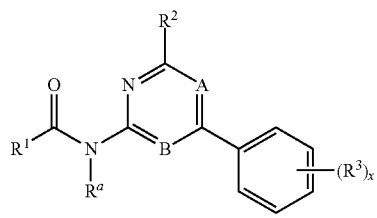

In some embodiments, a P-TEFb inhibitor comprises an RNAi agent (e.g., an siRNA) or an antisense oligonucleotide that inhibits expression of a P-TEFb subunit (e.g., CDK9, cyclin T1, T2a, T2b, or K). In some embodiments a P-TEFb inhibitor comprises an antibody or aptamer that specifically binds to a P-TEFb subunit. Optionally the antibody or aptamer may bind to multiple CDKs or cyclins.

In some embodiments, a c-Myc inhibitor is a small molecule. In some embodiments, a c-Myc inhibitor inhibits formation of c-Myc/Max heterodimers. In some embodiments, a c-Myc inhibitor inhibits binding of c-Myc/Max to a target site in DNA. In some embodiments a c-Myc inhibitor is relatively specific for inhibiting transcription mediated by c-Myc relative to transcription mediated by many or most other basic helix-loop-helix/leucine zipper transcription factors.

Various compounds that inhibit c-Myc are described in Berg, T., Curr. Op. Chem. Biol., 12: 464-471, 2008, and references therein. The peptide mimetic IIA6B17 is described in Berg, T., et al., Proc Natl Acad Sci USA 99 (2002), pp. 3830-3835 and was shown to inhibit c-Myc-dependent transcription in a reporter gene assay (X. Lu, et al. Oncol Rep 19 (2008), pp. 825-830.). Testing a 285 member chemical library derived from planar, aromatic scaffolds in a c-Myc/Max dimerization assay led to identification of four structurally related Myc/Max dimerization inhibitors, which also inhibited DNA binding of c-Myc/Max (Y. Xu, et al. Bioorg Med Chem 14 (2006), pp. 2660-2673.) For example, the compound NY2267 strongly inhibited c-Myc-dependent oncogenic transformation of chicken embryo fibroblasts at 20 μM, showed selectivity over transformation mediated by v-Src or v-Jun, but did not discriminate between transcription mediated by c-Jun and c-Myc. Several compounds were selected from a chemical library on the basis of their ability to prevent association of the HLH-Zip domains of c-Myc and Max in a yeast two-hybrid assay (X. Yin, et al., Oncogene 22 (2003), pp. 6151-6159.). One, 10058-F4 (IC$_{50}$=49 μM on HL60 cells), served as starting point for the testing of derivatives with improved activities. One of the numerous derivatives resulting from structural variation of the substituents on the aromatic ring and the rhodanine moiety, the compound 28RH-NCN-1, inhibited DNA binding of c-Myc with activity comparable to that of the parent compound, and inhibited growth of HL60 cells with improved potency ($IC_{50}$=29 μM) (Wang, H., et al., Mol Cancer Ther 6 (2007), pp. 2399-2408). See also PCT/US2007/004039 (WO/2007/098010).

Screening chemical libraries for compounds that inhibited DNA binding of c-Myc, led to discovery of the pyrazolo[1,5-a]pyrimidine Mycro1 (Kiessling, A., et al., Chem Biol 13 (2006), pp. 745-751.). Mycro1 and the derivative Mycro2 were subsequently shown to inhibit c-Myc/Max dimerization, c-Myc-dependent proliferation, gene transcription, and oncogenic transformation. While Mycro1 and Mycro2 displayed good specificities in vitro, they showed only weak-to-moderate specificity for c-Myc-dependent transcription over transcription mediated by AP-1 family proteins, which also dimerize via leucine zippers. A follow-up screen using a focused library of pyrazolo[1,5-a]pyrimidines led to the discovery of the pyrazolo[1,5-fl]pyrimidine 1 (Mycro3), which inhibited c-Myc/Max dimerization and DNA binding with very good selectivity in vitro, and also showed good potency and selectivity at concentrations of 10-40 μM against c-Myc in cellular assays (A. Kiessling, A, et al., ChemMedChem 2 (2007), pp. 627-630.).

It can be reasoned that inhibitors of the DNA-protein interactions between intact c-Myc/Max dimers and their DNA recognition motif should not interfere with gene transcription repressed by c-Myc, but would still block c-Myc induced transcriptional activation. This distinction can be used to help selectively identify compounds having this mechanism of action. In a screen designed to identify compounds that particularly affect cells with high levels of c-Myc, a compound termed MYRA-A, was discovered, which was shown to inhibit Myc-regulated gene expression, oncogenic transformation, and to induce apoptosis in a Myc-dependent manner (H. Mo and M. Hennksson, Proc Natl Acad Sci USA 103 (2006), pp. 6344-6349.). In a subsequent study, the same group published an additional inhibitor of DNA binding of c-Myc/Max family members dubbed NSC308848 (Mo, H., et al. Cell Cycle 5 (2006), pp. 2191-2194.).

Hammoudeh, et al. (2009) identified multiple small molecule binding sites on c-Myc, facilitating use of drug design and/or virtual screening to identify additional c-Myc inhibitors.

Some exemplary small molecule c-Myc inhibitors of use in various embodiments of the invention are shown below. In certain embodiments of the invention analogs of any of these compounds are used.

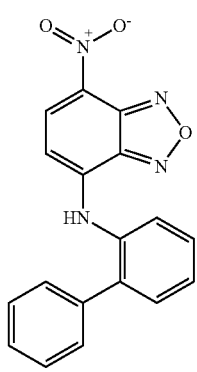

10074-GS

-continued

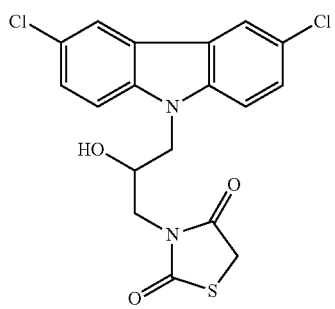

10074-A4

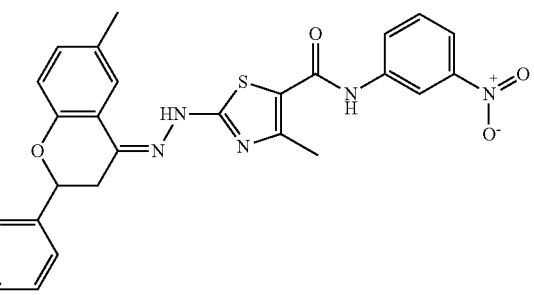

10050-C10

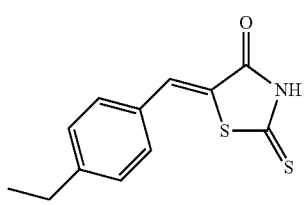

1 CSQSS~F4

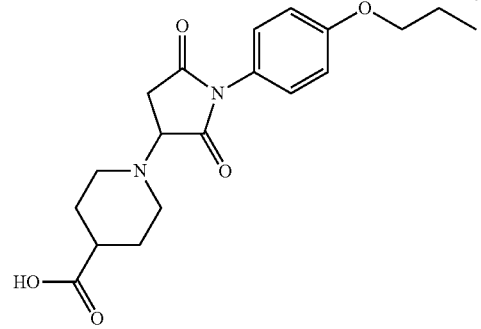

1Q831-B8

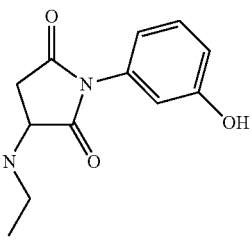

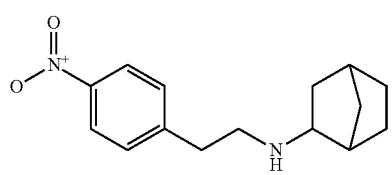

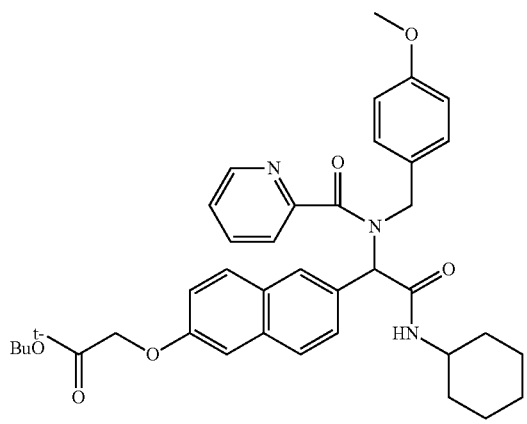

NY2267

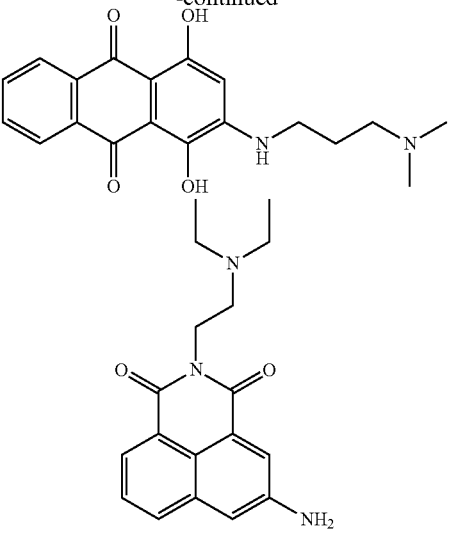

28RH-NCN-1

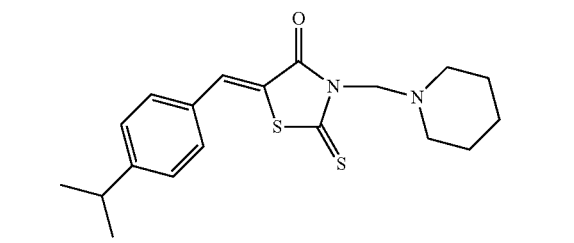

IIA6B17

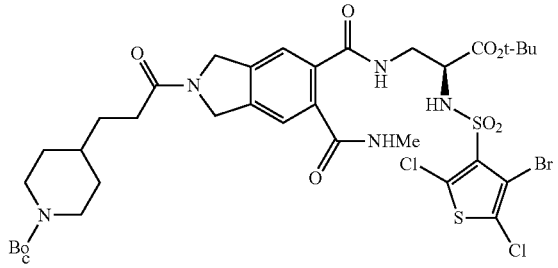

Mycro 1

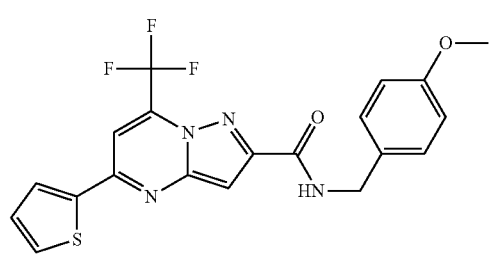

Mycro 3

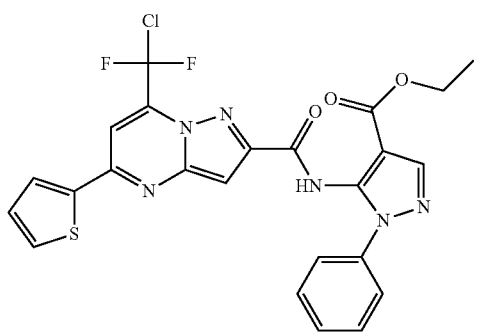

In some embodiments, a c-Myc inhibitor comprises an RNAi agent (e.g., an siRNA) or an antisense oligonucleotide that inhibits expression of c-Myc. In some embodiments a c-Myc inhibitor comprises an antibody or aptamer that specifically binds to c-Myc.

In some embodiments the agent promotes proteolysis of a polypeptide encoded by an oncogene in a cell (e.g., a tumor cell) exhibiting excessive levels of the cognate transcription factor and more transcriptional coactivator and chromatin regulator occupancy of the super-enhancer then the average single enhancer for the oncogene (e.g., an order of magnitude more). In some embodiments the agent promotes global proteolysis in cell-specific manner such that global proteolysis is only induced in those cells (e.g., tumor cells) exhibiting extremely high levels of the cognate transcription factor of the gene and transcriptional coactivator super-enhancer occupancy. In some embodiments the agent promotes proteolysis of a polypeptide encoded by one or more of a plurality of oncogenes in a cell in which cognate transcription factor levels are high and super-enhancers of the oncogene are occupied by more transcriptional coactivator than the average single enhancer of the oncogene.

The present invention contemplates the use of any agent that is capable of promoting proteolysis. In some embodiments the agent promotes global proteolysis of polypeptides encoded by the oncogenes. In some embodiments the agent promotes global proteolysis of polypeptides encoded by the oncogenes is promoted in cells that exhibit elevated cognate oncogenic transcription factors for the oncogene. In some embodiments the agent promotes global proteolysis of polypeptides is specific to tumor cells that possess oncogenes associated with super-enhancers. In some embodiments the agent promotes global proteolysis of polypeptides in cells that exhibit elevated cognate oncogenic transcription factors and excessive levels of transcriptional co-activator and/or chromatin regulator co-occupancy of super-enhancers and active transcription start sites.

In some embodiments the agent promotes global proteolysis of polypeptides by targeting the oncogene and its expression products for ubiquitin-dependent proteolysis. In some embodiments, the agent promotes global proteolysis of polypeptides by ubiquitin-dependent proteolysis by the proteasome. Ubiquitin-dependent proteolysis is a pathway used by eukaryotic cells for degrading cellular proteins. Protein ubiquitination is catalyzed by the concerted actions of three classes of enzymes; the E1 ubiquitin-activating enzymes, the E2 ubiquitin-conjugating enzymes, and the E3 ubiquitin protein ligases (Hochstrasser, Annu Rev. Genet 30: 405-39, 1996). E1 and E2 are involved in the activation and transfer of ubiquitin, while the substrate specificity of the ubiquitin pathway is conferred by the E3 ubiquitin protein ligases. In some embodiments the agent comprises a ubiquitin protein ligase polypeptide. In some embodiments the agent is an E3 ubiquitin protein ligase polypeptide. In some embodiments the E3 ubiquitin protein ligase is an SCF polypeptide. In some embodiments the agent is a HECT polypeptide. In some embodiments the agent is a UBR1 polypeptide. In some embodiments the E3 ubiquitin protein ligase polypeptide is an F-box polypeptide (e.g., an F-box polypeptide which further comprises a WD domain). In some embodiments the F-box polypeptide is Cdc4p. In some embodiments the F-box polypeptide is Pop1p. In some embodiments the F-box polypeptide is Pop 2p. In some embodiments the F-box polypeptide is Grr1p. In some embodiments the F-box polypeptide is Met30p. In some embodiments the F-box polypeptide is HOSp. In some embodiments the F-box polypeptide is beta TrCPp. In some embodiments the F-box polypeptide is FWD1p. In some embodiments the F-box polypeptide is a polypeptide which is at least 70% identical to a contiguous polypeptide sequence of a polypeptide selected from the group consisting of SEQ ID Nos. 2, 4, 6, 8, 10, and 12 described in U.S. Pat. No. 7,223,556, which is incorporated herein by reference. In some embodiments the F-box polypeptide is at least 80% identical to a contiguous nucleic acid sequence of SEQ ID Nos. 1, 3, 5, 7, 9, and 11 described in U.S. Pat. No. 7,223,556, which is incorporated herein by reference.

In some embodiments the agent destabilizes RNA and/or proteins produced by the oncogene. In some embodiments an agent that destabilizes RNA is an agent that modulates nonsense-mediated RNA decay (NMD). Gardner discusses NMD implications for tumorigenesis (Gardner. Mol Cancer Res. 8; 295, 2010). In some embodiments an agent that modulates NMD is an agent that induces NMD of RNA transcripts of cognate oncogenic transcription factors, transcriptional coactivators, or chromatin regulators. In some embodiments an agent that modulates NMD is an agent that downregulates NMD that has been upregulated in a tumor. In some embodiments an agent that modulates NMD is an agent that inhibits Upf1. In some embodiments an agent that inhibits Upf1 is Pateamine A (PatA), as is described by Dang et al. (Dang et al. J Biol Chem. 284(35):23613-21, 2009).

In some embodiments the agent blocks mRNA splicing. In some embodiments an agent that blocks mRNA splicing interferes with alternative splicing. In some embodiments an agent that blocks mRNA splicing is a specific inhibitor of CDC2-like kinase isoforms 1 and 4 (CLK1/CLK4) known as KH-CB19, as is described in Fedorov et al. (Fedorov et al. Chem Biol. 18(1):67-76, 2011). In some embodiments an agent that interferes with alternative spicing is amiloride, as is described by Chang et al. PLos ONE. 6(6):e18643).

In some embodiments an agent that blocks mRNA splicing is an inhibitor of spliceosome catalysis. In some embodiments an agent that inhibits spliceosome catalysis is a 1,4-napthoquinones and/or a 1,4-heterocyclic quinone, non-limiting examples of which are described by Berg et al. (Berg et al. Mol Cell Biol. 32(7):1271-83, 2012). In some embodiments the splicing inhibitor comprises the benzothiazole-4,7-dione, BN82685, which blocks the second of two transesterification splicing reactions, preventing the release of intron lariat and exon ligation (Berg et al. 2012). In an embodiment an agent that blocks mRNA splicing comprises 4μ8C, which blocks substrate access to an IRE1 active site and selectively inactivates Xpb1 splicing, as is described by Cross et al. (Cross et al. Proc Natl Acad Sci USA, Epub ahead of print on Feb. 6, 2012).

In some embodiments the agent inhibits translation of mRNA into protein. In some embodiments an agent that inhibits translation of mRNA into protein comprises a nucleoside 5'-monophosphate analog of the mRNA 5'-cap, for example, Barzynkiewics et al. describe nucleotide cap analogs of 7-methylguanosine 5'monophosphate (m7GMP) that acted as competitive inhibitors of capped mRNA translation, including analogs in which the 7-methyl moiety is substituted with 7-ethyl (e7), 7-propyl (p7), 7-isopropyl (ip7), 7-butyl (b7), 7-isobutyl (ib7), 7-cyclopentyl (cp7), 7-(carboxymethyl) (cm7), 7-benzyle (bn7), 7-(2-phenylethyl) [7-(2-PhEt)], and 7-(1-penylethyl) [7-(1-PhEt)]. (Darzynkiewics et al. 28(11):4771-8, 1989).

It should be appreciated that the various agents described herein can be used alone, or in combination with other agents described, for example, an agent that interferes with c-Myc enhancer-driven transcription of a plurality of Myc target genes as described in U.S. Application Ser. No. 61/621,897, the entirety of which is hereby incorporated by reference herein.

In some embodiments, an agent of the present invention is administered in combination with a cancer therapeutic agent. It should be appreciated that the combined administration of an agent of the present invention and a cancer therapeutic agent can be achieved by formulating the cancer therapeutic agent and agent in the same composition or by administering the cancer therapeutic agent and agent separately (e.g., before, after, or interspersed with doses or administration of the cancer therapeutic agent). In some embodiments, an agent of the present invention is administered to a patient undergoing conventional chemotherapy and/or radiotherapy. In some embodiments the cancer therapeutic agent is a chemotherapeutic agent. In some embodiments the cancer therapeutic agent is an immunotherapeutic agent. In some embodiments the cancer therapeutic agent is a radiotherapeutic agent.

Exemplary chemotherapeutic agents that can be administered in combination with the agents of the present invention (e.g., agents that disrupt the function of super-enhancers) include alkylating agents (e.g. cisplatin, carboplatin, oxaloplatin, mechlorethamine, cyclophosphamide, chorambucil, nitrosureas); anti-metabolites (e.g. methotrexate, pemetrexed, 6-mercaptopurine, dacarbazine, fludarabine, 5-fluorouracil, arabinosycytosine, capecitabine, gemcitabine, decitabine); plant alkaloids and terpenoids including vinca alkaloids (e.g. vincristine, vinblastine, vinorelbine), podophyllotoxin (e.g. etoposide, teniposide), taxanes (e.g. paclitaxel, docetaxel); topoisomerase inhibitors (e.g. notecan, topotecan, amasacrine, etoposide phosphate); antitumor antibiotics (dactinomycin, doxorubicin, epirubicin, and bleomycin); ribonucleotides reductase inhibitors; antimicrotubules agents; and retinoids. (See, e.g., Cancer: Principles and Practice of Oncology (V. T. DeVita, et al., eds., J.B. Lippincott Company, 9$^{th}$ ed., 2011; Brunton, L., et al. (eds.) Goodman and Gilman's The Pharmacological Basis of Therapeutics, 12$^{th}$ Ed., McGraw Hill, 2010).

Exemplary immunotherapeutic agents include cytokines, such as, for example interleukin-1 (IL-I), IL-2, IL-4, IL-5, IL-13, IL-7, IL-10, IL-12, IL-15, IL-18, CSF-GM, CSF-G, IFN-γ, IFN-α, TNF, TGF-β but not limited thereto.

In some embodiments an agent of the present invention can be linked or conjugated to a delivery vehicle, which may also contain cancer therapeutic. Suitable delivery vehicles include liposomes (Hughes et al. Cancer Res 49(22):6214-20, 1989, which is hereby incorporated by reference in its entirety), nanoparticles (Farokhzad et al. Proc Nat'l Acad Sci USA 103(16):6315-20, 2006, which is hereby incorporated by reference in its entirety), biodegradable microspheres, microparticles, and collagen minipellets. The delivery vehicle can contain any of the agents and/or compositions of the present invention, as well as chemotherapeutic, radiotherapeutic, or immunotherapeutic agents described supra.

In some embodiments an agent of the present invention can be conjugated to a liposome delivery vehicle (Sofou and Sgouros, Exp Opin Drug Deliv. 5(2):189-204, 2008, which is hereby incorporated by reference in its entirety). Liposomes are vesicles comprised of one or more concentrically ordered lipid bilayers which encapsulate an aqueous phase. Suitable liposomal delivery vehicles are apparent to those skilled in the art. Different types of liposomes can be prepared according to Bangham et al. J. Mol. Biol. 13:238-52, 1965; U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

These liposomes can be produced such that they contain, in addition to the therapeutic agents of the present invention, other therapeutic agents, such as immunotherapeutic cytokines, which would then be released at the target site (e.g., Wolff et al., Biochim. Biophys. Acta. 802:259-73, 1984, which is hereby incorporated by reference in its entirety).

The present invention also contemplates a composition comprising an agent of the present invention and a pharmaceutically acceptable carrier, diluent, or excipient. Therapeutic formulations of the agents of the present invention can be prepared having the desired degree of purity with optional pharmaceutically acceptable carriers, excipients or stabilizers (REMINGTON'S PHARMACEUTICAL SCIENCES (A. Osol ed. 1980), which is hereby incorporated by reference in its entirety), in the form of lyophilized formulations or aqueous solutions. Acceptable carriers, excipients, or stabilizers are nontoxic to recipients at the dosages and concentrations employed, and include buffers such as acetate, Trisphosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG).

The active therapeutic ingredients of the pharmaceutical compositions alone or in combination with or linked to a cancer therapeutic agent or radiotherapeutic agent) can be entrapped in microcapsules prepared using coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in REMINGTON'S PHARMACEUTICAL SCIENCES (A. Osol ed. 1980), which is hereby incorporated by reference in its entirety. In some embodiments the agents of the present invention can be conjugated to the microcapsule delivery vehicle to target the delivery of the therapeutic agent to the site of the cells exhibiting super-enhancer associated oncogenes.

Sustained-release preparations may be prepared. Suitable examples of sustained-release preparations include semi-permeable matrices of solid hydrophobic polymers containing the antibody or polypeptide, which matrices are in the form of shaped articles, e.g., films or microcapsules. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

In some embodiments, an agent of the present invention can be provided with an enteric coating or otherwise protected from hydrolysis or low stomach pH. The therapeutically effective compositions containing the agents of the present invention are administered to a subject, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes.

Other therapeutic regimens may be combined with the administration of the agents of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect. In some embodiments, a composition of the present invention is administered in combination with a therapy selected from the group consisting of chemotherapy, radiotherapy, proton therapy, surgery, and combinations thereof.

The composition can include any number of additional active ingredients which can act in concert to provide a therapeutic effect, (e.g., a synergistic therapeutic effect), such as a chemotherapeutic agent, a radiotherapeutic agent, a nutritional supplement (e.g. vitamins), an antioxidant, and combinations thereof.

An "effective amount" or "effective dose" of an agent (or composition containing such agent) generally refers to the amount sufficient to achieve a desired biological and/or pharmacological effect, e.g., when contacted with a cell in vitro or administered to a subject according to a selected administration form, route, and/or schedule. As will be appreciated by those of ordinary skill in the art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. It will be understood that agents, compounds, and compositions herein may be employed in an amount effective to achieve a desired biological and/or therapeutic effect.

In certain aspects, the present invention relates to a method of treating a proliferative disorder in a patient in need of such treatment, said proliferative disorder characterized by an oncogene-associated super-enhancer occupied by more Mediator or BRD4 than an average single enhancer, comprising administering to the patient an effective amount of an agent that disrupts the function of the oncogene-associated super-enhancer, thereby selectively inhibiting proliferation of the oncogene in the patient.

It should be apparent to those skilled in the art that any of the compounds or agents described above can be employed in the method of treating the proliferative disorder to achieve the desired result of disrupting the function of the super-enhancer. The present invention contemplates the treatment of any proliferative disorder (e.g., cancer) that is characterized by an oncogene-associated super-enhancer. In some embodiments, the proliferative disorder to be treated is a hematological malignancy. In some embodiments, the proliferative disorder to be treated is selected from the group consisting of acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma. In some embodiments, the proliferative disorder is a non-hematological malignancy.

In certain exemplary embodiments, the agent is a BRD4 inhibitor, for example, small molecule JQ1 or iBET.

In some aspects, the present invention relates to a method of treating multiple myeloma involving an IGH-MYC locus that results in aberrant expression of oncogene c-Myc, comprising administering to a patient in need of such treatment an effective amount of an agent that decreases occupancy levels of BRD4 and MED1 at a super-enhancer associated with the IGH-MYC locus, wherein decreased occupancy levels of BRD4 and MED1 at the super-enhancer disrupt function of the super-enhancer thereby decreasing aberrant expression of oncogene c-Myc such that the multiple myeloma is treated. In some embodiments, the agent is a BRD4 inhibitor, for example, JQ1 or iBET.

In some aspects, the present invention relates to a method of identifying an agent that disrupts a super-enhancer associated with a gene, comprising: (a) providing a cell or cell free system comprising a super-enhancer, or functional fragment and/or variant thereof, and an associated gene, e.g., a reporter gene; (b) contacting the cell with a test agent, e.g., under conditions suitable for the super-enhancer to drive expression of the associated gene, e.g., to drive expression at a preselected level, e.g., a high level; (c) and measuring the level of expression of the associated gene.

In an embodiment decreased expression of the associated gene in the presence of the test agent indicates that the test agent is as an agent that disrupts the super-enhancer associated with the gene.

In an embodiment the method comprises transfecting a cell with a super-enhancer and the associated gene under conditions suitable for the super-enhancer to drive high levels of expression of the associated gene.

In an embodiment the method comprises comparing the level of expression with a reference, e.g., expression in a similar system not contacted with the test agent.

In an embodiment the method comprises confirming disruption of the super-enhancer, or functional fragment and/or variant thereof, e.g., by analysis of the presence of one or more super-enhancer component.

In an embodiment the method is first performed in a cell-free system and repeated in cell preparation, e.g., a cultured cell.

In an embodiment the method is first performed in a cell-free system or a cell preparation, e.g., a cultured cell, and repeated in an animal.

In an embodiment the super-enhancer is associated with a gene that is expressed in a disease state cell, e.g., a cancer cell.

In an embodiment the method comprises memorializing the results.

A wide variety of test agents can be used in the methods. For example, a test agent can be a small molecule, polypeptide, peptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multwell plates. They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see https://mli.nih.gov/mli/). The NIH Clinical Collection (NCC) is a plated array of approximately 450 small molecules that have a history of use in human clinical trials. These compounds are highly drug-like with known safety profiles. The NCC collection is arrayed in six 96-well plates. 50 µl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test agent may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or antihormonal drug, etc. In some embodiments, a compound is one that has undergone at least some preclinical or clinical development or has been determined or predicted to have "drug-like" properties. For example, the test agent may have completed a Phase I trial or at least a preclinical study in non-human animals and shown evidence of safety and tolerability. In some embodiments, a test agent is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant adverse effect on cell viability and/or proliferation, or the reduction in viability or proliferation can be no more than 1%, 5%, or 10% in various embodiments.

In various embodiments of any aspect herein pertaining to screening methods (e.g., methods of identifying agents), the screen may be performed using a single test agent or multiple test agents in a given reaction vessel. In various embodiments the number of reaction vessels and/or test agents is at least 10; 100; 1000; 10,000; 100,000; or more. In some embodiments of any aspect herein pertaining at least in part to screening methods (e.g., methods of identifying agents) a high throughput screen (HTS) is performed. High throughput screens often involve testing large numbers of test agents with high efficiency, e.g., in parallel. For example, tens or hundreds of thousands of agents may be routinely screened in short periods of time, e.g., hours to days. Such screening is often performed in multiwell plates (sometimes referred to as microwell or microtiter plates or microplates) containing, e.g., 96, 384, 1536, 3456, or more wells or other vessels in which multiple physically separated depressions, wells, cavities, or areas (collectively "wells") are present in or on a substrate. Different test agent(s) may be present in or added to the different wells. It will be understood that some wells may be empty, may comprise replicates, or may contain control agents or vehicle. High throughput screens may involve use of automation, e.g., for liquid handling, imaging, and/or data acquisition or processing, etc. In some embodiments an integrated robot system comprising one or more robots transports assay-microplates from station to station for, e.g., addition, mixing, and/or incubation of assay constituents (e.g., test agent, target, substrate) and, in some embodiments, readout or detection. A HTS system may prepare, incubate, and analyze many plates simultaneously. Certain general principles and techniques that may be applied in embodiments of a HTS are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser. Test agent(s) showing an activity of interest (sometimes termed "hits") may be retested and/or, optionally (e.g., depending at least in part on results of retesting) selected for further testing, development, or use. In some embodiments one or more structural analogs of a hit is synthesized. Such analogs may, for example, comprise substitution of one or more functional groups or heteroatoms present in the hit by a different functional group or heteroatom or substituting a heteroatom or functional group present in place of a hydrogen in the hit, etc. In some embodiments one or more such analog(s) are then tested for a property or activity of interest (e.g., ability to disrupt a super-enhancer associated with an oncogene or disease related gene).

Positive and/or negative controls may be used in any of the screens. An appropriate positive or negative control can be selected based at least in part on the assay. A negative control may be to perform the assay in the absence of a test agent.

In some embodiments, information derived from sequence analysis, mutational analysis, and/or structural analysis is used in the identification of a modulator, e.g., an agent that interferes with transcriptional coactivator or BRD4 co-occupancy of super-enhancers and active transcription start sites. For example, in some embodiments a structure (e.g., a two-dimensional or three-dimensional structure) of a target, e.g., a TF, generated at least in part using, e.g., nuclear magnetic resonance, homology modeling, and/or X-ray crystallography is used. In some embodiments a structure obtained with a ligand (e.g., an inhibitor) bound to the target may be used. In some embodiments a computer-aided computational approach sometimes referred to as "virtual screening" is used in the identification of candidate modulators. Structures of compounds, e.g., small molecules may be screened for ability to bind to a region (e.g., a "pocket") accessible to the compound. The region may be any region accessible to the compound, e.g., a concave region on the surface or a cleft or a region involved in dimerization. A variety of docking and pharmacophore-based algorithms are known in the art, and computer programs implementing such algorithms are available. Commonly used programs include Gold, Dock, Glide, FlexX, Fred, and LigandFit (including the most recent releases thereof). See, e.g., Ghosh, S., et al., Current Opinion in Chemical Biology, 10(3): 194-2-2, 2006; McInnes C., Current Opinion in Chemical Biology; 11(5): 494-502, 2007, and references in either of the foregoing articles, which are incorporated herein by reference. In some embodiments a virtual screening algorithm may involve two major phases: searching (also called "docking") and scoring. During the first phase, the program automatically generates a set of candidate complexes of two molecules (test compound and target molecule) and determines the energy of interaction of the candidate complexes. The scoring phase assigns scores to the candidate complexes and selects a structure that displays favorable interactions based at least in part on the energy. To perform virtual screening, this process may be repeated with a large number of test compounds to identify those that, for example, display the most favorable interactions with the target. In some embodiments, low-energy binding modes of a small molecule within an active site or possible active site or other target region are identified. In some embodiments a compound capable of docking at a site where mutations are known to inhibit activity of the target is identified. Variations may include the use of rigid or flexible docking algorithms and/or including the potential binding of water molecules. In some embodiments the three-dimensional structure of an enzyme's active site may be used to identify potential inhibitors. Agent(s) that have the potential to bind in or near an active site may be identified. These predictions may then be tested using the actual compound. A new inhibitor thus identified may then be used to obtain a structure of the enzyme in an inhibitor/enzyme complex to show how the molecule is binding to the active site. Further changes may be made to the inhibitor, e.g., to try to improve binding. This cycle may be repeated until an inhibitor of sufficient predicted or actual potency (e.g., a desired potency for therapeutic purposes) is identified. Numerous small molecule structures are available and can be used for virtual screening. A collection of compound structures may sometimes referred to as a "virtual library". For example, ZINC is a publicly available database containing structures of millions of commercially available compounds that can be used for virtual screening (http://zinc.docking.org/; Shoichet, J. Chem. Inf. Model., 45(1):177-82, 2005). A database containing about 250,000 small molecule structures is available on the National Cancer Institute (U.S.) website (at http://129.43.27.140/ncidb2/). In some embodiments multiple small molecules may be screened, e.g., up to 50,000; 100,000; 250,000; 500,000, or up to 1 million, 2 million, 5 million, 10 million, or more. Compounds can be scored and, optionally, ranked by their potential to bind to a target. Compounds identified in virtual screens can be tested in cell-free or cell-based assays or in animal models to confirm their ability to inhibit activity of a target molecule, their ability to activate a target molecule, and/or to assess their biological and/or pharmacological activity. Computational approaches may be used to predict one or more physicochemical, pharmacokinetic and/or pharmacodynamic properties of compounds identified in a physical or virtual screen. Such information may be used, e.g., to select one or more hits for, e.g., further testing, development, or use. For example, small molecules having characteristics typical of "drug-like" molecules may be selected and/or small molecules having one or more undesired characteristics may be avoided.

In some aspects of any screening and/or characterization methods, test agents are contacted with test cells (and optionally control cells) or used in cell-free assays at a predetermined concentration. In some embodiment the concentration is about up to 1 nM. In some embodiments the concentration is between about 1 nM and about 100 nM. In some embodiments the concentration is between about 100 nM and about 10 µM. In some embodiments the concentration is at or above 10 µM e.g., between 10 µM and 100 µM. Following incubation for an appropriate time, optionally a predetermined time, the effect of compounds or composition on a parameter of interest in the test cells is determined by an appropriate method known to one of ordinary skill in the art, e.g., as described herein. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously. If desired, the compound can be removed prior to assessing the effect on the cells.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Master Transcription Factors and Mediator Establish Super-Enhancers at Key Cell Identity Genes Introduction Transcription factors typically regulate gene expression by binding cis-acting regulatory elements known as enhancers and recruiting coactivators and RNA Polymerase II (RNA Pol II) to target genes (Ong and Corces, 2011), Transcription factor-bound enhancers interact with target gene promoters via DNA looping events facilitated by the Mediator co-activator complex and cohesin (Kagey et al., 2010). Between 400,000 and 1.4 million putative enhancers have been identified in the mammalian genome (Bernstein et al., 2012; Thurman et al., 2012). In any one cell type, the number of active enhancers is estimated to be in the thousands and enhancer activity is largely cell-type specific (Bernstein et al., 2012; Shen et al., 2012; Yip et al., 2012). Whereas most genes are transcriptionally active in multiple cell types, enhancers tend to be active only in specific lineages (Shen et al., 2012). These data suggest that much of the transcriptional control of mammalian development is due to the diverse activity of enhancers that control cell type specific patterns of gene expression.

In embryonic stem cells (ESCs), control of the gene expression program that establishes and maintains ESC state is dependent on a remarkably small number of master transcription factors (Young, 2011). These transcription factors, which include Oct4, Sox2 and Nanog (OSN), bind to approximately 7,000 enhancers together with the Mediator coactivator complex (Kagey et al., 2010). The Mediator complex facilitates the ability of enhancer-bound transcription factors to recruit RNA Pol II to the promoters of target genes (Malik and Roeder, 2010) and is essential for maintenance of ESC state and early embryonic development (Kagey et al., 2010). Reduced levels of either Oct4 or Mediator have a very similar effect on the ESC gene expression program and cause the same rapid loss of ESC identity (Kagey et al., 2010).

It is striking that ESC maintenance is highly sensitive to perturbations in the levels of Mediator (Kagey et al., 2010). To understand the reasons underlying this hypersensitivity, we investigated enhancers bound by Mediator in these cells. We identified approximately 200 genomic regions that contained tightly spaced clusters of enhancers spanning extraordinarily large domains. These "super-enhancers" were occupied by an order of magnitude more Mediator than the average enhancer, and were associated with the key cell-type specific ESC genes. These enhancers also conferred stronger enhancer activity relative to the average enhancer, suggesting these elements drive gene expression programs and cell state. During ESC differentiation, the ESC super-enhancers were rapidly lost and new super-enhancers were formed at genes key to the differentiated cell type. Additional cell types were found to have super-enhancers associated with highly expressed and cell-type specific genes. These results argue that super-enhancers drive genes essential for cell identity in multiple cell types and that these elements are especially sensitive to perturbations involved in dynamic changes in cell state.

Results

Large Genomic Domains Occupied by Mediator in ESCs

Previous studies have shown that co-occupancy of sites by the Oct4, Sox2 and Nanog transcription factors is highly predictive of enhancer activity (Chen et al., 2008). We generated ChIP-Seq data for Oct4, Sox2, Nanog (OSN) in murine ESCs and identified 6,343 regions that were bound by all three transcription factors. The Mediator co-activator complex has been previously shown to interact with the enhancer-bound transcription factors and facilitate recruitment of the transcription apparatus to active gene promoters (Malik and Roeder, 2010). Analysis of the 6,343 OSN regions confirmed the presence of Mediator, including regions surrounding the Klf4 gene (FIG. 1A). Therefore, we defined the 6,343 regions bound by OSN as ESC enhancers.

Closer inspection of the 6,343 ESC enhancers revealed a surprising feature: some ESC enhancers are occupied by extremely high levels of Mediator (FIG. 1B). Global analysis of the 6,343 ESC enhancers confirmed the distribution of Mediator occupancy across this set of regions is not evenly distributed (FIG. 1C). Instead, there is a distribution of occupancy that indicates these regions fall into two distinct classes, with one class containing an exceptional amount of Mediator proteins (FIG. 1C). Further analysis of this small subset (211) of regions revealed that, on average, they contained 27 times more Mediator proteins compared to the remaining 6,132 enhancers (FIG. 1D). Additionally, on average these regions covered larger genomic distances (5.2 kb) compared to the remaining enhancers (469 bp) (FIG. 1D). Thus, these ~200 regions, which we call "super-enhancers", are occupied by at least an order of magnitude more Mediator relative to the mean, and typically span DNA domains at least an order of magnitude larger.

Many genome wide enhancer mapping efforts utilize histone marks and regulatory proteins as surrogates for enhancers (Bernstein et al., 2012; Shen et al., 2012). Further characterization of the super-enhancers revealed that these regions are also occupied by other enhancer-associated modifications and proteins, including H3K27ac, a histone modification commonly found at enhancers and used to predict regions of enhancers activity (Creyghton et al., 2010; Rada-Iglesias et al., 2011). Interestingly, H3K27Ac failed to reveal the striking disparity noted for OSN-Mediator bound super-enhancers. Thus, Mediator ChIP-Seq data is superior to surrogate data from histone modifications for identifying super-enhancers in ESCs.

Super-enhancers are Associated with Key ESC Genes

Most studies have assigned enhancers to putative target genes by using the proximity of enhancers and target genes. Recent work has identified topological domains associated with transcriptional control in the ESC genome using high throughputs chromatin conformation capture data (Hi-C) (Dixon et al., 2012). We therefore used proximity of enhancer elements and genes to facilitate mapping of ESC enhancers to promoters, and further used Hi-C to additionally assign enhancers to promoters of genes that were greater than 40 kb away. Previous studies using chromatin configuration capture (3C) have shown that, at an enhancer element brought into close proximity to a promoter region by DNA looping, the Mediator ChIP-Seq signals are similar at both regions (Kagey et al., 2010). We therefore required that enhancer-promoter interaction candidates have similar levels of Mediator. The assignments of super-enhancers to promoters identified 192 genes, with a further ~5,300 assigned by Hi-C. For three of these genes, the proximity between portions of the super-enhancer and the target promoter were previously established using 3C (Kagey et al., 2010).

Figure 2A:
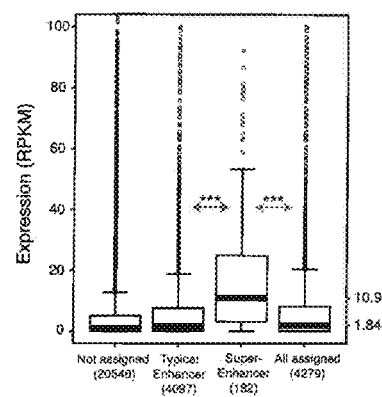
FIGS. 2A, 2B, 2C and 2D demonstrate that Super-enhancers drive key pluripotency genes.
Figure 2B:
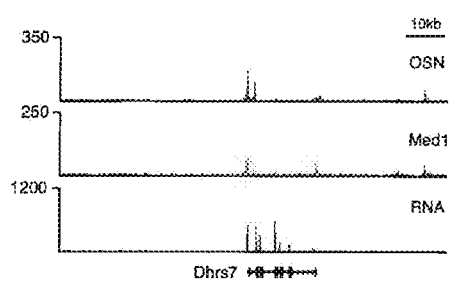
Figure 2C:
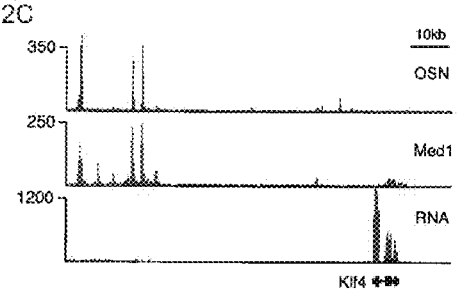

A global RNA sequencing (RNA-Seq) analysis of the genes assigned to ESC enhancers confirmed that these genes were expressed at very high levels compared to other genes in ESCs (FIG. 2A). Further examination of this set of genes, however, revealed a striking difference: the super-enhancer-associated genes were expressed at higher levels compared to those neighboring the remaining enhancers (FIG. 2B,C). Compared to the average expression levels of genes near the median enhancer (1.84 RPKM), genes associated with super-enhancers were expressed 6-times higher (FIG. 2A). These results suggest super-enhancers are associated with the most highly expressed genes compared to other enhancers.

Figure 2D:
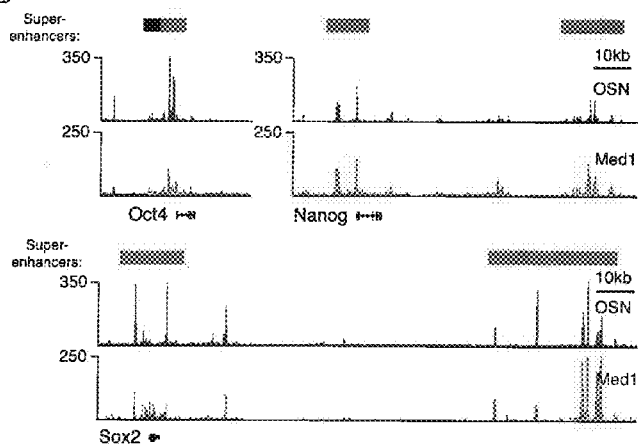

We next determined if these highly expressed genes were important for ESC identity. In contrast to the other highly expressed genes that were found near the 6,132 enhancers, including house-keeping genes, super-enhancer-associated genes are critical for ESC maintenance and reprogramming. Super-enhancers were directly associated with many genes previously shown to play important roles in ESC identity, including Esrrb (Ivanova et al., 2006; Zhang et al., 2008); Tbx3 (Ivanova et al., 2006; Niwa et al., 2009); and the mir290-295 microRNA gene cluster (Lichner et al., 2011; Marson et al., 2008; Zovoilis et al., 2009). Remarkably, the super-enhancer-associated genes included those encoding the ESC master transcription factors Oct4, Sox2 and Nanog (FIG. 2D). These three transcription factors are known to auto-regulate their expression through promoter binding, forming an interconnected auto-regulatory loop. This form of auto-regulation is a core feature of the ESC transcriptional regulatory circuitry (Boyer et al., 2005), whose establishment is likely key to reprogramming of various cells into iPS cells (Jaenisch and Young, 2008). Small portions of the super-enhancers associated with these genes have previously been shown to have enhancer activity in reporter assays (Chen et al., 2008) and to participate in enhancer-promoter looping at the Oct4 and Nanog genes (Kagey et al., 2010). Thus, the genes encoding the master transcription factors are themselves under the control of super-enhancers. Overall these results support a model that super-enhancers associate with highly expressed and highly cell-type specific genes that include key drivers of ESC identity.

Super-Enhancers Confer Strong Enhancer Activity

Figure 3A:
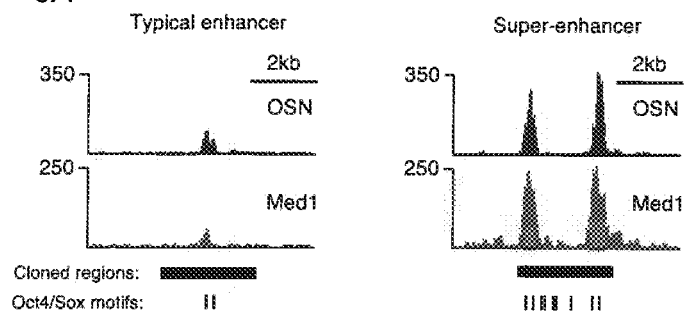
FIGS. 3A, 3B and 3C demonstrate that super-enhancers confer high enhancer activity.
Figure 3B:
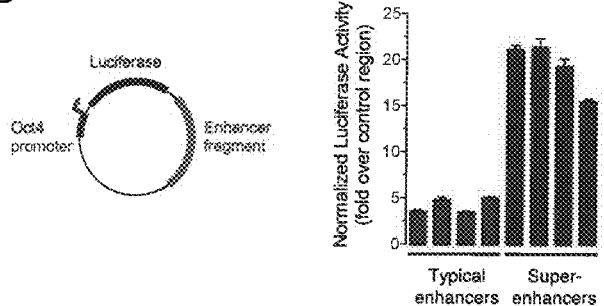
Figure 3C:
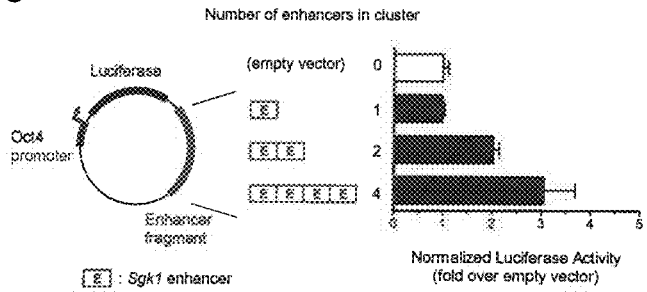

One striking feature of the super-enhancers is that they contain multiple, highly enriched regions of Mediator compared to average enhancers that typically consist of a single peak of the coactivator (FIG. 3A). DNA sequence analysis confirmed that super-enhancers contained more OSN binding motifs than do median enhancers (FIG. 3A). To test whether these super-enhancers confer stronger enhancer activity than median enhancers, we cloned 3 kb regions of super-enhancers and median enhancers into luciferase reporter constructs that were subsequently transfected into ESCs. We found that on average, super-enhancers drove 16 times more luciferase expression than median enhancers (FIG. 3B). Since a super-enhancer contained more Mediator occupancy compared to a median enhancer, these results suggested that clusters of enhancers may display higher enhancer activity in ESCs. To test this model, we generated an artificial super-enhancer by oligomerizing the distal median enhancer of the Sgk1 gene. As a single median enhancer, this region displayed low luciferase activity (FIG. 3B). Remarkably, the dimeric Sgk1 enhancer exhibited 2-times higher activity, while the tetrameric Sgk1 enhancer exhibited 3-times higher enhancer activity compared to the single Sgk1 enhancer driving luciferase expression in ESCs (FIG. 3C). These results suggest that super-enhancers can be formed by clusters of enhancers, that they have higher activity than median enhancers, and are sufficient to drive high expression of key, cell type-specific genes required to maintain ESC identity.

Rapid Loss of ESC Super-enhancers During ESC Differentiation

Figure 4A:
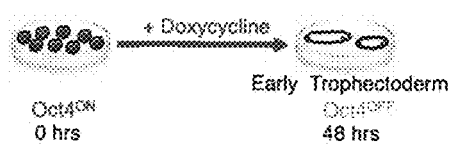
FIGS. 4A and 4B demonstrate rapid loss of ESC super-enhancers and establishment of new super-enhancers during ESC differentiation.

If super-enhancers play key roles in transcriptional control of cell identity, then differentiation of ESCs should lead to loss of ESC super-enhancers. To test this notion, we stimulated ESCs to differentiate into a trophectoderm lineage by shutting down Oct4 transcription (FIG. 4A)(Niwa et al., 2000). Loss of Oct4 results in cellular differentiation, loss of expression of Oct4 target genes, and upregulation of the trophectoderm master regulator transcription factor Cdx2 (Deb et al., 2006; Niwa et al., 2005; Strumpf et al., 2005; Wang et al., 2010).

Figure 4B:
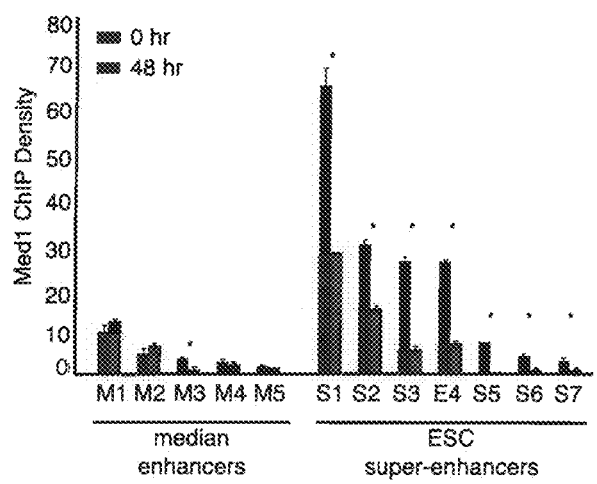

The fate of ESC super-enhancers during differentiation was examined by profiling global levels of Mediator using ChIP-PCR (FIG. 4B). All seven of the super-enhancers tested that were occupied by OSN and Mediator in ESCs had at least two-fold lower levels of Mediator proteins upon differentiation (FIG. 4B). On average, the tested super-enhancers had 68% lower levels of Mediator upon ESC differentiation compared to control ESCs (FIG. 4B). This included the super-enhancers to the key ESC genes Oct4/Pot5f1 and Sox2 (FIG. 4B). In contrast, four of the five typical enhancers that were tested retained high levels of Mediator compared to super-enhancers upon ESC differentiation (FIG. 4B). Surprisingly, only one of the typical enhancers tested had at least two-fold lower levels of Mediator upon differentiation (FIG. 4B). On average, median enhancers had only 14% lower levels of Mediator upon differentiation compared to control ESCs (FIG. 4B). Together, these results are consistent with the model that super-enhancers play key roles in establishing and maintaining cell state, and that these enhancer elements are sensitive to perturbations that accompany the dynamic changes in cell state during differentiation.

Super-Enhancers are Found in Multiple Cell Types and are Cell-Type Specific

The identification of both ESC and trophectoderm lineage super-enhancers suggest that super-enhancers may be a common feature of mammalian cells. Accordingly, in any given cell type, super-enhancer associated genes are likely to play prominent roles in establishing and maintaining cell identity.

Further, the pattern of super-enhancers in any given cell type is likely to be cell-type specific.

Figures 5A, 5B, 5C, 5D, 5E:
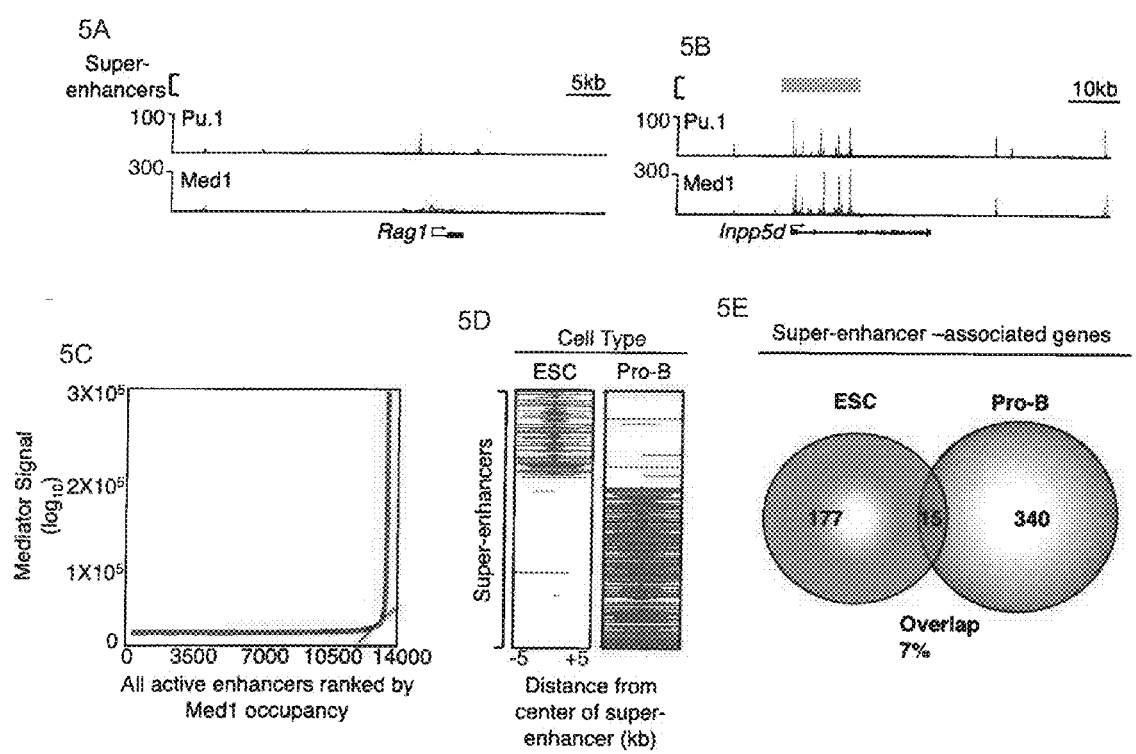
FIGS. 5A, 5B, 5C, 5D and 5E demonstrate that super-enhancers are a general feature of mammalian cells and are cell-type specific.

To test these predictions, we profiled Mediator levels and master transcription factor Pu.1 in pro-B cells using ChIP-Seq. Mediator occupancy highly correlated with occupancy of Pu.1 at promoter distal sites (FIG. 5A, B). Of the 13,303 sites bound by Pu.1 in pro-B cells, 79% were co-occupied by Mediator. Using similar criteria as in ESCs, 392 super-enhancers were identified in pro-B cells, and exhibited extremely high levels of Mediator occupancy (FIG. 5B,C). On average, the pro-B super-enhancers contained 31 times more Mediator proteins compared to the remaining 12,911 enhancers, and covered larger genomic distances (15.4 kb) compared to the remaining enhancers (422 bp). These findings support the conclusion that super-enhancers are a general feature of mammalian cells.

Genes associated with super-enhancers in pro-B cells were previously shown to be important for pro-B cell development, supporting the model that super-enhancers drive expression of target genes critical for cellular identity. Among the 355 super-enhancer-associated genes that are highly expressed in pro-B cells included many genes previously shown to play important roles in B cell development, including Pax5; Rag2; VpreB1 and VpreB2. We next determined if super-enhancers and their associated genes are cell-type specific by comparing ESC and pro-B cell super-enhancers and their target genes (FIG. 5D,E). The set of super-enhancers showed minimal overlap between ESCs and pro-B cells (FIG. 5D). Of the 211 ESC super-enhancers, only 9 regions (2%) overlapped with the pro-B cell super-enhancers (FIG. 5D). Furthermore, the super-enhancer-associated genes exhibited highly cell-type specific patterns of expression (FIG. 5D). Of the 192 genes neighboring super-enhancers in ESCs, only 15 (8%) were associated with super-enhancers in pro-B cells (FIG. 5E). These results suggest that super-enhancers are likely to be a general feature of most cell types and are likely to drive the expression of genes controlling cellular identity.

Discussion

We have identified in multiple cell types the existence of super-enhancers. Super-enhancers are enhancers bound by master regulator transcription factors that contain disproportionately high levels of the Mediator co-activator complex. Mediator levels are likely to be rate limiting for enhancer mediated transcription and as such, the disparity in Mediator levels at super-enhancers potentially represents an important hierarchical stratification of enhancers. Indeed, in multiple cell types, super-enhancers associate with known genes essential for cell identity and globally are likely to be the drivers of key cell identity controlling genes.

The observation of super-enhancers also suggests the complexity of cis-regulating elements can be significantly reduced. Although somewhere between hundreds of thousand and millions of enhancers are likely to exist in the mammalian genome, in any given cell type only a few hundred super-enhancers are likely to drive the expression of genes that establish cellular identity. In many cell types, small subsets of transcriptionally active genes have been identified through genetic screens as essential for cellular identity. However an analogous appreciation does not exist for enhancers in any given cell types. The characteristic features of super-enhancers strongly suggest that they may be among the most essential enhancers in any given cell type.

Lastly, the ability of super-enhancers to drive expression of key cell identity genes suggest that mutations to super-enhancers may potentially lead to disease and developmental defect. Indeed, recent evidence from the ENCODE consortium revealed that the majority of disease associated SNPs occur in regulatory regions (Bernstein et al., 2012; Schaub et al., 2012). It is easy to imagine that loss of a super-enhancer through genetic deletions could lead to developmental defects through the inability to fully establish cellular identity. Conversely, translocation of a super-enhancer could result in aberrant gene regulation. Example 2 below provides evidence that super-enhancers associate with key cancer dependency genes, including c-Myc via the translocated IgH super-enhancer in Multiple Myeloma.

The association of super-enhancers with key cell identity genes as well as cancer dependency genes argues that super-enhancers are important and essential components of cellular identity. Given super-enhancers reflect the occupancy of master regulator transcription factors in a given cell type, identification of super-enhancers in any cell type could potentially facilitate the mapping of the core transcriptional circuitry. In disease cells, super-enhancers have the potential to act as powerful biomarkers, identifiers of drug target candidates, and can potentially they themselves be drugged via targeting of Mediator and other enhancer bound components. More importantly, the characterization of super-enhancers implores a departure from a gene centric view of the genome, and instead supports an appreciation that regulatory control regions found in intergenic DNA may represent key features in the blueprints of mammalian development and disease.

REFERENCES

Bernstein, B. E., Birney, E., Dunham, I., Green, E. D., Gunter, C., and Snyder, M. (2012). An integrated encyclopedia of DNA elements in the human genome. Nature 489, 57-74.

Boyer, L. A., Lee, T. I., Cole, M. F., Johnstone, S. E., Levine, S. S., Zucker, J. P., Guenther, M. G., Kumar, R. M., Murray, fn., Jenner, R. G., et al. (2005). Core transcriptional regulatory circuitry in human embryonic stem cells, Cell 122, 947-956.

Creyghton, M. P., Cheng, A. W., Welstead, G. G., Kooistra, T., Carey, B. W., Steine, E. J., Hanna, J., Lodato, M. A., Frampton, G. M., Sharp, P. A., et al. (2010). Histone H3K27ac separates active from poised enhancers and predicts developmental state. Proc Natl Acad Sci USA 107, 21931-21936.

Deb, K., Sivaguru, M., Yong, H. Y., and Roberts, R. M, (2006). Cdx2 gene expression and trophectoderm lineage specification in mouse embryos. Science 311, 992-996.

Dixon, J. R., Selvaraj, S., Yue, F., Kim, A., Li, Y., Shen, Y., Hu, M., Liu, J. S., and Ren, B, (2012). Topological domains in mammalian genomes identified by analysis of chromatin interactions. Nature 485, 376-380.

Ivanova, N., Dobrin, R., Lu, R., Kotenko, I., Levorse, J., DeCoste, C., Schafer, X., Lun, Y., and Lemischka, I. R. (2006). Dissecting self-renewal in stem cells with RNA interference. Nature 442, 533-538.

Kagey, M. H Newman, J. J., Bilodeau, S., Zhan, Y., Orlando, D. A., van Berkum, N. L. Ebmeier, C. C., Goossens, J., Rahl, P. B., Levine, S. S., et al. (2010). Mediator and cohesin connect gene expression and chromatin architecture. Nature 467, 430-435.

Lichner, Z., Pall, E., Kerekes, A., Pallinger, E., Maraghechi, P., Bosze, Z., and Gocza, E. (2011). The miR-290-295 cluster promotes pluripotency maintenance by regulating cell cycle phase distribution in mouse embryonic stem cells. Differentiation 81, 11-24.

Malik, S., and Roeder, R. G. (2010). The metazoan Mediator co-activator complex as an integrative hub for transcriptional regulation. Nat Rev Genet 11, 761-772.

Marson, A., Levine, S. S., Cole, M. F., Frampton, G. M., Brambrink, T., Johnstone, S., Guenther, M. G., Johnston, W. K., Wernig, M., Newman, J., et al. (2008). Connecting microRNA genes to the core transcriptional regulatory circuitry of embryonic stem cells. Cell 134, 521-533.

Niwa, H., Miyazaki, J., and Smith, A. G. (2000). Quantitative expression of Oct-3/4 defines differentiation, dedifferentiation or self-renewal of ES cells. Nat Genet 24, 372-376.

Niwa, H., Ogawa, K., Shimosato, D., and Adachi, K. (2009). A parallel circuit of LIF signalling pathways maintains pluripotency of mouse ES cells. Nature 460, 118-122.

Niwa, H., Toyooka, Y., Shimosato, D., Strumpf, D., Takahashi, K., Yagi, R., and Rossant, J. (2005). Interaction between Oct3/4 and Cdx2 determines trophectoderm differentiation. Cell 123, 917-929.

Ong, C. T., and Corces, V. G. (2011). Enhancer function: new insights into the regulation of tissue-specific gene expression. Nat Rev Genet 12, 283-293.

Rada-Iglesias, A., Bajpai, R., Swigut, T., Brugmann, S A., Flynn, R. A., and Wysocka, J. (2011). A unique chromatin signature uncovers early developmental enhancers in humans. Nature 470, 279-283.

Schaub, M. A., Boyle, A. P., Kundaje, A., Batzoglou, S., and Snyder, M. (2012). Linking disease associations with regulatory information in the human genome. Genome Res 22, 1748-1759, Shen, Y., Yue, F., McCleary, D. F., Ye, Z., Edsall, L., Kuan, S., Wagner, U., Dixon, J., Lee, L., Lobanenkov, V. V., et al. (2012). A map of the cis-regulatory sequences in the mouse genome. Nature 488, 116-120.

Strumpf, D., Mao, C. A., Yamanaka, Y., Ralston, A., Chawengsaksophak, K., Beck, F., and Rossant, J. (2005). Cdx2 is required for correct cell fate specification and differentiation of trophectoderm in the mouse blastocyst. Development 132, 2093-2102.

Thurman, R. E., Rynes, E., Humbert, R., Vierstra, J., Maurano, M. T., Haugen, E., Sheffield, N. C., Stergachis, A. B., Wang, 1-L, Vernot, B., et al. (2012). The accessible chromatin landscape of the human genome. Nature 489, 75-82.

Wang, K., Sengupta, S., Magnani, L., Wilson, C. A., Henry, R. W., and Knott, J. G. (2010). Brg1 is required for Cdx2-mediated repression of Oct4 expression in mouse blastocysts. PLoS One 5, e10622.

Yip, K. Y., Cheng, C., Bhardwaj, N., Brown, J. B., Leng, J., Kundaje, A., Rozowsky, J., Birney, E., Bickel, P., Snyder, M., et al. (2012). Classification of human genomic regions based on experimentally determined binding sites of more than 100 transcription-related factors. Genome Biol 13, R48.

Young, R. A. (2011). Control of the embryonic stem cell state. Cell 144, 940-954. Zhang, X., Zhang, J., Wang, T., Esteban, M. A., and Pei, D. (2008). Esrrb activates Oct4 transcription and sustains self-renewal and pluripotency in embryonic stem cells. J Biol Chem 283, 35825-35833.

Zovoilis, A., Smorag, L., Pantazi, A., and Engel, W. (2009). Members of the miR-290 cluster modulate in vitro differentiation of mouse embryonic stem cells. Differentiation 78, 69-78.

Example 2

Selective Inhibition of Tumor Oncogenes by Disruption of Super-Enhancers

Introduction

Inhibitors of chromatin regulators are gaining interest as therapeutic agents for cancer because of their ability to specifically repress key oncogenic drivers in many tumor types. A major challenge in cancer therapeutics has been the direct pharmacologic inhibition of oncogenic transcription factors such as c-MYC. MYC is one of the most commonly amplified oncogenes in cancer, but lacks clear ligand-binding domains, rendering it difficult to target by small molecule inhibitors (Nair and Burley, 2003). However, several recent studies have shown that inhibition of chromatin regulators, such as the bromodomain protein BRD4, may represent an alternate avenue for selectively targeting these key oncogenic drivers. It is not yet known how inhibition of a general transcriptional regulator can exert a specific effect on a small number of genes. Understanding this concept will aid the development and selection of drugs in treating many cancers.

BRD4 was first identified as an interaction partner of the murine Mediator coactivator complex, and has subsequently been shown to associate with this transcription complex in a variety of human cells (Dawson et al., 2011; Jiang et al., 1998; Wu et al., 2003). BRD4 is also involved in the control of transcriptional elongation through its association with the positive transcription elongation factor, P-TEFb (Jang et al., 2005; Yang et al., 2005). In addition, bromodomain proteins can associate with specific acetylated histone residues, an interaction which can be disrupted by small molecules that competitively occupy the acetyl-lysing binding pockets in select members of this 61-member protein family (Filippakopoulos et al., 2012). Two recently developed bromodomain inhibitors, JQ1 and iBET, selectively bind to BRD4 (Filippakopoulos et al., 2010; Nicodeme et al., 2010). Despite this general role played in transcription regulation, inhibition of BRD4 by BET-inhibitors appears to have a highly selective effect on tumor cells (Dawson et al., 2011; Delmore et al., 2011; Mertz et al., 2011; Zuber et al., 2011). BET-inhibitors appear to cause dramatic suppression of the potent oncogene, MYC, and lead to a pronounced anti-proliferative effect in a range of tumors, including multiple myeloma (MM), Burkitt's lymphoma (BL), and acute myeloid leukemia (AML) (Dawson et al., 2011; Delmore et al., 2011; Mertz et al., 2011; Zuber et al., 2011). Although BRD4 inhibition shows great promise as a therapeutic agent in cancer, it remains unclear why inhibition of this general chromatin regulator has a selective effect on the MYC gene in these tumor cells.

To investigate this mechanism, we turned to concepts described Example 1 above. In that study, we demonstrated that transcriptional activators, such as the Mediator coactivator complex are not distributed evenly throughout the genome. Instead, we found that Mediator binding is concentrated at a discrete number of enhancer regions, which we have classified as super-enhancers. Our analysis of mouse embryonic stem cells (mESCs) revealed that these "super-enhancers" consist of enhancer clusters that span vast chromatin domains when compared to typical enhancer regions and are occupied by an order of magnitude more Mediator complex proteins. In addition, super-enhancers preferentially associate with and activate genes key to cell state.

Enhancers function through co-operative and synergistic interactions between multiple transcription factors and coactivators (Carey, 1998; Carey et al., 1990; Giese et al., 1995; Kim and Maniatis, 1997; Thanos and Maniatis, 1995). Cooperative binding and synergistic activation confer increased sensitivity, so that small changes in activator concentration can lead to dramatic changes in activator binding and transcription of associated genes (Carey, 1998). This led us to hypothesize that highly sensitive super-enhancers driving key oncogenic drivers in multiple myeloma may account for the selective effect of BRD4 inhibition.

In this study, we show that BRD4 inhibition has a highly selective effect on critical tumor genes associated with super-enhancers. As expected, given its role as a general regulator of transcriptional pause release and its association with the Mediator complex, we found that BRD4 was located at a majority of active enhancers and promoters in tumor cells. Strikingly, extreme levels of BRD4 were found at a small subset of enhancer regions, which we have termed super-enhancers. These regions are similar to the super-enhancers described in mouse embryonic stem cells as discussed in Example 1 above. We found that binding of BRD4 and Mediator at super-enhancers was hyper-sensitive to loss of BRD4 binding through BET inhibition. This in turn corresponded to a dramatic loss of transcription at super-enhancer associated genes, such as MYC. Our data suggest a model of how inhibitors of generally acting chromatin regulators can exert a gene-specific effect, through the disruption of heavily occupied, cooperatively bound sites functioning at highly expressed tumor regulators. This concept may improve our understanding of how these drugs should be selected for the treatment of genetically-defined cancers.

Results

Mediator and BRD4 Co-Occupy Promoters of Active Genes in Multiple Myeloma

Figure 6A:
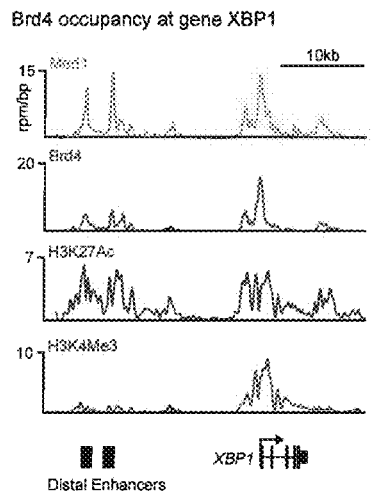
FIGS. 6A, 6B, 6C and 6D demonstrate that Mediator and BRD4 co-occupy promoters of active genes in multiple myeloma.
Figure 6B:
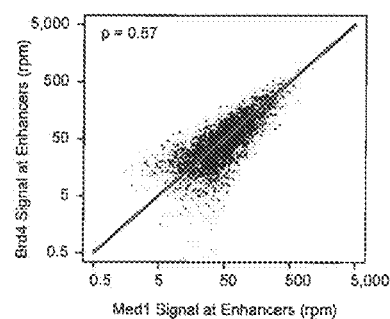
Figure 6C:
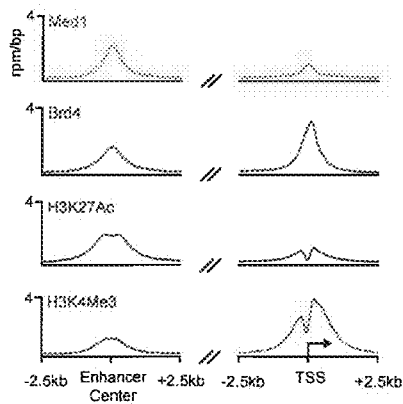
Figure 6D:
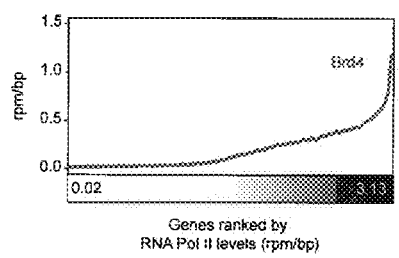

In Example 1 above it was shown that Mediator and BRD4 co-occupy enhancers and active transcription start sites in embryonic stem cells and in differentiated cells. To determine whether Mediator and BRD4 co-occupy these sites in multiple myeloma cells, we used chromatin immunoprecipitation coupled to high-throughput sequencing (ChIP-Seq) with antibodies directed against Mediator, Brd4 and various marks of enhancers and active transcription start sites in MM.1S cells (FIG. 6). The results, whether viewed by individual genes tracks or by meta-gene analysis, show that Mediator and BRD4 generally co-occupy enhancers and active transcription start sites (FIG. 6A, B). Signals for Mediator and BRD4 were found together with those for nucleosomes with the histone modification H3K27Ac in 8,000 regions lacking transcription start sites, and these were considered enhancers. Signals for BRD4 and Mediator were also found together with those for the histone modification H3K4me3 and RNA polymerase II at 14,000 annotated transcription start sites, and these were considered active transcription start sites. The levels of Mediator and BRD4 occupancy correlated with one another at both enhancers and transcription start sites (FIG. 6C), and the levels of BRD4 were correlated with the levels of RNA polymerase II at genes (FIG. 6D), consistent with the results observed in non-tumor cells in Example 1 above. These results indicate that Mediator and BRD4 generally co-occupy enhancers and active transcription start sites throughout the genome of MM.1S cells.

Super-Enhancers are Associated with Key Multiple Myeloma Genes

The sizes of enhancers identified by Mediator occupancy showed an unusual distribution, with a small subset of enhancers containing exceptional levels of Mediator protein (FIG. 7A). These 210 "super-enhancers" have features similar to those described in Example 1 above for mESCs (FIG. 7A). These are regions occupied, on average, by 16-fold more Mediator compared to normal enhancer regions. Super-enhancers also occupy larger genomic regions than normal enhancers, with a median size of 20 kb, 16-fold greater than the normal enhancer size of 1.3 kb. In addition to high Mediator occupancy, these enhancers were also bound by exceptional levels of BRD4, on average, 16-fold higher than normal enhancers (FIG. 7B).

As noted in Example 1 above, in ESCs and in differentiated cells, super-enhancers have exceptional transcription activation activity and are associated with highly expressed cell-type-specific genes that are located nearby. In MM.1S cells, super-enhancers were associated with highly expressed, cell-type specific genes, including genes known to be important in multiple myeloma (FIG. 7C). For example, the MM.1S MYC locus contains a chromosomal rearrangement that places MYC under the control of the IgH enhancers, which are highly active in the antibody producing plasma cells from which MM derives. The IgH-MYC locus contains a large, 40 kb super-enhancer, occupied by high levels of both BRD4 and MED1 (FIG. 7D). Super-enhancers were also found associated with the IRF4 gene (FIG. 7D), which encodes a key plasma cell transcription factor frequently deregulated in MM (Shaffer et al., 2008).

BRD4 Occupancy at Super-Enhancers is Highly Sensitive to Bromodomain Inhibition

Enhancers are formed through co-operative and synergistic binding of multiple transcription factors and coactivators (Carey, 1998; Carey et al., 1990; Giese et al., 1995; Kim and Maniatis, 1997; Thanos and Maniatis, 1995). As a consequence of this binding behavior, enhancers bound by many cooperatively-interacting factors lose activity more rapidly than enhancers bound by fewer factors when the levels of enhancer-bound factors are reduced (Giniger and Ptashne, 1988; Griggs and Johnston, 1991). The presence of super-enhancers at MYC and other key genes associated with multiple myeloma led us to consider the hypothesis that super-enhancers are more sensitive to reduced levels of BRD4 than average enhancers. If super-enhancers are more sensitive to reduced levels of BRD4 than average enhancers, then super-enhancers should experience greater loss of BRD4 than average enhancers, and genes associated with super-enhancers might then experience a greater reduction of transcription than genes with average enhancers.

To test this hypothesis, we first examined the effects of various concentrations of JQ1 on genome-wide on BRD4 occupancy (FIG. 8A). During the course of the 6 hour treatments, JQ1 had little effect on MM1.S cell viability, as measured by ATP levels, while at later time points, JQ1 had a dramatic antiproliferative effect (FIG. 8B). As expected, MYC protein levels were significantly depleted by JQ1 treatment (FIG. 8C)(Delmore et al., 2011). In contrast, JQ1 did not affect BRD4 protein levels within cells, and did not significantly reduce ChIP efficiency (FIG. 8D), However, super-enhancers showed a greater loss of BRD4 occupancy when compared to regions with average or low amounts of BRD4 (FIG. 8E). The IgH enhancer was among those super-enhancers that showed significantly greater loss of BRD4 than typical enhancer regions with lower BRD4 occupancy, such as CD28 (FIG. 8G).

Loss of P-TEFb Accompanies BRD4 Inhibition

Figure 9A:
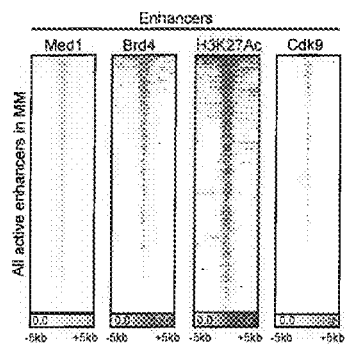
FIGS. 9A, 9B and 9C demonstrate that the loss of P-TEFb accompanies BRD4 inhibition.
Figure 9B:
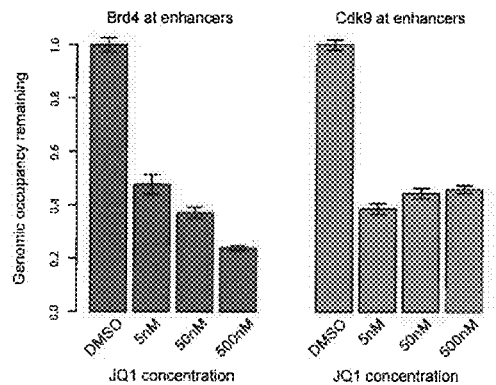
Figure 9C:
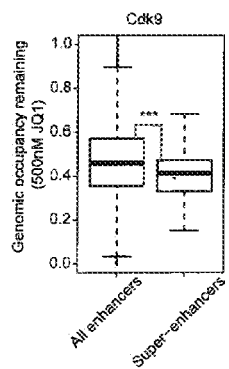

BRD4 recruits the active form of the positive transcription elongation factor P-TEFb, which stimulates pause release and transcription elongation (Bisgrove et al., 2007; Hargreaves et al., 2009; Jang et al., 2005; Jiang et al., 1998; Wu and Chiang, 2007; Wu et al., 2003; Yang et al., 2005). We used ChIP-Seq to investigate the global occupancy of P-TEFb in MM.1S cells and found that it generally occupies sites bound by Mediator and BRD4 (FIG. 9A). We next investigated whether the loss of BRD4 observed with JQ1 treatment is accompanied by loss of P-TEFb at enhancers and transcription start sites. JQ1 treatment did indeed reduce the levels of P-TEFb at sites where there was a reduction in BRD4 (FIG. 9B). Furthermore, P-TEFb was disproportionately lost at super-enhancers when compared to normal enhancers (FIG. 9C). We conclude that BET bromodomain inhibition of BRD4 leads to loss of P-TEFb at enhancers and transcription start sites, and that the inhibition has more profound effects at super-enhancers than at average enhancers.

Figure 10A:
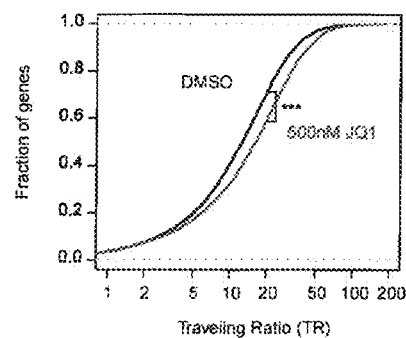
FIGS. 10A, 10B and 10C demonstrate that JQ1 causes disproportionate loss of transcription at super-enhancer genes.
Figure 10B:
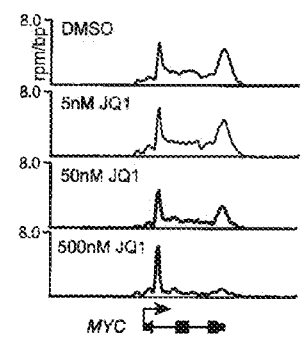
Figure 10C:
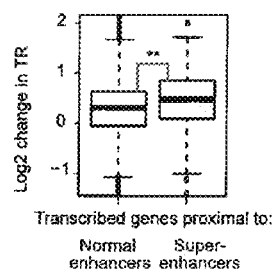

To determine whether the loss of P-TEFb results in an elongation defect, we performed ChIP-seq of RNA Polymerase II (Pol II) after JQ1 treatment. We found that JQ1 treatment led to a global defect in transcriptional elongation, characterized by a loss of PolIII in the gene body and 3' transcription termination regions (FIG. 10). Further inspection of gene tracks revealed that key super-enhancer associated genes, including MYC, showed a dramatic defect in elongation (FIG. 10B). Globally, super-enhancer associated genes, had larger elongation defects in response to JQ1 than genes associated with normal enhancers (FIG. 10C). These results are consistent with the interpretation that genes driven by super-enhancers show more dramatic transcriptional defects due to reduced pause release and elongation of their transcripts.

Discussion

At present, inhibitors of chromatin regulators are gaining increased interest as potential therapeutic agents for treating cancer. Many chromatin regulators are understood to play general roles in the control of transcription, yet to reach significant clinical efficacy, small molecule inhibitors must have a selective effect on tumor cells. Several recent studies have shown that inhibition of the bromodomain protein BRD4 can indeed have a highly specific effect, causing the down regulation of key tumor drivers in several cancer types. In multiple myeloma, acute myeloid leukemia, and Burkitt's lymphoma, treatment with BET inhibitors led to a dramatic loss of MYC expression (Dawson et al., 2011; Delmore et al., 2011; Mertz et al., 2011; Zuber et al., 2011). Understanding how inhibitors of generally acting chromatin regulators can exert a selective effect will vastly improve our understanding of how these drugs should be selected for the treatment of genetically-defined cancers.

We have gained insight into this concept through our study of super-enhancers. We have found that, across many cell types, key regulators of cell state are associated with large, 10-40 kb enhancer domains, characterized by disproportionately high levels of MED1 binding and, as we have profiled in multiple myeloma, BRD4. Although these super-enhancers make up only a small percentage of the total number of enhancer regions, they account for a large fraction of total MED1 and BRD4 binding across the genome. Most significantly, we have found that super-enhancers are more sensitive to perturbation than typical enhancer regions.

We found that inhibition of BRD4 led to the dramatic loss of BRD4 and CDK9 binding at super-enhancers. In multiple myeloma, super-enhancers were associated with key oncogenic drivers, such as MYC. Disruption of super-enhancers by BRD4 inhibition led to a dramatic loss of expression of these critical tumor genes, accompanied by a potent antiproliferative effect.

Our results demonstrate that super-enhancers occupied by BRD4 regulate critical oncogenic drivers multiple myeloma and show that BRD4 inhibition leads to preferential disruption of these super-enhancers. This insight into the mechanism by which Brd4 inhibition causes selective loss of oncogene expression in these highly malignant blood cancers may have implications for future drug development in oncology. Many oncogenes critical to tumor cell function are highly expressed and may therefore be driven by super-enhancers. If so, preferential disruption of super-enhancer function may be a general approach to selectively inhibiting the oncogenic drivers of many tumor cells.

REFERENCES

Bisgrove, D. A., Mahmoudi, T., Henklein, P., and Verdin, E. (2007). Conserved P-TEFb-interacting domain of BRD4 inhibits HIV transcription. Proc Natl Acad Sci USA 104, 13690-13695.

Carey, M. (1998). The enhanceosome and transcriptional synergy. Cell 92, 5-8.

Carey, M., Leatherwood, J., and Ptashne, M. (1990). A potent GAL4 derivative activates transcription at a distance in vitro. Science 247, 710-712.

Dawson, M. A., Prinjha, R. K., Dittmann, A., Giotopoulos, G., Bantscheff, M., Chan, W. I., Robson, S. C., Chung, C. W, Hopf, C., Savitski, M. M., et al. (2011), Inhibition of BET recruitment to chromatin as an effective treatment for MLL-fusion leukaemia. Nature 478, 529-533.

Delmore, J. E., Issa, G. C., Lemieux, M. E., Rahl, P. B., Shi, J., Jacobs, H. M., Kastritis, E., Gilpatrick, T., Paranal, R. M., Qi, J., et al. (2011). BET bromodomain inhibition as a therapeutic strategy to target c-Myc. Cell 146, 904-917.

Filippakopoulos, P., Picaud, S., Mangos, M., Keates, T., Lambert, J. P., Barsyte-Lovejoy, D., Felletar, I., Volkmer, R., Muller, S., Pawson, T., et al. (2012). Histone recognition and large-scale structural analysis of the human bromodomain family. Cell 149, 214-231.

Filippakopoulos, P., Qi, J., Picaud, S., Shen, Y., Smith, W. B., Fedorov, O., Morse, E. M., Keates, T., Hickman, T. T., Felletar, I., et al. (2010). Selective inhibition of BET bromodomains. Nature 468, 1067-1073.

Giese, K., Kingsley, C., Kirshner, J. R., and Grosschedl, R. (1995). Assembly and function of a TCR alpha enhancer complex is dependent on LEF-1-induced DNA bending and multiple protein-protein interactions. Genes Dev 9, 995-1008.

Giniger, E., and Ptashne, M. (1988). Cooperative DNA binding of the yeast transcriptional activator GAL4. Proc Natl Acad Sci USA 85, 382-386.

Griggs, D. W., and Johnston, M. (1991). Regulated expression of the GAL4 activator gene in yeast provides a sensitive genetic switch for glucose repression. Proc Natl Acad Sci USA 88, 8597-8601.

Hargreaves, D. C., Horng, T., and Medzhitov, R. (2009). Control of Inducible Gene Expression by Signal-Dependent Transcriptional Elongation. Cell 138, 129-145.

Jang, M. K., Mochizuki, K., Zhou, M., Jeong, H. S., Brady, J. N., and Ozato, K. (2005). The bromodomain protein Brd4 is a positive regulatory component of P-TEFb and stimulates RNA polymerase II-dependent transcription. Mol Cell 19, 523-534.

Jiang, Y. W., Veschambre, P., Erdjument-Bromage, H., Tempst, P., Conaway, J. W., Conaway, R. C., and Kornberg, R. D. (1998). Mammalian mediator of transcriptional regulation and its possible role as an end-point of signal transduction pathways. Proc Natl Acad Sci USA 95, 8538-8543.

Kim, T. K., and Maniatis, T. (1997). The mechanism of transcriptional synergy of an in vitro assembled interferon-beta enhanceosome. Mol Cell 1, 119-129.

Mertz, J. A., Conery, A. R., Bryant, B. M., Sandy, P., Balasubramanian, S., Mele, D. A., Bergeron, L., and Sims, R. J., 3rd (2011). Targeting MYC dependence in cancer by inhibiting BET bromodomains. Proc Natl Acad Sci USA 108, 16669-16674.

Nair, S. K., and Burley, S. K. (2003). X-ray structures of Myc-Max and Mad-Max recognizing DNA. Molecular bases of regulation by proto-oncogenic transcription factors. Cell 112, 193-205.

Nicodeme, E., Jeffrey, K. L., Schaefer, U., Reinke, S., Dewell, S., Chung, C. W., Chandwani, R., Marazzi, I., Wilson, P., Coste, H., et al. (2010). Suppression of inflammation by a synthetic histone mimic. Nature 468, 1119-1123.

Shaffer, A. L., Emre, N. C., Lamy, L., Ngo, V. N., Wright, G., Xiao, W., Powell, J., Dave, S., Yu, X., Zhao, H., et al. (2008). IRF4 addiction in multiple myeloma. Nature 454, 226-231.

Thanos, D., and Maniatis, T. (1995). Virus induction of human IFN beta gene expression requires the assembly of an enhanceosome. Cell 83, 1091-1100.

Wu, S. Y., and Chiang, C. M. (2007). The double bromodomain-containing chromatin adaptor Brd4 and transcriptional regulation. J Biol Chem 282, 13141-13145.

Wu, S. Y., Zhou, T., and Chiang, C. M. (2003). Human mediator enhances activator-facilitated recruitment of RNA polymerase 11 and promoter recognition by TATA-binding protein (TBP) independently of TBP-associated factors. Mol Cell Biol 23, 6229-6242.

Yang, Z., Yik, Chen, R., He, N., Jang, M. K., Ozato, K., and Zhou, Q. (2005). Recruitment of P-TEFb for stimulation of transcriptional elongation by the bromodomain protein Brd4. Mol Cell 19, 535-545.

Zuber, J., Shi, J., Wang, E., Rappaport, A. R., Herrmann, H., Sison, E. A., Magoon, D., Qi, J., Blatt, K., Wunderlich, M., et al. (2011). RNAi screen identifies Brd4 as a therapeutic target in acute myeloid leukaemia. Nature 478, 524-528.

TABLE 1

Super-enhancers from ESC. Based on NCBI Build 37

| REGION_ID | CHROM | START | STOP |
|---|---|---|---|
| INT_STITCHED_45 | chr1 | 13049615 | 13094765 |
| INT_STITCHED_88 | chr1 | 34130107 | 34134640 |
| INT_STITCHED_100 | chr1 | 36070190 | 36074608 |
| INT_STITCHED_101 | chr1 | 36111164 | 36118698 |
| INT_STITCHED_108 | chr1 | 37039139 | 37045411 |
| INT_STITCHED_230 | chr1 | 72260528 | 72261272 |
| INT_STITCHED_237 | chr1 | 72839563 | 72858199 |
| INT_STITCHED_282 | chr1 | 84857219 | 84887132 |
| INT_STITCHED_315 | chr1 | 91766947 | 91773527 |
| INT_STITCHED_368 | chr1 | 120538712 | 120545414 |
| INT_STITCHED_372 | chr1 | 120971968 | 120973737 |
| INT_STITCHED_374 | chr1 | 121201424 | 121202481 |
| INT_STITCHED_376 | chr1 | 121295085 | 121296031 |
| INT_STITCHED_449 | chr1 | 137071028 | 137096284 |
| INT_STITCHED_464 | chr1 | 138586629 | 138593131 |
| INT_STITCHED_466 | chr1 | 138841643 | 138850970 |
| INT_STITCHED_508 | chr1 | 154939892 | 154943709 |
| INT_STITCHED_556 | chr1 | 168054897 | 168073079 |
| INT_STITCHED_559 | chr1 | 169201106 | 169220423 |
| INT_STITCHED_610 | chr1 | 182818684 | 182819554 |
| INT_STITCHED_611 | chr1 | 182854521 | 182864307 |
| INT_STITCHED_615 | chr1 | 183948212 | 183961841 |
| INT_STITCHED_746 | chr2 | 20574602 | 20591747 |
| INT_STITCHED_803 | chr2 | 30913257 | 30925299 |
| INT_STITCHED_812 | chr2 | 32008891 | 32030736 |
| INT_STITCHED_817 | chr2 | 33282029 | 33300860 |
| INT_STITCHED_928 | chr2 | 71488013 | 71494617 |
| INT_STITCHED_931 | chr2 | 71575856 | 71583914 |
| INT_STITCHED_1196 | chr2 | 152002668 | 152003777 |
| INT_STITCHED_1198 | chr2 | 152552277 | 152563676 |
| INT_STITCHED_1210 | chr2 | 154242651 | 154254374 |
| INT_STITCHED_1256 | chr2 | 162856904 | 162860933 |
| INT_STITCHED_1257 | chr2 | 162877048 | 162893236 |
| INT_STITCHED_1279 | chr2 | 165981373 | 165983444 |
| INT_STITCHED_1300 | chr2 | 168589688 | 168617170 |
| INT_STITCHED_1392 | chr3 | 9641461 | 9655131 |
| INT_STITCHED_1480 | chr3 | 34544904 | 34553511 |
| INT_STITCHED_1482 | chr3 | 34633687 | 34660705 |
| INT_STITCHED_1607 | chr3 | 88375442 | 88380083 |
| INT_STITCHED_1626 | chr3 | 95455034 | 95468269 |
| INT_STITCHED_1629 | chr3 | 96380383 | 96382115 |

TABLE 1-continued

Super-enhancers from ESC. Based on NCBI Build 37

| REGION_ID | CHROM | START | STOP |
|---|---|---|---|
| INT_STITCHED_1630 | chr3 | 96479158 | 96484864 |
| INT_STITCHED_1658 | chr3 | 103008304 | 103019058 |
| INT_STITCHED_1732 | chr3 | 129247012 | 129261362 |
| INT_STITCHED_1744 | chr3 | 133181431 | 133197648 |
| INT_STITCHED_1749 | chr3 | 135208956 | 135210744 |
| INT_STITCHED_1973 | chr4 | 55469259 | 55491081 |
| INT_STITCHED_2076 | chr4 | 98507649 | 98514709 |
| INT_STITCHED_2152 | chr4 | 118743867 | 118745786 |
| INT_STITCHED_2175 | chr4 | 123300547 | 123303179 |
| INT_STITCHED_2192 | chr4 | 125211671 | 125223450 |
| INT_STITCHED_2205 | chr4 | 126875757 | 126879027 |
| INT_STITCHED_2223 | chr4 | 130178808 | 130180168 |
| INT_STITCHED_2224 | chr4 | 130195646 | 130196547 |
| INT_STITCHED_2265 | chr4 | 137148873 | 137153839 |
| INT_STITCHED_2268 | chr4 | 137329436 | 137357766 |
| INT_STITCHED_2273 | chr4 | 138000554 | 138006368 |
| INT_STITCHED_2291 | chr4 | 140826072 | 140840922 |
| INT_STITCHED_2292 | chr4 | 141120768 | 141126477 |
| INT_STITCHED_2295 | chr4 | 141616653 | 141627603 |
| INT_STITCHED_2297 | chr4 | 141721916 | 141726166 |
| INT_STITCHED_2317 | chr4 | 147459254 | 147463850 |
| INT_STITCHED_2354 | chr4 | 154537213 | 154538078 |
| INT_STITCHED_2355 | chr4 | 154563584 | 154564383 |
| INT_STITCHED_2465 | chr5 | 33873714 | 33880481 |
| INT_STITCHED_2510 | chr5 | 53933177 | 53947327 |
| INT_STITCHED_2535 | chr5 | 65255735 | 65256794 |
| INT_STITCHED_2712 | chr5 | 113758941 | 113775389 |
| INT_STITCHED_2736 | chr5 | 116845764 | 116860853 |
| INT_STITCHED_2745 | chr5 | 118884660 | 118896412 |
| INT_STITCHED_2746 | chr5 | 118951444 | 118960269 |
| INT_STITCHED_2752 | chr5 | 120029649 | 120037063 |
| INT_STITCHED_2754 | chr5 | 120129592 | 120171482 |
| INT_STITCHED_2770 | chr5 | 123584659 | 123590728 |
| INT_STITCHED_2830 | chr5 | 135417523 | 135421698 |
| INT_STITCHED_3005 | chr6 | 31834643 | 31852445 |
| INT_STITCHED_3044 | chr6 | 39370384 | 39371286 |
| INT_STITCHED_3045 | chr6 | 39395571 | 39396779 |
| INT_STITCHED_3120 | chr6 | 64961359 | 64985161 |
| INT_STITCHED_3130 | chr6 | 67061148 | 67064202 |
| INT_STITCHED_3184 | chr6 | 83839914 | 83844315 |
| INT_STITCHED_3217 | chr6 | 91640161 | 91661247 |
| INT_STITCHED_3342 | chr6 | 122290093 | 122293017 |
| INT_STITCHED_3347 | chr6 | 122612514 | 122614260 |
| INT_STITCHED_3348 | chr6 | 122640118 | 122657871 |
| INT_STITCHED_3349 | chr6 | 122714316 | 122720862 |
| INT_STITCHED_3360 | chr6 | 125383335 | 125398024 |
| INT_STITCHED_3429 | chr6 | 142458188 | 142461905 |
| INT_STITCHED_3437 | chr6 | 143047309 | 143065758 |
| INT_STITCHED_3450 | chr6 | 145223385 | 145225674 |
| INT_STITCHED_3467 | chr7 | 3193004 | 3218183 |
| INT_STITCHED_3475 | chr7 | 4772296 | 4777612 |
| INT_STITCHED_3481 | chr7 | 13599334 | 13600325 |
| INT_STITCHED_3523 | chr7 | 30982397 | 30983339 |
| INT_STITCHED_3525 | chr7 | 31248315 | 31250619 |
| INT_STITCHED_3550 | chr7 | 38812914 | 38816123 |
| INT_STITCHED_3568 | chr7 | 52806853 | 52814768 |
| INT_STITCHED_3576 | chr7 | 56592909 | 56604632 |
| INT_STITCHED_3601 | chr7 | 71092246 | 71102481 |
| INT_STITCHED_3652 | chr7 | 86355826 | 86368339 |
| INT_STITCHED_3658 | chr7 | 87159908 | 87169963 |
| INT_STITCHED_3661 | chr7 | 87274999 | 87276022 |
| INT_STITCHED_3662 | chr7 | 87333420 | 87345334 |
| INT_STITCHED_3685 | chr7 | 91027196 | 91051830 |
| INT_STITCHED_3765 | chr7 | 119831735 | 119835688 |
| INT_STITCHED_3856 | chr7 | 140304156 | 140307245 |
| INT_STITCHED_3890 | chr7 | 147131117 | 147136231 |
| INT_STITCHED_3914 | chr7 | 152036872 | 152050716 |
| INT_STITCHED_3947 | chr8 | 12499468 | 12504771 |
| INT_STITCHED_4014 | chr8 | 35023426 | 35027483 |
| INT_STITCHED_4033 | chr8 | 37602064 | 37613850 |
| INT_STITCHED_4034 | chr8 | 37642521 | 37671979 |
| INT_STITCHED_4046 | chr8 | 44405736 | 44406755 |
| INT_STITCHED_4116 | chr8 | 74834685 | 74840663 |
| INT_STITCHED_4163 | chr8 | 87174072 | 87174643 |
| INT_STITCHED_4167 | chr8 | 87996475 | 87997654 |
| INT_STITCHED_4179 | chr8 | 91514813 | 91540176 |

TABLE 1-continued

Super-enhancers from ESC. Based on NCBI Build 37

| REGION_ID | CHROM | START | STOP |
|---|---|---|---|
| INT_STITCHED_4190 | chr8 | 93351924 | 93355292 |
| INT_STITCHED_4546 | chr9 | 56382386 | 56395769 |
| INT_STITCHED_4555 | chr9 | 58119837 | 58128504 |
| INT_STITCHED_4657 | chr9 | 78207143 | 78223442 |
| INT_STITCHED_4748 | chr9 | 110849422 | 110863371 |
| INT_STITCHED_4766 | chr9 | 114458126 | 114474355 |
| INT_STITCHED_4797 | chr9 | 120585871 | 120600072 |
| INT_STITCHED_4802 | chr9 | 121244501 | 121254102 |
| INT_STITCHED_4885 | chr10 | 20802131 | 20830236 |
| INT_STITCHED_4891 | chr10 | 21546502 | 21549691 |
| INT_STITCHED_4893 | chr10 | 21700576 | 21708946 |
| INT_STITCHED_4954 | chr10 | 39977900 | 39978752 |
| INT_STITCHED_4981 | chr10 | 44110139 | 44112766 |
| INT_STITCHED_5021 | chr10 | 59420365 | 59437537 |
| INT_STITCHED_5044 | chr10 | 62346394 | 62361563 |
| INT_STITCHED_5054 | chr10 | 66380351 | 66383761 |
| INT_STITCHED_5059 | chr10 | 66546199 | 66564235 |
| INT_STITCHED_5091 | chr10 | 75335464 | 75345568 |
| INT_STITCHED_5092 | chr10 | 75400370 | 75401358 |
| INT_STITCHED_5100 | chr10 | 76655655 | 76662360 |
| INT_STITCHED_5111 | chr10 | 79508474 | 79515168 |
| INT_STITCHED_5140 | chr10 | 85002060 | 85006553 |
| INT_STITCHED_5325 | chr11 | 8466451 | 8486876 |
| INT_STITCHED_5331 | chr11 | 9015537 | 9017663 |
| INT_STITCHED_5340 | chr11 | 12357626 | 12370205 |
| INT_STITCHED_5427 | chr11 | 33427175 | 33451476 |
| INT_STITCHED_5484 | chr11 | 52173182 | 52184686 |
| INT_STITCHED_5499 | chr11 | 54767341 | 54785832 |
| INT_STITCHED_5533 | chr11 | 62324296 | 62327251 |
| INT_STITCHED_5553 | chr11 | 66733372 | 66746990 |
| INT_STITCHED_5555 | chr11 | 66824791 | 66838230 |
| INT_STITCHED_5565 | chr11 | 69517060 | 69522803 |
| INT_STITCHED_5597 | chr11 | 77697704 | 77718786 |
| INT_STITCHED_5666 | chr11 | 88481360 | 88491812 |
| INT_STITCHED_5711 | chr11 | 97517673 | 97524159 |
| INT_STITCHED_5719 | chr11 | 98823511 | 98826466 |
| INT_STITCHED_5741 | chr11 | 102190649 | 102193692 |
| INT_STITCHED_5752 | chr11 | 104150171 | 104167544 |
| INT_STITCHED_5768 | chr11 | 107296669 | 107310982 |
| INT_STITCHED_5819 | chr11 | 116943025 | 116953583 |
| INT_STITCHED_5831 | chr11 | 117833701 | 117838253 |
| INT_STITCHED_5875 | chr12 | 12790432 | 12795881 |
| INT_STITCHED_5876 | chr12 | 12810177 | 12811020 |
| INT_STITCHED_5880 | chr12 | 12933791 | 12950936 |
| INT_STITCHED_5995 | chr12 | 55407498 | 55415046 |
| INT_STITCHED_6000 | chr12 | 56587347 | 56607146 |
| INT_STITCHED_6004 | chr12 | 57385208 | 57400114 |
| INT_STITCHED_6112 | chr12 | 87807046 | 87820319 |
| INT_STITCHED_6113 | chr12 | 87839385 | 87846192 |
| INT_STITCHED_6118 | chr12 | 88239005 | 88245155 |
| INT_STITCHED_6151 | chr12 | 103940487 | 103953004 |
| INT_STITCHED_6186 | chr12 | 111655417 | 111656705 |
| INT_STITCHED_6187 | chr12 | 111709296 | 111710794 |
| INT_STITCHED_6188 | chr12 | 111725920 | 111743677 |
| INT_STITCHED_6460 | chr13 | 64069823 | 64082322 |
| INT_STITCHED_6544 | chr13 | 96295094 | 96306119 |
| INT_STITCHED_6557 | chr13 | 98052562 | 98062842 |
| INT_STITCHED_6559 | chr13 | 98202400 | 98225162 |
| INT_STITCHED_6615 | chr13 | 110418702 | 110442750 |
| INT_STITCHED_6709 | chr14 | 22293688 | 22308989 |
| INT_STITCHED_6789 | chr14 | 49273113 | 49283200 |
| INT_STITCHED_6815 | chr14 | 55704349 | 55705463 |
| INT_STITCHED_6859 | chr14 | 64118817 | 64131901 |
| INT_STITCHED_6864 | chr14 | 65251303 | 65269514 |
| INT_STITCHED_6887 | chr14 | 71022659 | 71035930 |
| INT_STITCHED_6904 | chr14 | 76894682 | 76915946 |
| INT_STITCHED_6906 | chr14 | 77015215 | 77030315 |
| INT_STITCHED_6957 | chr14 | 99738540 | 99755307 |
| INT_STITCHED_6981 | chr14 | 106250319 | 106260753 |
| INT_STITCHED_6982 | chr14 | 106296486 | 106304433 |
| INT_STITCHED_7104 | chr15 | 25654102 | 25704265 |
| INT_STITCHED_7202 | chr15 | 61918415 | 61924748 |
| INT_STITCHED_7248 | chr15 | 77168852 | 77187251 |
| INT_STITCHED_7285 | chr15 | 88539016 | 88539831 |
| INT_STITCHED_7317 | chr15 | 97198605 | 97227633 |
| INT_STITCHED_7318 | chr15 | 97422878 | 97425328 |
| INT_STITCHED_7343 | chr15 | 103349226 | 103353500 |
| INT_STITCHED_7359 | chr16 | 8758173 | 8779472 |
| INT_STITCHED_7434 | chr16 | 23099373 | 23103471 |
| INT_STITCHED_7452 | chr16 | 29657509 | 29668114 |
| INT_STITCHED_7597 | chr16 | 84769173 | 84780686 |
| INT_STITCHED_7680 | chr17 | 10549089 | 10570838 |
| INT_STITCHED_7728 | chr17 | 26631721 | 26648689 |
| INT_STITCHED_7747 | chr17 | 29209618 | 29218426 |
| INT_STITCHED_7752 | chr17 | 29587776 | 29588942 |
| INT_STITCHED_7767 | chr17 | 31939569 | 31956756 |
| INT_STITCHED_7784 | chr17 | 35639211 | 35642435 |
| INT_STITCHED_7792 | chr17 | 37110202 | 37134996 |
| INT_STITCHED_7794 | chr17 | 37209046 | 37217726 |
| INT_STITCHED_7812 | chr17 | 45593477 | 45596503 |
| INT_STITCHED_7822 | chr17 | 47640414 | 47649043 |
| INT_STITCHED_7876 | chr17 | 66818723 | 66836409 |
| INT_STITCHED_7884 | chr17 | 71096763 | 71100905 |
| INT_STITCHED_7886 | chr17 | 71177302 | 71179956 |
| INT_STITCHED_7887 | chr17 | 71213804 | 71222433 |
| INT_STITCHED_7888 | chr17 | 71241991 | 71250610 |
| INT_STITCHED_8114 | chr18 | 35202713 | 35203454 |
| INT_STITCHED_8124 | chr18 | 36412873 | 36414154 |
| INT_STITCHED_8136 | chr18 | 38538325 | 38551037 |
| INT_STITCHED_8139 | chr18 | 38760823 | 38761958 |
| INT_STITCHED_8140 | chr18 | 38788269 | 38796942 |
| INT_STITCHED_8148 | chr18 | 40467587 | 40468140 |
| INT_STITCHED_8209 | chr18 | 61787544 | 61788400 |
| INT_STITCHED_8260 | chr18 | 75504155 | 75505202 |
| INT_STITCHED_8261 | chr18 | 75520332 | 75527277 |
| INT_STITCHED_8264 | chr18 | 75738693 | 75745073 |
| INT_STITCHED_8324 | chr19 | 5835881 | 5847014 |
| INT_STITCHED_8378 | chr19 | 21858770 | 21866770 |
| INT_STITCHED_8385 | chr19 | 23139991 | 23170189 |
| INT_STITCHED_8386 | chr19 | 23207455 | 23208806 |
| INT_STITCHED_8399 | chr19 | 25553498 | 25564092 |
| INT_STITCHED_8519 | chr19 | 53523440 | 53535319 |
| INT_STITCHED_8554 | chrX | 7578969 | 7597907 |
| INT_STITCHED_8629 | chrX | 50098631 | 50114110 |

TABLE 2

Multiple Myeloma Super-enhancers. Based on Gene Build hg 18

| REGION_ID | CHROM | START | STOP |
|---|---|---|---|
| 3_MM1S_MED1_DMSO_2_11472_lociStitched | chr22 | 21597907 | 21632017 |
| 12_MM1S_MED1_DMSO_2_12661_lociStitched | chr3 | 142561889 | 142658635 |
| 5_MM1S_MED1_DMSO_2_11467_lociStitched | chr22 | 21520124 | 21576243 |
| 3_MM1S_MED1_DMSO_2_15142_lociStitched | chr6 | 7822980 | 7864682 |
| 27_MM1S_MED1_DMSO_2_15896_lociStitched | chr6 | 108969554 | 109119470 |
| 10_MM1S_MED1_DMSO_2_883_lociStitched | chr1 | 117943520 | 118031299 |
| 13_MM1S_MED1_DMSO_2_9297_lociStitched | chr2 | 37383079 | 37478117 |
| 7_MM1S_MED1_DMSO_2_1421_lociStitched | chr1 | 201502736 | 201564474 |
| 6_MM1S_MED1_DMSO_2_10778_lociStitched | chr20 | 29712568 | 29775967 |

TABLE 2-continued

Multiple Myeloma Super-enhancers. Based on Gene Build hg 18

| REGION_ID | CHROM | START | STOP |
|---|---|---|---|
| 4_MM1S_MED1_DMSO_2_3066_lociStitched | chr11 | 64939923 | 64979931 |
| 12_MM1S_MED1_DMSO_2_10818_lociStitched | chr20 | 31862228 | 31936793 |
| 15_MM1S_MED1_DMSO_2_19349_lociStitched | chrX | 130689710 | 130790383 |
| 6_MM1S_MED1_DMSO_2_15061_lociStitched | chr6 | 235131 | 282880 |
| MM1S_MED1_DMSO_2_4011 | chr12 | 51868026 | 51890008 |
| 13_MM1S_MED1_DMSO_2_6359_lociStitched | chr16 | 11662193 | 11750399 |
| 5_MM1S_MED1_DMSO_2_19070_lociStitched | chrX | 48652795 | 48690448 |
| 9_MM1S_MED1_DMSO_2_13894_lociStitched | chr4 | 185522607 | 185586220 |
| 2_MM1S_MED1_DMSO_2_15298_lociStitched | chr6 | 26263259 | 26281958 |
| 4_MM1S_MED1_DMSO_2_2709_lociStitched | chr11 | 10280174 | 10301780 |
| 7_MM1S_MED1_DMSO_2_11528_lociStitched | chr22 | 27516134 | 27555928 |
| 5_MM1S_MED1_DMSO_2_7255_lociStitched | chr17 | 29712450 | 29745538 |
| 9_MM1S_MED1_DMSO_2_9712_lociStitched | chr2 | 98426920 | 98498831 |
| 10_MM1S_MED1_DMSO_2_5371_lociStitched | chr14 | 90884807 | 90955651 |
| 3_MM1S_MED1_DMSO_2_7984_lociStitched | chr18 | 9050438 | 9074417 |
| 8_MM1S_MED1_DMSO_2_16690_lociStitched | chr7 | 55566748 | 55610180 |
| 1_MM1S_MED1_DMSO_2_935_lociStitched | chr1 | 148122391 | 148127826 |
| 3_MM1S_MED1_DMSO_2_3735_lociStitched | chr12 | 12748016 | 12781726 |
| 4_MM1S_MED1_DMSO_2_2546_lociStitched | chr10 | 125812311 | 125857688 |
| 2_MM1S_MED1_DMSO_2_1862_lociStitched | chr10 | 11242759 | 11275331 |
| 3_MM1S_MED1_DMSO_2_929_lociStitched | chr1 | 147470833 | 147491868 |
| MM1S_MED1_DMSO_2_15293 | chr6 | 26161696 | 26165891 |
| 3_MM1S_MED1_DMSO_2_9167_lociStitched | chr2 | 20254183 | 20289776 |
| 1_MM1S_MED1_DMSO_2_15301_lociStitched | chr6 | 26303073 | 26309499 |
| 11_MM1S_MED1_DMSO_2_17447_lociStitched | chr8 | 27264787 | 27340169 |
| 3_MM1S_MED1_DMSO_2_178_lociStitched | chr1 | 17094196 | 17113973 |
| 13_MM1S_MED1_DMSO_2_17882_lociStitched | chr8 | 120985081 | 121017049 |
| 3_MM1S_MED1_DMSO_2_1025_lociStitched | chr1 | 153174936 | 153197206 |
| 1_MM1S_MED1_DMSO_2_13984_lociStitched | chr5 | 1364911 | 1374105 |
| MM1S_MED1_DMSO_2_15361 | chr6 | 27964884 | 27972054 |
| 3_MM1S_MED1_DMSO_2_3071_lociStitched | chr11 | 65020047 | 65035435 |
| 5_MM1S_MED1_DMSO_2_18418_lociStitched | chr9 | 92710817 | 92746187 |
| 3_MM1S_MED1_DMSO_2_13885_lociStitched | chr4 | 185421650 | 185447815 |
| 5_MM1S_MED1_DMSO_2_9691_lociStitched | chr2 | 96554603 | 96584612 |
| 10_MM1S_MED1_DMSO_2_15652_lociStitched | chr6 | 52501063 | 52557406 |
| MM1S_MED1_DMSO_2_7572 | chr17 | 53760011 | 53773039 |
| 6_MM1S_MED1_DMSO_2_15868_lociStitched | chr6 | 106637997 | 106665835 |
| 1_MM1S_MED1_DMSO_2_15308_lociStitched | chr6 | 26377785 | 26382951 |
| 2_MM1S_MED1_DMSO_2_7420_lociStitched | chr17 | 38792419 | 38802756 |
| 9_MM1S_MED1_DMSO_2_14628_lociStitched | chr5 | 131818986 | 131870127 |
| 3_MM1S_MED1_DMSO_2_13539_lociStitched | chr4 | 90429430 | 90459112 |
| 4_MM1S_MED1_DMSO_2_12859_lociStitched | chr3 | 178538717 | 178562722 |
| 4_MM1S_MED1_DMSO_2_4371_lociStitched | chr12 | 107533824 | 107560420 |
| 4_MM1S_MED1_DMSO_2_15314_lociStitched | chr6 | 26449533 | 26475951 |
| MM1S_MED1_DMSO_2_15291 | chr6 | 26138365 | 26142878 |
| 1_MM1S_MED1_DMSO_2_15296_lociStitched | chr6 | 26230241 | 26235063 |
| 9_MM1S_MED1_DMSO_2_5477_lociStitched | chr14 | 105096168 | 105120688 |
| 2_MM1S_MED1_DMSO_2_12120_lociStitched | chr3 | 46220865 | 46232443 |
| MM1S_MED1_DMSO_2_1 5292 | chr6 | 26150596 | 26154952 |
| 2_MM1S_MED1_DMSO_2_5546_lociStitched | chr15 | 29333964 | 29348240 |
| 1_MM1S_MED1_DMSO_2_176_lociStitched | chr1 | 16712194 | 16713944 |
| 1_MM1S_MED1_DMSO_2_12853_lociStitched | chr3 | 178395376 | 178403353 |
| 1_MM1S_MED1_DMSO_2_10897_lociStitched | chr20 | 36931952 | 36938862 |
| 2_MM1S_MED1_DMSO_2_9810_lociStitched | chr2 | 112172513 | 112182538 |
| 5_MM1S_MED1_DMSO_2_497_lociStitched | chr1 | 44945879 | 44970311 |
| 7_MM1S_MED1_DMSO_2_8152_lociStitched | chr18 | 44693277 | 44734029 |
| 1_MM1S_MED1_DMSO_2_3010_lociStitched | chr11 | 62362909 | 62367338 |
| 2_MM1S_MED1_DMSO_2_1718_lociStitched | chr1 | 232800286 | 232816291 |
| 7_MM1S_MED1_DMSO_2_16140_lociStitched | chr6 | 138287960 | 138339719 |
| 4_MM1S_MED1_DMSO_2_16924_lociStitched | chr7 | 101851129 | 101879762 |
| 7_MM1S_MED1_DMSO_2_3539_lociStitched | chr11 | 128090989 | 128134946 |
| 5_MM1S_MED1_DMSO_2_13905_lociStitched | chr4 | 185603808 | 185634087 |
| 5_MM1S_MED1_DMSO_2_8400_lociStitched | chr19 | 2546568 | 2579792 |
| 4_MM1S_MED1_DMSO_2_17232_lociStitched | chr7 | 149685067 | 149715545 |
| 9_MM1S_MED1_DMSO_2_6090_lociStitched | chr15 | 88364067 | 88447544 |
| 7_MM1S_MED1_DMSO_2_5551_lociStitched | chr15 | 29404247 | 29447806 |
| 6_MM1S_MED1_DMSO_2_908_lociStitched | chr1 | 144138338 | 144169442 |
| 6_MM1S_MED1_DMSO_2_2813_lociStitched | chr11 | 22633909 | 22661308 |
| 2_MM1S_MED1_DMSO_2_11309_lociStitched | chr21 | 40247390 | 40265606 |
| 3_MM1S_MED1_DMSO_2_11459_lociStitched | chr22 | 21406975 | 21431657 |
| 4_MM1S_MED1_DMSO_2_4023_lociStitched | chr12 | 52133823 | 52163301 |
| 3_MM1S_MED1_DMSO_2_6783_lociStitched | chr16 | 78185190 | 78197918 |
| 2_MM1S_MED1_DMSO_2_2451_lociStitched | chr10 | 112094075 | 112109393 |
| 4_MM1S_MED1_DMSO_2_3671_lociStitched | chr12 | 6916226 | 6942174 |
| 3_MM1S_MED1_DMSO_2_11367_lociStitched | chr21 | 44381407 | 44405755 |
| 6_MM1S_MED1_DMSO_2_18632_lociStitched | chr9 | 122670221 | 122707139 |

TABLE 2-continued

Multiple Myeloma Super-enhancers. Based on Gene Build hg 18

| REGION_ID | CHROM | START | STOP |
|---|---|---|---|
| 5_MM1S_MED1_DMSO_2_7098_lociStitched | chr17 | 16810645 | 16836243 |
| 5_MM1S_MED1_DMSO_2_12822_lociStitched | chr3 | 173284485 | 173309559 |
| 3_MM1S_MED1_DMSO_2_7795_lociStitched | chr17 | 72647302 | 72672300 |
| 5_MM1S_MED1_DMSO_2_14194_lociStitched | chr5 | 55473448 | 55500561 |
| 4_MM1S_MED1_DMSO_2_5843_lociStitched | chr15 | 63374708 | 63385346 |
| 7_MM1S_MED1_DMSO_2_12921_lociStitched | chr3 | 184711984 | 184757118 |
| 3_MM1S_MED1_DMSO_2_13004_lociStitched | chr3 | 195330092 | 195342991 |
| 6_MM1S_MED1_DMSO_2_1869_lociStitched | chr10 | 11323723 | 11353214 |
| 6_MM1S_MED1_DMSO_2_5884_lociStitched | chr15 | 66355713 | 66386773 |
| 4_MM1S_MED1_DMSO_2_16493_lociStitched | chr7 | 25953531 | 25975640 |
| 2_MM1S_MED1_DMSO_2_17945_lociStitched | chr8 | 128815143 | 128831262 |
| 3_MM1S_MED1_DMSO_2_6443_lociStitched | chr16 | 23241697 | 23269855 |
| 1_MM1S_MED1_DMSO_2_15307_lociStitched | chr6 | 26356880 | 26361949 |
| 4_MM1S_MED1_DMSO_2_1007_lociStitched | chr1 | 152636911 | 152660538 |
| 12_MM1S_MED1_DMSO_2_12617_lociStitched | chr3 | 134643043 | 134708940 |
| 3_MM1S_MED1_DMSO_2_1629_lociStitched | chr1 | 224363473 | 224383373 |
| 3_MM1S_MED1_DMSO_2_2794_lociStitched | chr11 | 19406910 | 19422183 |
| 2_MM1S_MED1_DMSO_2_4947_lociStitched | chr13 | 113545919 | 113557086 |
| 3_MM1S_MED1_DMSO_2_15146_lociStitched | chr6 | 7903492 | 7922524 |
| 2_MM1S_MED1_DMSO_2_9355_lociStitched | chr2 | 43297983 | 43310825 |
| MM1S_MED1_DMSO_2_15353 | chr6 | 27882353 | 27887636 |
| 1_MM1S_MED1_DMSO_2_117_lociStitched | chr1 | 11889871 | 11893140 |
| 5_MM1S_MED1_DMSO_2_11097_lociStitched | chr20 | 55481270 | 55509295 |
| 1_MM1S_MED1_DMSO_2_10440_lociStitched | chr2 | 231437101 | 231447701 |
| 3_MM1S_MED1_DMSO_2_340_lociStitched | chr1 | 30988720 | 31005936 |
| 7_MM1S_MED1_DMSO_2_15801_lociStitched | chr6 | 90115755 | 90142733 |
| 3_MM1S_MED1_DMSO_2_9401_lociStitched | chr2 | 47380900 | 47404415 |
| 1_MM1S_MED1_DMSO_2_15359_lociStitched | chr6 | 27939690 | 27944056 |
| 6_MM1S_MED1_DMSO_2_16939_lociStitched | chr7 | 104350354 | 104392312 |
| 4_MM1S_MED1_DMSO_2_14621_lociStitched | chr5 | 131777514 | 131802069 |
| 9_MM1S_MED1_DMSO_2_7852_lociStitched | chr17 | 74224147 | 74290965 |
| 5_MM1S_MED1_DMSO_2_10765_lociStitched | chr20 | 25209731 | 25248761 |
| 3_MM1S_MED1_DMSO_2_11306_lociStitched | chr21 | 40217819 | 40231333 |
| 1_MM1S_MED1_DMSO_2_4955_lociStitched | chr13 | 113847326 | 113853279 |
| 9_MM1S_MED1_DMSO_2_17774_lociStitched | chr8 | 96022708 | 96074048 |
| 1_MM1S_MED1_DMSO_2_15467_lociStitched | chr6 | 33042969 | 33050991 |
| 2_MM1S_MED1_DMSO_2_10245_lociStitched | chr2 | 201688028 | 201701230 |
| 2_MM1S_MED1_DMSO_2_3620_lociStitched | chr12 | 4086510 | 4100254 |
| 1_MM1S_MED1_DMSO_2_11604_lociStitched | chr22 | 35056163 | 35061482 |
| 5_MM1S_MED1_DMSO_2_8117_lociStitched | chr18 | 40542132 | 40560323 |
| 5_MM1S_MED1_DMSO_2_17304_lociStitched | chr8 | 2016787 | 2037760 |
| 11_MM1S_MED1_DMSO_2_7624_lociStitched | chr17 | 59486930 | 59536700 |
| 5_MM1S_MED1_DMSO_2_7793_lociStitched | chr17 | 72590686 | 72618288 |
| 2_MM1S_MED1_DMSO_2_15176_lociStitched | chr6 | 11937666 | 11944210 |
| 3_MM1S_MED1_DMSO_2_8375_lociStitched | chr19 | 2032758 | 2049163 |
| 5_MM1S_MED1_DMSO_2_10377_lociStitched | chr2 | 219449340 | 219471887 |
| 1_MM1S_MED1_DMSO_2_18431_lociStitched | chr9 | 92992632 | 92996907 |
| MM1S_MED1_DMSO_2_8809 | chr19 | 44583388 | 44595931 |
| 6_MM1S_MED1_DMSO_2_19132_lociStitched | chrX | 58141354 | 58176568 |
| 2_MM1S_MED1_DMSO_2_11329_lociStitched | chr21 | 42353240 | 42371485 |
| 3_MM1S_MED1_DMSO_2_3939_lociStitched | chr12 | 46487401 | 46506636 |
| 2_MM1S_MED1_DMSO_2_2457_lociStitched | chr10 | 112205500 | 112215498 |
| 6_MM1S_MED1_DMSO_2_6074_lociStitched | chr15 | 87434644 | 87475737 |
| 2_MM1S_MED1_DMSO_2_1061_lociStitched | chr1 | 154382144 | 154399688 |
| 6_MM1S_MED1_DMSO_2_14486_lociStitched | chr5 | 109279819 | 109314997 |
| 2_MM1S_MED1_DMSO_2_218_lociStitched | chr1 | 23723110 | 23739682 |
| 6_MM1S_MED1_DMSO_2_11882_lociStitched | chr3 | 5197581 | 5231167 |
| 5_MM1S_MED1_DMSO_2_8393_lociStitched | chr19 | 2419984 | 2446976 |
| 1_MM1S_MED1_DMSO_2_11487_lociStitched | chr22 | 22514623 | 22522474 |
| 5_MM1S_MED1_DMSO_2_11633_lociStitched | chr22 | 35940694 | 35972007 |
| 4_MM1S_MED1_DMSO_2_13300_lociStitched | chr4 | 39868398 | 39884094 |
| 2_MM1S_MED1_DMSO_2_15875_lociStitched | chr6 | 106717009 | 106735272 |
| 4_MM1S_MED1_DMSO_2_16685_lociStitched | chr7 | 55537132 | 55553461 |
| 2_MM1S_MED1_DMSO_2_13593_lociStitched | chr4 | 105626955 | 105636498 |
| 1_MM1S_MED1_DMSO_2_5492_lociStitched | chr14 | 105394828 | 105400642 |
| 2_MM1S_MED1_DMSO_2_1032_lociStitched | chr1 | 153236845 | 153257390 |
| 6_MM1S_MED1_DMSO_2_6769_lociStitched | chr16 | 77326423 | 77362760 |
| 4_MM1S_MED1_DMSO_2_15040_lociStitched | chr5 | 180161278 | 180192831 |
| 2_MM1S_MED1_DMSO_2_11510_lociStitched | chr22 | 25335621 | 25345570 |
| 4_MM1S_MED1_DMSO_2_5303_lociStitched | chr14 | 76557983 | 76580142 |
| 3_MM1S_MED1_DMSO_2_15065_lociStitched | chr6 | 334189 | 345497 |
| 2_MM1S_MED1_DMSO_2_10912_lociStitched | chr20 | 40143996 | 40158547 |
| 5_MM1S_MED1_DMSO_2_6691_lociStitched | chr16 | 66841952 | 66878349 |
| 1_MM1S_MED1_DMSO_2_7334_lociStitched | chr17 | 35163138 | 35168797 |
| 2_MM1S_MED1_DMSO_2_18434_lociStitched | chr9 | 93221024 | 93234776 |
| 3_MM1S_MED1_DMSO_2_8242_lociStitched | chr18 | 58955785 | 58981327 |

TABLE 2-continued

Multiple Myeloma Super-enhancers. Based on Gene Build hg 18

| REGION_ID | CHROM | START | STOP |
|---|---|---|---|
| 1_MM1S_MED1_DMSO_2_13003_lociStitched | chr3 | 195300012 | 195305617 |
| 2_MM1S_MED1_DMSO_2_6646_lociStitched | chr16 | 65106878 | 65117734 |
| 3_MM1S_MED1_DMSO_2_4266_lociStitched | chr12 | 93065052 | 93093164 |
| 3_MM1S_MED1_DMSO_2_11259_lociStitched | chr21 | 35158227 | 35184979 |
| 4_MM1S_MED1_DMSO_2_3801_lociStitched | chr12 | 26157584 | 26171339 |
| 2_MM1S_MED1_DMSO_2_16133_lociStitched | chr6 | 138228659 | 138247051 |
| 3_MM1S_MED1_DMSO_2_17236_lociStitched | chr7 | 149731864 | 149749863 |
| 4_MM1S_MED1_DMSO_2_13002_lociStitched | chr3 | 195258091 | 195287025 |
| 2_MM1S_MED1_DMSO_2_953_lociStitched | chr1 | 148798802 | 148808298 |
| 2_MM1S_MED1_DMSO_2_1450_lociStitched | chr1 | 203508812 | 203524935 |
| 2_MM1S_MED1_DMSO_2_15283_lociStitched | chr6 | 25511304 | 25522342 |
| 3_MM1S_MED1_DMSO_2_290_lociStitched | chr1 | 26890818 | 26902191 |
| 5_MM1S_MED1_DMSO_2_7990_lociStitched | chr18 | 9091649 | 9111559 |
| 7_MM1S_MED1_DMSO_2_18762_lociStitched | chr9 | 133102585 | 133143969 |
| 1_MM1S_MED1_DMSO_2_11360_lociStitched | chr21 | 44021842 | 44029128 |
| 2_MM1S_MED1_DMSO_2_3442_lociStitched | chr11 | 118244109 | 118249498 |
| 3_MM1S_MED1_DMSO_2_240_lociStitched | chr1 | 24384810 | 24406266 |
| 3_MM1S_MED1_DMSO_2_13402_lociStitched | chr4 | 71744317 | 71766940 |
| 1_MM1S_MED1_DMSO_2_1504_lociStitched | chr1 | 207342554 | 207349164 |
| 2_MM1S_MED1_DMSO_2_3411_lociStitched | chr11 | 114631374 | 114641681 |
| 1_MM1S_MED1_DMSO_2_6445_lociStitched | chr16 | 23321100 | 23326979 |
| 3_MM1S_MED1_DMSO_2_15550_lociStitched | chr6 | 37230628 | 37252404 |
| 2_MM1S_MED1_DMSO_2_13986_lociStitched | chr5 | 1388551 | 1399215 |
| 4_MM1S_MED1_DMSO_2_1441_lociStitched | chr1 | 202729083 | 202757890 |
| 4_MM1S_MED1_DMSO_2_1469_lociStitched | chr1 | 204784341 | 204809621 |
| 1_MM1S_MED1_DMSO_2_10460_lociStitched | chr2 | 232278796 | 232285774 |
| 2_MM1S_MED1_DMSO_2_2970_lociStitched | chr11 | 60354930 | 60369771 |
| 3_MM1S_MED1_DMSO_2_8650_lociStitched | chr19 | 16555465 | 16572388 |
| 9_MM1S_MED1_DMSO_2_12125_lociStitched | chr3 | 46292850 | 46331709 |
| 1_MM1S_MED1_DMSO_2_16944_lociStitched | chr7 | 104438848 | 104443908 |
| 3_MM1S_MED1_DMSO_2_19007_lociStitched | chrX | 39838174 | 39854463 |
| 1_MM1S_MED1_DMSO_2_3626_lociStitched | chr12 | 4247853 | 4257225 |
| 2_MM1S_MED1_DMSO_2_14483_lociStitched | chr5 | 109219736 | 109229823 |
| 6_MM1S_MED1_DMSO_2_12115_lociStitched | chr3 | 46081401 | 46126461 |
| 3_MM1S_MED1_DMSO_2_11151_lociStitched | chr20 | 61828935 | 61842486 |
| 4_MM1S_MED1_DMSO_2_5613_lociStitched | chr15 | 38175241 | 38196125 |
| 4_MM1S_MED1_DMSO_2_13278_lociStitched | chr4 | 37983729 | 37998765 |
| 6_MM1S_MED1_DMSO_2_5325_lociStitched | chr14 | 81000404 | 81025576 |
| 5_MM1S_MED1_DMSO_2_8632_lociStitched | chr19 | 16112417 | 16131135 |
| 7_MM1S_MED1_DMSO_2_6134_lociStitched | chr15 | 91147531 | 91189935 |
| 1_MM1S_MED1_DMSO_2_7450_lociStitched | chr17 | 40653952 | 40663191 |
| 5_MM1S_MED1_DMSO_2_1463_lociStitched | chr1 | 204455280 | 204477658 |
| 3_MM1S_MED1_DMSO_2_12583_lociStitched | chr3 | 130511014 | 130530874 |
| 1_MM1S_MED1_DMSO_2_19115_lociStitched | chrX | 56805175 | 56811038 |
| 2_MM1S_MED1_DMSO_2_811_lociStitched | chr1 | 110963171 | 110982799 |
| 1_MM1S_MED1_DMSO_2_7885_lociStitched | chr17 | 77090061 | 77097539 |
| 3_MM1S_MED1_DMSO_2_11917_lociStitched | chr3 | 13010123 | 13036559 |
| 5_MM1S_MED1_DMSO_2_2179_lociStitched | chr10 | 73677336 | 73694126 |
| 3_MM1S_MED1_DMSO_2_8045_lociStitched | chr18 | 19057373 | 19077707 |
| 1_MM1S_MED1_DMSO_2_14417_lociStitched | chr5 | 90711139 | 90716188 |
| 2_MM1S_MED1_DMSO_2_4222_lociStitched | chr12 | 88262387 | 88273597 |
| 1_MM1S_MED1_DMSO_2_1055_lociStitched | chr1 | 154210608 | 154218896 |
| 4_MM1S_MED1_DMSO_2_13888_lociStitched | chr4 | 185476602 | 185507051 |
| 5_MM1S_MED1_DMSO_2_13340_lociStitched | chr4 | 47873764 | 47901113 |
| 3_MM1S_MED1_DMSO_2_902_lociStitched | chr1 | 144093230 | 144111474 |
| 4_MM1S_MED1_DMSO_2_4375_lociStitched | chr12 | 107581795 | 107622903 |
| 3_MM1S_MED1_DMSO_2_7801_lociStitched | chr17 | 72740997 | 72755489 |
| 2_MM1S_MED1_DMSO_2_2458_lociStitched | chr10 | 112245714 | 112254934 |
| 11_MM1S_MED1_DMSO_2_14962_lociStitched | chr5 | 173243900 | 173289403 |
| 4_MM1S_MED1_DMSO_2_12387_lociStitched | chr3 | 99962343 | 99978843 |
| 1_MM1S_MED1_DMSO_2_4479_lociStitched | chr12 | 119212631 | 119215958 |
| 3_MM1S_MED1_DMSO_2_15872_lociStitched | chr6 | 106692441 | 106702198 |
| 2_MM1S_MED1_DMSO_2_4368_lociStitched | chr12 | 107478295 | 107494548 |
| 3_MM1S_MED1_DMSO_2_8359_lociStitched | chr19 | 1598817 | 1620929 |
| 5_MM1S_MED1_DMSO_2_11087_lociStitched | chr20 | 55390112 | 55408865 |
| 5_MM1S_MED1_DMSO_2_3367_lociStitched | chr11 | 110737473 | 110765459 |
| 1_MM1S_MED1_DMSO_2_17494_lociStitched | chr8 | 29685550 | 29690431 |
| 5_MM1S_MED1_DMSO_2_9346_lociStitched | chr2 | 42179512 | 42210718 |
| 9_MM1S_MED1_DMSO_2_12137_lociStitched | chr3 | 46384095 | 46413568 |
| 4_MM1S_MED1_DMSO_2_2241_lociStitched | chr10 | 80670951 | 80690429 |
| 3_MM1S_MED1_DMSO_2_18151_lociStitched | chr9 | 9596419 | 9605712 |
| 4_MM1S_MED1_DMSO_2_5951_lociStitched | chr15 | 72850107 | 72865537 |
| 6_MM1S_MED1_DMSO_2_9773_lociStitched | chr2 | 109176497 | 109219823 |
| 2_MM1S_MED1_DMSO_2_11509_lociStitched | chr22 | 25312119 | 25321438 |
| 2_MM1S_MED1_DMSO_2_13009_lociStitched | chr3 | 195504620 | 195516950 |
| 4_MM1S_MED1_DMSO_2_11609_lociStitched | chr22 | 35102731 | 35115007 |

TABLE 2-continued

Multiple Myeloma Super-enhancers. Based on Gene Build hg 18

| REGION_ID | CHROM | START | STOP |
|---|---|---|---|
| 7_MM1S_MED1_DMSO_2_5487_lociStitched | chr14 | 105217337 | 105240489 |
| 1_MM1S_MED1_DMSO_2_10174_lociStitched | chr2 | 192248312 | 192253669 |
| 3_MM1S_MED1_DMSO_2_7356_lociStitched | chr17 | 35720293 | 35737137 |
| 4_MM1S_MED1_DMSO_2_1849_lociStitched | chr10 | 7553027 | 7575263 |
| 4_MM1S_MED1_DMSO_2_16642_lociStitched | chr7 | 47479754 | 47504874 |
| 3_MM1S_MED1_DMSO_2_14100_lociStitched | chr5 | 32607763 | 32625969 |
| 5_MM1S_MED1_DMSO_2_4572_lociStitched | chr12 | 123957232 | 123991926 |
| 4_MM1S_MED1_DMSO_2_2466_lociStitched | chr10 | 112590984 | 112617972 |
| 1_MM1S_MED1_DMSO_2_11372_lociStitched | chr21 | 44484038 | 44489285 |
| 8_MM1S_MED1_DMSO_2_8848_lociStitched | chr19 | 46720121 | 46762201 |
| 2_MM1S_MED1_DMSO_2_2455_lociStitched | chr10 | 112162427 | 112174574 |
| 3_MM1S_MED1_DMSO_2_6671_lociStitched | chr16 | 66137623 | 66158813 |
| 3_MM1S_MED1_DMSO_2_19339_lociStitched | chrX | 130662431 | 130673564 |
| 2_MM1S_MED1_DMSO_2_1640_lociStitched | chr1 | 224906864 | 224919127 |
| 3_MM1S_MED1_DMSO_2_7431_lociStitched | chr17 | 39630911 | 39655723 |
| 1_MM1S_MED1_DMSO_2_8114_lociStitched | chr18 | 40512420 | 40517489 |
| 1_MM1S_MED1_DMSO_2_14692_lociStitched | chr5 | 138749622 | 138758419 |
| 3_MM1S_MED1_DMSO_2_1123_lociStitched | chr1 | 158943494 | 158980488 |
| 4_MM1S_MED1_DMSO_2_16250_lociStitched | chr6 | 157897104 | 157913718 |
| 2_MM1S_MED1_DMSO_2_17101_lociStitched | chr7 | 130440752 | 130460529 |
| 3_MM1S_MED1_DMSO_2_9135_lociStitched | chr2 | 11801032 | 11812720 |
| 3_MM1S_MED1_DMSO_2_10929_lociStitched | chr20 | 42002450 | 42018666 |
| 3_MM1S_MED1_DMSO_2_1119_lociStitched | chr1 | 158908226 | 158921742 |
| 1_MM1S_MED1_DMSO_2_3090_lociStitched | chr11 | 65380453 | 65385752 |
| 2_MM1S_MED1_DMSO_2_16369_lociStitched | chr7 | 5531468 | 5539806 |
| 5_MM1S_MED1_DMSO_2_13495_lociStitched | chr4 | 84352012 | 84381789 |
| 2_MM1S_MED1_DMSO_2_17959_lociStitched | chr8 | 129734648 | 129741973 |
| 1_MM1S_MED1_DMSO_2_5907_lociStitched | chr15 | 68174162 | 68181768 |
| 4_MM1S_MED1_DMSO_2_10987_lociStitched | chr20 | 45820090 | 45849423 |
| 2_MM1S_MED1_DMSO_2_5964_lociStitched | chr15 | 73121792 | 73127799 |
| 2_MM1S_MED1_DMSO_2_17479_lociStitched | chr8 | 29253249 | 29266444 |
| 5_MM1S_MED1_DMSO_2_18891_lociStitched | chrX | 10025533 | 10050677 |
| 2_MM1S_MED1_DMSO_2_17880_lociStitched | chr8 | 120954422 | 120969636 |
| 1_MM1S_MED1_DMSO_2_1813_lociStitched | chr10 | 3814293 | 3818876 |
| 5_MM1S_MED1_DMSO_2_9497_lociStitched | chr2 | 64716540 | 64748251 |
| 4_MM1S_MED1_DMSO_2_7748_lociStitched | chr17 | 71366025 | 71387309 |
| 6_MM1S_MED1_DMSO_2_2420_lociStitched | chr10 | 105235066 | 105265831 |
| 3_MM1S_MED1_DMSO_2_7698_lociStitched | chr17 | 68094083 | 68113162 |
| 2_MM1S_MED1_DMSO_2_18473_lociStitched | chr9 | 97295762 | 97314118 |
| 1_MM1S_MED1_DMSO_2_7313_lociStitched | chr17 | 34110323 | 34116969 |
| 7_MM1S_MED1_DMSO_2_4966_lociStitched | chr13 | 114042783 | 114062417 |
| 3_MM1S_MED1_DMSO_2_14016_lociStitched | chr5 | 6528481 | 6550072 |
| 1_MM1S_MED1_DMSO_2_10942_lociStitched | chr20 | 42704197 | 42716062 |
| 4_MM1S_MED1_DMSO_2_13987_lociStitched | chr5 | 1541550 | 1578016 |
| 3_MM1S_MED1_DMSO_2_13707_lociStitched | chr4 | 129949673 | 129960374 |
| 2_MM1S_MED1_DMSO_2_10549_lociStitched | chr2 | 238264326 | 238277907 |
| 4_MM1S_MED1_DMSO_2_19321_lociStitched | chrX | 128720479 | 128739812 |
| 3_MM1S_MED1_DMSO_2_9743_lociStitched | chr2 | 105694868 | 105718268 |
| 1_MM1S_MED1_DMSO_2_9393_lociStitched | chr2 | 47061614 | 47068522 |
| 3_MM1S_MED1_DMSO_2_10581_lociStitched | chr2 | 241152963 | 241176172 |
| 5_MM1S_MED1_DMSO_2_2158_lociStitched | chr10 | 71906942 | 71940173 |
| 3_MM1S_MED1_DMSO_2_3127_lociStitched | chr11 | 66789831 | 66814109 |
| 2_MM1S_MED1_DMSO_2_12973_lociStitched | chr3 | 188262377 | 188274985 |
| 1_MM1S_MED1_DMSO_2_14147_lociStitched | chr5 | 43072552 | 43079610 |
| 5_MM1S_MED1_DMSO_2_7714_lociStitched | chr17 | 70249246 | 70279117 |
| 2_MM1S_MED1_DMSO_2_13272_lociStitched | chr4 | 37805684 | 37812390 |
| 1_MM1S_MED1_DMSO_2_9642_lociStitched | chr2 | 86073843 | 86082122 |
| 1_MM1S_MED1_DMSO_2_13666_lociStitched | chr4 | 121888607 | 121891728 |
| 2_MM1S_MED1_DMSO_2_6598_lociStitched | chr16 | 55501343 | 55510262 |
| 4_MM1S_MED1_DMSO_2_12038_lociStitched | chr3 | 39222524 | 39251963 |
| 2_MM1S_MED1_DMSO_2_1926_lociStitched | chr10 | 15866384 | 15871377 |
| 2_MM1S_MED1_DMSO_2_5835_lociStitched | chr15 | 62961116 | 62976322 |
| 2_MM1S_MED1_DMSO_2_11661_lociStitched | chr22 | 37031196 | 37044926 |
| 1_MM1S_MED1_DMSO_2_2098_lociStitched | chr10 | 63326304 | 63335210 |
| 4_MM1S_MED1_DMSO_2_3547_lociStitched | chr11 | 128727439 | 128752307 |
| 3_MM1S_MED1_DMSO_2_12969_lociStitched | chr3 | 188185946 | 188202149 |
| 2_MM1S_MED1_DMSO_2_11345_lociStitched | chr21 | 43454397 | 43471457 |
| 3_MM1S_MED1_DMSO_2_19091_lociStitched | chrX | 52966103 | 52981642 |
| 3_MM1S_MED1_DMSO_2_8625_lociStitched | chr19 | 16041917 | 16058919 |
| 3_MM1S_MED1_DMSO_2_1534_lociStitched | chr1 | 209753487 | 209768728 |
| 3_MM1S_MED1_DMSO_2_2769_lociStitched | chr11 | 16923726 | 16943228 |

TABLE 3

| Glioblastoma Super-Enhancers. Based on Gene Build hg18 | | | |
|---|---|---|---|
| REGION_ID | CHROM | START | STOP |
| 18_U87_MED1_20020_lociStitched | chr3 | 45100470 | 45243521 |
| 12_U87_MED1_7111_lociStitched | chr12 | 64271490 | 64380497 |
| 22_U87_MED1_17388_lociStitched | chr2 | 237744314 | 237896194 |
| 8_U87_MED1_7790_lociStitched | chr12 | 126279637 | 126344656 |
| 16_U87_MED1_25966_lociStitched | chr6 | 44066339 | 44153887 |
| 20_U87_MED1_17421_lociStitched | chr2 | 237957090 | 238086756 |
| 13_U87_MED1_24508_lociStitched | chr5 | 135356769 | 135440815 |
| 5_U87_MED1_21695_lociStitched | chr3 | 195773224 | 195801953 |
| 10_U87_MED1_28029_lociStitched | chr7 | 100523787 | 100571097 |
| 6_U87_MED1_32110_lociStitched | chrX | 45479800 | 45553892 |
| U87_MED1_6148 | chr11 | 121548066 | 121570391 |
| 19_U87_MED1_15336_lociStitched | chr2 | 46879598 | 46970410 |
| 6_U87_MED1_28324_lociStitched | chr7 | 130215723 | 130260073 |
| 17_U87_MED1_28910_lociStitched | chr8 | 23203324 | 23280028 |
| 6_U87_MED1_18087_lociStitched | chr20 | 45376522 | 45424087 |
| 4_U87_MED1_5653_lociStitched | chr11 | 64940094 | 64979948 |
| 9_U87_MED1_11378_lociStitched | chr16 | 76138395 | 76189426 |
| 2_U87_MED1_19517_lociStitched | chr3 | 4992550 | 5013365 |
| 9_U87_MED1_24067_lociStitched | chr5 | 90604451 | 90646666 |
| 6_U87_MED1_24844_lociStitched | chr5 | 150121686 | 150155852 |
| 5_U87_MED1_27721_lociStitched | chr7 | 72748931 | 72774831 |
| 10_U87_MED1_20211_lociStitched | chr3 | 55151891 | 55214347 |
| 6_U87_MED1_5659_lociStitched | chr11 | 64995165 | 65033129 |
| 3_U87_MED1_19044_lociStitched | chr22 | 28920868 | 28939971 |
| 8_U87_MED1_24834_lociStitched | chr5 | 149974547 | 150020460 |
| 13_U87_MED1_21089_lociStitched | chr3 | 142532100 | 142623859 |
| 19_U87_MED1_18679_lociStitched | chr21 | 38534163 | 38647146 |
| 11_U87_MED1_28206_lociStitched | chr7 | 115938214 | 116016989 |
| 3_U87_MED1_12623_lociStitched | chr7 | 55257387 | 55278945 |
| 15_U87_MED1_7069_lociStitched | chr12 | 61372699 | 61474955 |
| U87_MED1_5680 | chr11 | 65411528 | 65428724 |
| U87_MED1_5682 | chr11 | 65433153 | 65444824 |
| U87_MED1_19439 | chr22 | 44836466 | 44869626 |
| 2_U87_MED1_3956_lociStitched | chr10 | 73689550 | 73708761 |
| 4_U87_MED1_27840_lociStitched | chr7 | 81067427 | 81109206 |
| 3_U87_MED1_32102_lociStitched | chrX | 45440741 | 45464841 |
| 5_U87_MED1_28952_lociStitched | chr8 | 24104754 | 24143595 |
| 21_U87_MED1_5003_lociStitched | chr11 | 12100995 | 12218222 |
| 11_U87_MED1_26945_lociStitched | chr6 | 158359374 | 158413800 |
| 10_U87_MED1_3959_lociStitched | chr10 | 73725225 | 73767483 |
| 5_U87_MED1_3340_lociStitched | chr10 | 17280959 | 17321940 |
| 5_U87_MED1_11362_lociStitched | chr16 | 75864680 | 75900842 |
| 4_U87_MED1_26256_lociStitched | chr6 | 86210398 | 86250125 |
| 10_U87_MED1_8940_lociStitched | chr14 | 61060615 | 61131816 |
| 7_U87_MED1_20945_lociStitched | chr3 | 128935531 | 128978089 |
| 7_U87_MED1_9371_lociStitched | chr14 | 95781765 | 95823179 |
| 7_U87_MED1_17803_lociStitched | chr20 | 29638882 | 29664742 |
| 6_U87_MED1_11435_lociStitched | chr16 | 81214233 | 81249274 |
| 8_U87_MED1_23347_lociStitched | chr5 | 14195028 | 14261996 |
| 21_U87_MED1_25200_lociStitched | chr5 | 172209298 | 172316383 |
| 6_U87_MED1_22301_lociStitched | chr4 | 74786901 | 74829347 |
| 8_U87_MED1_31350_lociStitched | chr9 | 117391466 | 117456436 |
| 2_U87_MED1_11091_lociStitched | chr16 | 55196851 | 55207509 |
| 3_U87_MED1_16900_lociStitched | chr2 | 207810793 | 207833238 |
| 14_U87_MED1_4025_lociStitched | chr10 | 76895156 | 76977932 |
| 7_U87_MED1_7635_lociStitched | chr12 | 119145594 | 119188677 |
| 15_U87_MED1_10048_lociStitched | chr15 | 65153353 | 65230563 |
| 12_U87_MED1_27257_lociStitched | chr7 | 22565898 | 22624022 |
| 1_U87_MED1_25943_lociStitched | chr6 | 43843596 | 43867854 |
| 4_U87_MED1_5758_lociStitched | chr11 | 68819807 | 68846515 |
| 3_U87_MED1_22330_lociStitched | chr4 | 75290119 | 75317605 |
| 12_U87_MED1_9569_lociStitched | chr15 | 30898025 | 30959213 |
| 14_U87_MED1_25174_lociStitched | chr5 | 172116992 | 172191454 |
| 15_U87_MED1_29037_lociStitched | chr8 | 28260823 | 28333470 |
| 5_U87_MED1_17455_lociStitched | chr2 | 238996356 | 239014679 |
| 4_U87_MED1_22339_lociStitched | chr4 | 75448510 | 75480580 |
| 2_U87_MED1_12177_lociStitched | chr17 | 35423480 | 35437302 |
| 9_U87_MED1_19052_lociStitched | chr22 | 28954187 | 29006184 |
| 5_U87_MED1_20569_lociStitched | chr3 | 100162550 | 100188309 |
| 9_U87_MED1_23186_lociStitched | chr4 | 189557679 | 189609237 |
| 11_U87_MED1_31536_lociStitched | chr9 | 129340908 | 129389008 |
| 4_U87_MED1_23355_lociStitched | chr5 | 14450202 | 14474301 |
| U87_MED1_6146 | chr11 | 121515959 | 121540976 |
| 8_U87_MED1_25729_lociStitched | chr6 | 30816520 | 30858966 |
| 10_U87_MED1_4983_lociStitched | chr11 | 12020084 | 12069159 |
| 16_U87_MED1_18248_lociStitched | chr20 | 51915427 | 52011299 |

TABLE 3-continued

Glioblastoma Super-Enhancers. Based on Gene Build hg18

| REGION_ID | CHROM | START | STOP |
|---|---|---|---|
| 2_U87_MED1_23778_lociStitched | chr5 | 64520345 | 64541781 |
| 9_U87_MED1_7528_lociStitched | chr12 | 110318731 | 110366261 |
| 1_U87_MED1_7124_lociStitched | chr12 | 64501251 | 64520825 |
| 12_U87_MED1_12963_lociStitched | chr17 | 73791501 | 73869039 |
| 11_U87_MED1_19190_lociStitched | chr22 | 35053881 | 35115041 |
| 10_U87_MED1_21395_lociStitched | chr3 | 171889621 | 171955016 |
| 8_U87_MED1_1494_lociStitched | chr1 | 94946918 | 94980513 |
| 11_U87_MED1_18744_lociStitched | chr21 | 41905622 | 41959032 |
| 5_U87_MED1_16409_lociStitched | chr2 | 160767297 | 160807533 |
| 7_U87_MED1_24782_lociStitched | chr5 | 149368846 | 149428980 |
| 11_U87_MED1_30075_lociStitched | chr8 | 128970951 | 129032504 |
| 7_U87_MED1_3670_lociStitched | chr10 | 49466581 | 49513686 |
| 11_U87_MED1_96_lociStitched | chr1 | 7976379 | 8045080 |
| 7_U87_MED1_18338_lociStitched | chr20 | 58219251 | 58265651 |
| 7_U87_MED1_24799_lociStitched | chr5 | 149623193 | 149663216 |
| 13_U87_MED1_31238_lociStitched | chr9 | 113811355 | 113877599 |
| 11_U87_MED1_4127_lociStitched | chr10 | 80528198 | 80590428 |
| 2_U87_MED1_26448_lociStitched | chr6 | 112461732 | 112477579 |
| 7_U87_MED1_28103_lociStitched | chr7 | 105771944 | 105806491 |
| 18_U87_MED1_31033_lociStitched | chr9 | 100772868 | 100889180 |
| 14_U87_MED1_30675_lociStitched | chr9 | 37974257 | 38060126 |
| 8_U87_MED1_10549_lociStitched | chr15 | 99038601 | 99089992 |
| 11_U87_MED1_9182_lociStitched | chr14 | 76439874 | 76498969 |
| 7_U87_MED1_24848_lociStitched | chr5 | 150413621 | 150465246 |
| 6_U87_MED1_23363_lociStitched | chr5 | 14492548 | 14555243 |
| 3_U87_MED1_13121_lociStitched | chr18 | 3575542 | 3597033 |
| 12_U87_MED1_24585_lociStitched | chr5 | 138995233 | 139071634 |
| 6_U87_MED1_5284_lociStitched | chr11 | 35116090 | 35159659 |
| 8_U87_MED1_3521_lociStitched | chr10 | 33284148 | 33345221 |
| 7_U87_MED1_3616_lociStitched | chr10 | 43658240 | 43708520 |
| 13_U87_MED1_9361_lociStitched | chr14 | 95621243 | 95685962 |
| 4_U87_MED1_1127_lociStitched | chr1 | 58992223 | 59025064 |
| 7_U87_MED1_12194_lociStitched | chr17 | 35693162 | 35742563 |
| 8_U87_MED1_16879_lociStitched | chr2 | 206252656 | 206308088 |
| 9_U87_MED1_8736_lociStitched | chr14 | 34901740 | 34946481 |
| 4_U87_MED1_31655_lociStitched | chr9 | 132701910 | 132727822 |
| 9_U87_MED1_28850_lociStitched | chr8 | 22269372 | 22319900 |
| 6_U87_MED1_1768_lociStitched | chr1 | 143784496 | 143840429 |
| 4_U87_MED1_103_lociStitched | chr1 | 8059282 | 8081510 |
| 7_U87_MED1_2854_lociStitched | chr1 | 222980231 | 223015835 |
| 8_U87_MED1_10117_lociStitched | chr15 | 68542055 | 68588784 |
| 7_U87_MED1_9901_lociStitched | chr15 | 58441168 | 58488832 |
| 3_U87_MED1_15883_lociStitched | chr2 | 101938979 | 101958391 |
| 3_U87_MED1_2303_lociStitched | chr1 | 181502080 | 181517873 |
| 3_U87_MED1_9993_lociStitched | chr15 | 63374614 | 63385055 |
| 5_U87_MED1_4927_lociStitched | chr11 | 10276396 | 10310109 |
| 8_U87_MED1_152_lociStitched | chr1 | 9145323 | 9194908 |
| 7_U87_MED1_9271_lociStitched | chr14 | 90758863 | 90795031 |
| 5_U87_MED1_292_lociStitched | chr1 | 16147097 | 16166359 |
| 9_U87_MED1_21428_lociStitched | chr3 | 173326232 | 173383239 |
| 3_U87_MED1_1480_lociStitched | chr1 | 94764000 | 94783945 |
| 8_U87_MED1_23764_lociStitched | chr5 | 64362972 | 64408615 |
| 3_U87_MED1_29946_lociStitched | chr8 | 123392549 | 123407278 |
| 7_U87_MED1_12906_lociStitched | chr17 | 72195710 | 72225546 |
| 8_U87_MED1_15990_lociStitched | chr2 | 113267162 | 113314982 |
| 7_U87_MED1_116_lociStitched | chr1 | 8176575 | 8201970 |
| 5_U87_MED1_3649_lociStitched | chr10 | 44783418 | 44814443 |
| U87_MED1_12057 | chr17 | 26944014 | 26950786 |
| 2_U87_MED1_28437_lociStitched | chr7 | 137207368 | 137218994 |
| 5_U87_MED1_12467_lociStitched | chr17 | 45458793 | 45498200 |
| 6_U87_MED1_7769_lociStitched | chr12 | 123954906 | 123991790 |
| 8_U87_MED1_31230_lociStitched | chr9 | 113739183 | 113777283 |
| 5_U87_MED1_31605_lociStitched | chr9 | 131283335 | 131311945 |
| 7_U87_MED1_13271_lociStitched | chr18 | 18500819 | 18546785 |
| 6_U87_MED1_11526_lociStitched | chr16 | 85154494 | 85187872 |
| 6_U87_MED1_10162_lociStitched | chr15 | 72000419 | 72046025 |
| 2_U87_MED1_23340_lociStitched | chr5 | 14085673 | 14095662 |
| 2_U87_MED1_19978_lociStitched | chr3 | 43871898 | 43892096 |
| 3_U87_MED1_6430_lociStitched | chr12 | 6511065 | 6534804 |
| 9_U87_MED1_19998_lociStitched | chr3 | 45053955 | 45084099 |
| 7_U87_MED1_16195_lociStitched | chr2 | 134284761 | 134318932 |
| 11_U87_MED1_23940_lociStitched | chr5 | 77835851 | 77885336 |
| 6_U87_MED1_27845_lociStitched | chr7 | 81142953 | 81184064 |
| 4_U87_MED1_17882_lociStitched | chr20 | 33353373 | 33372955 |
| 10_U87_MED1_28600_lociStitched | chr7 | 154610962 | 154658753 |
| 5_U87_MED1_4664_lociStitched | chr10 | 124030434 | 124058691 |

TABLE 3-continued

Glioblastoma Super-Enhancers. Based on Gene Build hg18

| REGION_ID | CHROM | START | STOP |
|---|---|---|---|
| 4_U87_MED1_31381_lociStitched | chr9 | 118068405 | 118091501 |
| 3_U87_MED1_29735_lociStitched | chr8 | 103869131 | 103893137 |
| 5_U87_MED1_10189_lociStitched | chr15 | 72475467 | 72510666 |
| 10_U87_MED1_24811_lociStitched | chr5 | 149818464 | 149877985 |
| 7_U87_MED1_30097_lociStitched | chr8 | 129248470 | 129279733 |
| 3_U87_MED1_9036_lociStitched | chr14 | 68314932 | 68333600 |
| 5_U87_MED1_20051_lociStitched | chr3 | 46104252 | 46131876 |
| 4_U87_MED1_1138_lociStitched | chr1 | 59085582 | 59122632 |
| 4_U87_MED1_15701_lociStitched | chr2 | 75667467 | 75701638 |
| 4_U87_MED1_711_lociStitched | chr1 | 33565656 | 33589393 |
| 8_U87_MED1_13446_lociStitched | chr18 | 42508896 | 42556266 |
| 10_U87_MED1_30394_lociStitched | chr9 | 3846346 | 3907818 |
| 3_U87_MED1_19433_lociStitched | chr22 | 44770633 | 44789144 |
| 8_U87_MED1_12920_lociStitched | chr17 | 72792423 | 72841736 |
| 3_U87_MED1_29401_lociStitched | chr8 | 62831256 | 62843484 |
| 8_U87_MED1_23950_lociStitched | chr5 | 77897945 | 77947772 |
| 4_U87_MED1_11532_lociStitched | chr16 | 85244100 | 85274282 |
| 3_U87_MED1_17802_lociStitched | chr20 | 29610545 | 29626036 |
| 9_U87_MED1_7003_lociStitched | chr12 | 55806899 | 55852250 |
| 9_U87_MED1_30667_lociStitched | chr9 | 37919181 | 37959597 |
| 5_U87_MED1_23475_lociStitched | chr5 | 34599305 | 34646619 |
| 9_U87_MED1_21809_lociStitched | chr4 | 5774565 | 5812219 |
| 5_U87_MED1_2484_lociStitched | chr1 | 199931838 | 199958314 |
| 2_U87_MED1_18366_lociStitched | chr20 | 60595254 | 60615120 |
| 3_U87_MED1_7103_lociStitched | chr12 | 64204208 | 64218785 |
| 2_U87_MED1_20034_lociStitched | chr3 | 45560540 | 45571271 |
| 3_U87_MED1_12304_lociStitched | chr17 | 38789690 | 38802753 |
| 5_U87_MED1_22699_lociStitched | chr4 | 123904338 | 123939922 |
| 4_U87_MED1_9736_lociStitched | chr15 | 43521877 | 43538803 |
| 7_U87_MED1_11894_lociStitched | chr17 | 16864733 | 16908403 |
| 5_U87_MED1_22347_lociStitched | chr4 | 75606560 | 75632402 |
| 7_U87_MED1_3329_lociStitched | chr10 | 17067573 | 17112416 |
| 7_U87_MED1_11080_lociStitched | chr16 | 54061119 | 54092821 |
| 6_U87_MED1_3934_lociStitched | chr10 | 73013845 | 73035645 |
| 8_U87_MED1_9304_lociStitched | chr14 | 92160646 | 92214011 |
| 8_U87_MED1_131_lociStitched | chr1 | 8851431 | 8891614 |
| 6_U87_MED1_2968_lociStitched | chr1 | 232801400 | 232834869 |
| 7_U87_MED1_4111_lociStitched | chr10 | 80355085 | 80408481 |
| 7_U87_MED1_6339_lociStitched | chr12 | 2222492 | 2249299 |
| 4_U87_MED1_26068_lociStitched | chr6 | 52475692 | 52496081 |
| 10_U87_MED1_27934_lociStitched | chr7 | 93489372 | 93537292 |
| 5_U87_MED1_3808_lociStitched | chr10 | 64315142 | 64346977 |
| 3_U87_MED1_944_lociStitched | chr1 | 44945138 | 44970174 |
| 3_U87_MED1_18034_lociStitched | chr20 | 43147144 | 43169721 |
| 3_U87_MED1_325_lociStitched | chr1 | 17094881 | 17113779 |
| 3_U87_MED1_3042_lociStitched | chr1 | 238461272 | 238489689 |
| 9_U87_MED1_1156_lociStitched | chr1 | 59361216 | 59425669 |
| 6_U87_MED1_30197_lociStitched | chr8 | 134210870 | 134248321 |
| 3_U87_MED1_32076_lociStitched | chrX | 43702439 | 43721105 |
| 8_U87_MED1_5161_lociStitched | chr1 | 27864823 | 27914163 |
| 9_U87_MED1_2459_lociStitched | chr1 | 199680258 | 199726111 |
| 4_U87_MED1_7235_lociStitched | chr12 | 74697858 | 74717726 |
| 5_U87_MED1_4730_lociStitched | chr10 | 127900118 | 127932927 |
| 6_U87_MED1_22320_lociStitched | chr4 | 75178405 | 75219573 |
| 5_U87_MED1_7127_lociStitched | chr12 | 64537567 | 64575468 |
| 4_U87_MED1_17184_lociStitched | chr2 | 226993280 | 227021635 |
| 5_U87_MED1_16908_lociStitched | chr2 | 207958570 | 207998045 |
| 5_U87_MED1_15976_lociStitched | chr2 | 113096151 | 113124471 |
| 5_U87_MED1_19506_lociStitched | chr3 | 4727890 | 4764151 |
| 1_U87_MED1_204_lociStitched | chr1 | 11889850 | 11893062 |
| 3_U87_MED1_13789_lociStitched | chr19 | 1198622 | 1219360 |
| 5_U87_MED1_4735_lociStitched | chr10 | 128052098 | 128101696 |
| 5_U87_MED1_31406_lociStitched | chr9 | 122171758 | 122206963 |
| 5_U87_MED1_9188_lociStitched | chr14 | 76558717 | 76596203 |
| 2_U87_MED1_8973_lociStitched | chr14 | 64612804 | 64614687 |
| 11_U87_MED1_18186_lociStitched | chr20 | 49369237 | 49419385 |
| 2_U87_MED1_29678_lociStitched | chr8 | 99439088 | 99452526 |
| 4_U87_MED1_5551_lociStitched | chr11 | 61478002 | 61500583 |
| 10_U87_MED1_2485_lociStitched | chr1 | 199971787 | 200011527 |
| 6_U87_MED1_3459_lociStitched | chr10 | 29949767 | 29989251 |
| 7_U87_MED1_17938_lociStitched | chr20 | 36229309 | 36280924 |
| 6_U87_MED1_21893_lociStitched | chr4 | 13498370 | 13544429 |
| 5_U87_MED1_18845_lociStitched | chr21 | 46282572 | 46307112 |
| 5_U87_MED1_28712_lociStitched | chr8 | 11343022 | 11377910 |
| 5_U87_MED1_11837_lociStitched | chr17 | 13568637 | 13595972 |
| 5_U87_MED1_26443_lociStitched | chr6 | 112399077 | 112447095 |

TABLE 3-continued

Glioblastoma Super-Enhancers. Based on Gene Build hg18

| REGION_ID | CHROM | START | STOP |
|---|---|---|---|
| 10_U87_MED1_27794_lociStitched | chr7 | 76875842 | 76933318 |
| 6_U87_MED1_3787_lociStitched | chr10 | 63974312 | 64024395 |
| 3_U87_MED1_32094_lociStitched | chrX | 45249029 | 45269337 |
| 7_U87_MED1_2818_lociStitched | chr1 | 221956329 | 221986465 |
| 1_U87_MED1_7642_lociStitched | chr12 | 119212723 | 119216302 |
| 5_U87_MED1_15994_lociStitched | chr2 | 113341276 | 113362882 |
| 5_U87_MED1_20226_lociStitched | chr3 | 55462763 | 55499466 |
| 8_U87_MED1_25357_lociStitched | chr5 | 179683140 | 179713756 |
| 10_U87_MED1_21194_lociStitched | chr3 | 150772593 | 150825135 |
| 4_U87_MED1_19522_lociStitched | chr3 | 5033023 | 5054218 |
| 4_U87_MED1_15905_lociStitched | chr2 | 105378414 | 105401351 |
| 3_U87_MED1_17219_lociStitched | chr2 | 228388427 | 228408117 |
| 2_U87_MED1_13120_lociStitched | chr18 | 3436350 | 3456896 |
| 4_U87_MED1_3990_lociStitched | chr10 | 75315563 | 75338505 |
| 4_U87_MED1_11024_lociStitched | chr16 | 49738943 | 49767162 |
| 5_U87_MED1_770_lociStitched | chr1 | 36580667 | 36626685 |
| 4_U87_MED1_719_lociStitched | chr1 | 33647773 | 33674750 |
| 3_U87_MED1_24071_lociStitched | chr5 | 90698489 | 90717110 |
| 12_U87_MED1_5468_lociStitched | chr11 | 56798699 | 56850272 |
| 4_U87_MED1_15820_lociStitched | chr2 | 99841615 | 99866659 |
| 4_U87_MED1_12059_lociStitched | chr17 | 27024805 | 27048099 |
| 4_U87_MED1_19578_lociStitched | chr3 | 10205559 | 10223302 |
| 9_U87_MED1_31314_lociStitched | chr9 | 116906615 | 116969979 |
| 5_U87_MED1_17381_lociStitched | chr2 | 237695304 | 237731727 |
| 4_U87_MED1_15023_lociStitched | chr2 | 28463256 | 28486432 |
| 6_U87_MED1_16974_lociStitched | chr2 | 216253277 | 216287004 |
| 6_U87_MED1_16311_lociStitched | chr2 | 151031128 | 151061882 |
| 6_U87_MED1_3547_lociStitched | chr10 | 33659030 | 33711377 |
| 5_U87_MED1_11814_lociStitched | chr17 | 13181474 | 13210125 |
| 4_U87_MED1_28576_lociStitched | chr7 | 151008488 | 151029657 |
| 1_U87_MED1_13124_lociStitched | chr18 | 3611922 | 3616326 |
| 8_U87_MED1_3534_lociStitched | chr10 | 33444568 | 33494188 |
| 6_U87_MED1_1871_lociStitched | chr1 | 150209432 | 150241437 |
| 2_U87_MED1_18051_lociStitched | chr20 | 43832868 | 43845622 |
| 3_U87_MED1_10146_lociStitched | chr15 | 70301493 | 70317899 |
| 7_U87_MED1_2527_lociStitched | chr1 | 201747626 | 201796040 |
| 13_U87_MED1_24272_lociStitched | chr5 | 112383768 | 112458948 |
| 5_U87_MED1_26430_lociStitched | chr6 | 112137473 | 112179561 |
| 4_U87_MED1_13429_lociStitched | chr18 | 41626488 | 41662617 |
| 6_U87_MED1_8590_lociStitched | chr13 | 113882656 | 113916801 |
| 9_U87_MED1_9551_lociStitched | chr15 | 30738592 | 30802325 |
| 6_U87_MED1_17744_lociStitched | chr20 | 23071349 | 23090627 |
| 6_U87_MED1_10416_lociStitched | chr15 | 88161556 | 88193745 |
| 3_U87_MED1_5273_lociStitched | chr11 | 35007450 | 35019639 |
| 2_U87_MED1_1556_lociStitched | chr1 | 100859494 | 100870177 |
| 4_U87_MED1_29271_lociStitched | chr8 | 49481932 | 49508141 |
| 5_U87_MED1_19225_lociStitched | chr22 | 36029312 | 36057715 |
| 5_U87_MED1_29265_lociStitched | chr8 | 49377506 | 49400335 |
| 10_U87_MED1_9028_lociStitched | chr14 | 68199644 | 68255143 |
| 8_U87_MED1_12801_lociStitched | chr17 | 67895139 | 67931773 |
| 2_U87_MED1_4101_lociStitched | chr10 | 79683341 | 79694556 |
| 5_U87_MED1_16956_lociStitched | chr2 | 215974532 | 216011850 |
| 6_U87_MED1_32082_lociStitched | chrX | 43746648 | 43786932 |
| 4_U87_MED1_18137_lociStitched | chr20 | 48353990 | 48372553 |
| 1_U87_MED1_5584_lociStitched | chr11 | 62363092 | 62367099 |
| 6_U87_MED1_15922_lociStitched | chr2 | 108226124 | 108262222 |
| 5_U87_MED1_16864_lociStitched | chr2 | 204370112 | 204385649 |
| 14_U87_MED1_16427_lociStitched | chr2 | 160916322 | 160997972 |
| 8_U87_MED1_23630_lociStitched | chr5 | 52329945 | 52369930 |
| 5_U87_MED1_17309_lociStitched | chr2 | 234814049 | 234832679 |
| U87_MED1_12055 | chr17 | 26929956 | 26934384 |
| 6_U87_MED1_23098_lociStitched | chr4 | 182794994 | 182847907 |
| 7_U87_MED1_2995_lociStitched | chr1 | 233157788 | 233200699 |
| 4_U87_MED1_4147_lociStitched | chr10 | 80745860 | 80764435 |
| 10_U87_MED1_25839_lociStitched | chr6 | 35221878 | 35273955 |
| 2_U87_MED1_3179_lociStitched | chr10 | 4794967 | 4808857 |
| 5_U87_MED1_12475_lociStitched | chr17 | 45628535 | 45655344 |
| 3_U87_MED1_28098_lociStitched | chr7 | 105697048 | 105714277 |
| 1_U87_MED1_23343_lociStitched | chr5 | 14157879 | 14165158 |
| 6_U87_MED1_20739_lociStitched | chr3 | 113836451 | 113858193 |
| 6_U87_MED1_2468_lociStitched | chr1 | 199766249 | 199799338 |
| 4_U87_MED1_4913_lociStitched | chr11 | 9730174 | 9767132 |
| 2_U87_MED1_20084_lociStitched | chr3 | 48567365 | 48579540 |
| 6_U87_MED1_28721_lociStitched | chr8 | 11390711 | 11411534 |
| 5_U87_MED1_7081_lociStitched | chr12 | 62839721 | 62868417 |
| 4_U87_MED1_23208_lociStitched | chr4 | 190929117 | 190951845 |

TABLE 3-continued

Glioblastoma Super-Enhancers. Based on Gene Build hg18

| REGION_ID | CHROM | START | STOP |
|---|---|---|---|
| 8_U87_MED1_15178_lociStitched | chr2 | 37846146 | 37884311 |
| 5_U87_MED1_9939_lociStitched | chr15 | 60965417 | 60980962 |
| 9_U87_MED1_18605_lociStitched | chr21 | 35076849 | 35141236 |
| 7_U87_MED1_9763_lociStitched | chr15 | 46746824 | 46776787 |
| 3_U87_MED1_27564_lociStitched | chr7 | 45880224 | 45893741 |
| 5_U87_MED1_28912_lociStitched | chr8 | 23294269 | 23325787 |
| 2_U87_MED1_4059_lociStitched | chr10 | 78777531 | 78788869 |
| 5_U87_MED1_23069_lociStitched | chr4 | 178139337 | 178175485 |
| 3_U87_MED1_12646_lociStitched | chr17 | 56755482 | 56771755 |
| 3_U87_MED1_16239_lociStitched | chr2 | 143331502 | 143355637 |
| 3_U87_MED1_29002_lociStitched | chr8 | 26540715 | 26557275 |
| 6_U87_MED1_29815_lociStitched | chr8 | 116499299 | 116540088 |
| 6_U87_MED1_31373_lociStitched | chr9 | 118032147 | 118053805 |
| 4_U87_MED1_1780_lociStitched | chr1 | 144138664 | 144168151 |
| 5_U87_MED1_30166_lociStitched | chr8 | 132922317 | 132943207 |
| 9_U87_MED1_30246_lociStitched | chr8 | 134963771 | 135009147 |
| 3_U87_MED1_23445_lociStitched | chr5 | 33334716 | 33357539 |
| 6_U87_MED1_17250_lociStitched | chr2 | 230173938 | 230207111 |
| 5_U87_MED1_18788_lociStitched | chr21 | 43737139 | 43761842 |
| 6_U87_MED1_26457_lociStitched | chr6 | 112629871 | 112666312 |
| 6_U87_MED1_12208_lociStitched | chr17 | 35930846 | 35971407 |
| 9_U87_MED1_28935_lociStitched | chr8 | 23632043 | 23677190 |
| 6_U87_MED1_15610_lociStitched | chr2 | 72004300 | 72031901 |
| 4_U87_MED1_28289_lociStitched | chr7 | 128254122 | 128269877 |
| 1_U87_MED1_5182_lociStitched | chr11 | 28810629 | 28817709 |
| 2_U87_MED1_18609_lociStitched | chr21 | 35174645 | 35187060 |
| 5_U87_MED1_28350_lociStitched | chr7 | 130960595 | 130990571 |
| 4_U87_MED1_22927_lociStitched | chr4 | 158071384 | 158094259 |
| 5_U87_MED1_4012_lociStitched | chr10 | 76826281 | 76861798 |
| 7_U87_MED1_379_lociStitched | chr1 | 19621887 | 19652224 |
| 6_U87_MED1_18585_lociStitched | chr21 | 34818327 | 34848489 |
| 5_U87_MED1_904_lociStitched | chr1 | 43160882 | 43182066 |
| 2_U87_MED1_15586_lociStitched | chr2 | 70676208 | 70689547 |
| 2_U87_MED1_31394_lociStitched | chr9 | 118343216 | 118354200 |
| 1_U87_MED1_23352_lociStitched | chr5 | 14316952 | 14324472 |
| 10_U87_MED1_19673_lociStitched | chr3 | 14426598 | 14490180 |
| 6_U87_MED1_4067_lociStitched | chr10 | 78929913 | 78962884 |
| 4_U87_MED1_29950_lociStitched | chr8 | 123509564 | 123529619 |
| 4_U87_MED1_31528_lociStitched | chr9 | 129297192 | 129326262 |
| 4_U87_MED1_20561_lociStitched | chr3 | 100091920 | 100125071 |
| 5_U87_MED1_28581_lociStitched | chr7 | 151055255 | 151084698 |
| 5_U87_MED1_26426_lociStitched | chr6 | 111980027 | 112035051 |
| 2_U87_MED1_18956_lociStitched | chr22 | 23149440 | 23163217 |
| 2_U87_MED1_1656_lociStitched | chr1 | 112077002 | 112088768 |
| 4_U87_MED1_15603_lociStitched | chr2 | 71956835 | 71971756 |
| 3_U87_MED1_30321_lociStitched | chr8 | 145079732 | 145099991 |
| 3_U87_MED1_233_lociStitched | chr1 | 12575481 | 12603692 |
| 6_U87_MED1_28749_lociStitched | chr8 | 13254372 | 13279984 |
| 7_U87_MED1_1977_lociStitched | chr1 | 154332675 | 154367183 |
| 2_U87_MED1_18293_lociStitched | chr20 | 56022630 | 56028783 |
| 9_U87_MED1_886_lociStitched | chr1 | 41966619 | 42023301 |
| 6_U87_MED1_16981_lociStitched | chr2 | 216300355 | 216347664 |
| 6_U87_MED1_28927_lociStitched | chr8 | 23451758 | 23481764 |
| 1_U87_MED1_30073_lociStitched | chr8 | 128932139 | 128937025 |
| 5_U87_MED1_19816_lociStitched | chr3 | 27537533 | 27571776 |
| 7_U87_MED1_7805_lociStitched | chr12 | 126597650 | 126639572 |
| 5_U87_MED1_25946_lociStitched | chr6 | 43985976 | 44003858 |
| 3_U87_MED1_28109_lociStitched | chr7 | 105844701 | 105854365 |
| 2_U87_MED1_9252_lociStitched | chr14 | 89810151 | 89818908 |
| 4_U87_MED1_27267_lociStitched | chr7 | 22723409 | 22739542 |
| 13_U87_MED1_28793_lociStitched | chr8 | 19068482 | 19131291 |
| 6_U87_MED1_5481_lociStitched | chr11 | 56930199 | 56959561 |
| 2_U87_MED1_27568_lociStitched | chr7 | 45915902 | 45931369 |
| 6_U87_MED1_4303_lociStitched | chr10 | 95208065 | 95226275 |
| 7_U87_MED1_7132_lociStitched | chr12 | 64596525 | 64639788 |
| 6_U87_MED1_16065_lociStitched | chr2 | 121175738 | 121225198 |
| U87_MED1_14366 | chr19 | 47304243 | 47311641 |
| 7_U87_MED1_18808_lociStitched | chr21 | 43994975 | 44024520 |
| 2_U87_MED1_5008_lociStitched | chr11 | 12259582 | 12267357 |
| 4_U87_MED1_26112_lociStitched | chr6 | 56306428 | 56344388 |
| 2_U87_MED1_3174_lociStitched | chr10 | 4694138 | 4705791 |
| 7_U87_MED1_17815_lociStitched | chr20 | 29747030 | 29779683 |
| 4_U87_MED1_8309_lociStitched | chr13 | 79502139 | 79529052 |
| 8_U87_MED1_15724_lociStitched | chr2 | 84968849 | 85007114 |
| 5_U87_MED1_24412_lociStitched | chr5 | 131448786 | 131468778 |
| 6_U87_MED1_3854_lociStitched | chr10 | 69512331 | 69537255 |

TABLE 3-continued

Glioblastoma Super-Enhancers. Based on Gene Build hg18

| REGION_ID | CHROM | START | STOP |
|---|---|---|---|
| 4_U87_MED1_14415_lociStitched | chr19 | 49931469 | 49950265 |
| 5_U87_MED1_14037_lociStitched | chr19 | 13121190 | 13144815 |
| 4_U87_MED1_7978_lociStitched | chr13 | 32722777 | 32758954 |
| 6_U87_MED1_8934_lociStitched | chr14 | 60998858 | 61027173 |
| 1_U87_MED1_31355_lociStitched | chr9 | 117490731 | 117497452 |
| 4_U87_MED1_16010_lociStitched | chr2 | 113713570 | 113730597 |
| 8_U87_MED1_29905_lociStitched | chr8 | 120625584 | 120684952 |
| 1_U87_MED1_12621_lociStitched | chr17 | 55214356 | 55220009 |
| 4_U87_MED1_18033_lociStitched | chr20 | 43105683 | 43130852 |
| 1_U87_MED1_14566_lociStitched | chr19 | 56760348 | 56770942 |
| 3_U87_MED1_6635_lociStitched | chr12 | 26157496 | 26179828 |
| 10_U87_MED1_26800_lociStitched | chr6 | 148859778 | 148930005 |
| 11_U87_MED1_3404_lociStitched | chr10 | 24761351 | 24796199 |
| U87_MED1_6149 | chr11 | 121571509 | 121574883 |
| 4_U87_MED1_30210_lociStitched | chr8 | 134368437 | 134385618 |
| 6_U87_MED1_1544_lociStitched | chr1 | 99882905 | 99924721 |
| 5_U87_MED1_12392_lociStitched | chr17 | 42688819 | 42727303 |
| 8_U87_MED1_20455_lociStitched | chr3 | 72114549 | 72164267 |
| 9_U87_MED1_28371_lociStitched | chr7 | 133767195 | 133816793 |
| 4_U87_MED1_1833_lociStitched | chr1 | 148842282 | 148859888 |
| 1_U87_MED1_16194_lociStitched | chr2 | 134260935 | 134266764 |
| 5_U87_MED1_3298_lociStitched | chr10 | 14467377 | 14497715 |
| 5_U87_MED1_19494_lociStitched | chr3 | 4417975 | 4444229 |
| 5_U87_MED1_23525_lociStitched | chr5 | 37806374 | 37829663 |
| 7_U87_MED1_20638_lociStitched | chr3 | 103127775 | 103167026 |
| 5_U87_MED1_15026_lociStitched | chr2 | 28518271 | 28546447 |
| 5_U87_MED1_24346_lociStitched | chr5 | 121505170 | 121548141 |
| 1_U87_MED1_72_lociStitched | chr1 | 7279930 | 7284880 |
| 2_U87_MED1_22344_lociStitched | chr4 | 75583830 | 75590802 |
| 2_U87_MED1_19612_lociStitched | chr3 | 11295015 | 11308874 |
| 5_U87_MED1_6644_lociStitched | chr12 | 26315522 | 26344028 |
| 4_U87_MED1_18578_lociStitched | chr21 | 34262111 | 34276116 |
| 3_U87_MED1_16960_lociStitched | chr2 | 216100277 | 216111305 |
| 3_U87_MED1_11901_lociStitched | chr17 | 16984314 | 17001391 |
| 3_U87_MED1_5664_lociStitched | chr11 | 65079515 | 65090536 |
| 4_U87_MED1_14346_lociStitched | chr19 | 46416158 | 46427894 |
| 2_U87_MED1_24022_lociStitched | chr5 | 86448382 | 86461105 |
| 3_U87_MED1_12721_lociStitched | chr17 | 61694793 | 61709067 |
| 6_U87_MED1_24200_lociStitched | chr5 | 106725129 | 106753981 |
| 11_U87_MED1_25306_lociStitched | chr5 | 177709555 | 177748817 |
| 7_U87_MED1_13705_lociStitched | chr18 | 66175119 | 66216988 |
| 5_U87_MED1_14892_lociStitched | chr2 | 20229043 | 20250537 |
| 5_U87_MED1_358_lociStitched | chr1 | 18060509 | 18078661 |
| 8_U87_MED1_29868_lociStitched | chr8 | 119059307 | 119101868 |
| 2_U87_MED1_31353_lociStitched | chr9 | 117468982 | 117476962 |
| 4_U87_MED1_26509_lociStitched | chr6 | 117867944 | 117880133 |
| 4_U87_MED1_6791_lociStitched | chr12 | 45948501 | 45963507 |
| 1_U87_MED1_7316_lociStitched | chr12 | 88263372 | 88272888 |
| 1_U87_MED1_28454_lociStitched | chr7 | 139014545 | 139019742 |
| 3_U87_MED1_29676_lociStitched | chr8 | 99413377 | 99423302 |
| 6_U87_MED1_23651_lociStitched | chr5 | 52728355 | 52762900 |
| 4_U87_MED1_29126_lociStitched | chr8 | 32294513 | 32321547 |
| 1_U87_MED1_16937_lociStitched | chr2 | 213414737 | 213420189 |
| 5_U87_MED1_9017_lociStitched | chr14 | 68071320 | 68092309 |
| 2_U87_MED1_7050_lociStitched | chr12 | 61281616 | 61290216 |
| 2_U87_MED1_8479_lociStitched | chr13 | 105600869 | 105608876 |
| 3_U87_MED1_28991_lociStitched | chr8 | 26361671 | 26378373 |
| 9_U87_MED1_3200_lociStitched | chr10 | 5566940 | 5627226 |
| 3_U87_MED1_30976_lociStitched | chr9 | 96662387 | 96672240 |
| 4_U87_MED1_29291_lociStitched | chr8 | 49966143 | 50006378 |
| 6_U87_MED1_9106_lociStitched | chr14 | 72173702 | 72203999 |
| 8_U87_MED1_16377_lociStitched | chr2 | 158024751 | 158054345 |
| 5_U87_MED1_21864_lociStitched | chr4 | 9775313 | 9798168 |
| 4_U87_MED1_11370_lociStitched | chr16 | 75998735 | 76031950 |
| 7_U87_MED1_15218_lociStitched | chr2 | 39560078 | 39595092 |
| 8_U87_MED1_12696_lociStitched | chr17 | 59756987 | 59812906 |
| 8_U87_MED1_25005_lociStitched | chr5 | 159233084 | 159273365 |
| 2_U87_MED1_14996_lociStitched | chr2 | 27872924 | 27887411 |
| 1_U87_MED1_9389_lociStitched | chr14 | 96712814 | 96717531 |
| 5_U87_MED1_27903_lociStitched | chr7 | 92088104 | 92112431 |
| 7_U87_MED1_4679_lociStitched | chr10 | 124239479 | 124271216 |
| 6_U87_MED1_30005_lociStitched | chr8 | 125807278 | 125854903 |
| 6_U87_MED1_28456_lociStitched | chr7 | 139069397 | 139084495 |
| 2_U87_MED1_24155_lociStitched | chr5 | 97670802 | 97679322 |
| 8_U87_MED1_21597_lociStitched | chr3 | 189462566 | 189498548 |
| 6_U87_MED1_11827_lociStitched | chr17 | 13364635 | 13408579 |

TABLE 3-continued

Glioblastoma Super-Enhancers. Based on Gene Build hg18

| REGION_ID | CHROM | START | STOP |
|---|---|---|---|
| 7_U87_MED1_3680_lociStitched | chr10 | 50039199 | 50063569 |
| 2_U87_MED1_19061_lociStitched | chr22 | 29134450 | 29153278 |
| 3_U87_MED1_23518_lociStitched | chr5 | 37750719 | 37760798 |
| 3_U87_MED1_7310_lociStitched | chr12 | 88073577 | 88084969 |
| 1_U87_MED1_13590_lociStitched | chr18 | 54176974 | 54185409 |
| 8_U87_MED1_8053_lociStitched | chr13 | 42279138 | 42321467 |
| 4_U87_MED1_12184_lociStitched | chr17 | 35505423 | 35524108 |
| 4_U87_MED1_13264_lociStitched | chr18 | 18384075 | 18398874 |
| 2_U87_MED1_9121_lociStitched | chr14 | 72995992 | 73005780 |
| 1_U87_MED1_318_lociStitched | chr1 | 16712459 | 16713704 |
| 4_U87_MED1_28428_lociStitched | chr7 | 136991184 | 137032443 |
| 1_U87_MED1_21899_lociStitched | chr4 | 13595377 | 13602846 |
| 6_U87_MED1_1236_lociStitched | chr1 | 66500300 | 66532014 |
| 2_U87_MED1_23649_lociStitched | chr5 | 52691426 | 52701566 |
| 2_U87_MED1_1146_lociStitched | chr1 | 59278815 | 59285007 |
| 3_U87_MED1_4738_lociStitched | chr10 | 128136077 | 128148428 |
| 1_U87_MED1_16895_lociStitched | chr2 | 207733794 | 207741019 |
| U87_MED1_6147 | chr11 | 121541171 | 121547835 |
| 8_U87_MED1_18611_lociStitched | chr21 | 35259187 | 35300591 |
| 5_U87_MED1_21690_lociStitched | chr3 | 195673864 | 195696713 |
| 6_U87_MED1_24681_lociStitched | chr5 | 142535854 | 142577824 |
| 4_U87_MED1_25215_lociStitched | chr5 | 172809327 | 172835222 |
| 4_U87_MED1_14706_lociStitched | chr2 | 9220694 | 9250055 |
| 5_U87_MED1_17204_lociStitched | chr2 | 227939599 | 227962404 |
| 8_U87_MED1_28194_lociStitched | chr7 | 115849254 | 115893839 |
| 5_U87_MED1_19772_lociStitched | chr3 | 23665020 | 23703368 |
| 3_U87_MED1_15004_lociStitched | chr2 | 28029902 | 28039153 |
| 4_U87_MED1_106_lociStitched | chr1 | 8103590 | 8124963 |
| 5_U87_MED1_817_lociStitched | chr1 | 39625358 | 39648692 |
| 6_U87_MED1_28612_lociStitched | chr7 | 154678056 | 154722945 |
| 7_U87_MED1_432_lociStitched | chr1 | 21495634 | 21538118 |
| 2_U87_MED1_31267_lociStitched | chr9 | 115421719 | 115435645 |
| 7_U87_MED1_12576_lociStitched | chr17 | 53290132 | 53326319 |
| 6_U87_MED1_19801_lociStitched | chr3 | 25588763 | 25621509 |
| 3_U87_MED1_27050_lociStitched | chr7 | 183514 | 197682 |
| 9_U87_MED1_14480_lociStitched | chr19 | 52127006 | 52186848 |
| 6_U87_MED1_19418_lociStitched | chr22 | 44358335 | 44388085 |
| 2_U87_MED1_30163_lociStitched | chr8 | 132894337 | 132909622 |
| U87_MED1_14367 | chr19 | 47316482 | 47321267 |
| 4_U87_MED1_12273_lociStitched | chr17 | 37922830 | 37933478 |
| 5_U87_MED1_24689_lociStitched | chr5 | 142592522 | 142623091 |
| 4_U87_MED1_20269_lociStitched | chr3 | 58004870 | 58021097 |
| 3_U87_MED1_27523_lociStitched | chr7 | 43645607 | 43666145 |
| 1_U87_MED1_17177_lociStitched | chr2 | 226687043 | 226693005 |
| 2_U87_MED1_6543_lociStitched | chr12 | 13239108 | 13252365 |
| 5_U87_MED1_17087_lociStitched | chr2 | 220013772 | 220043266 |
| 1_U87_MED1_30069_lociStitched | chr8 | 128815091 | 128825309 |
| 4_U87_MED1_29371_lociStitched | chr8 | 59816874 | 59844700 |
| 1_U87_MED1_6537_lociStitched | chr12 | 13141485 | 13148287 |
| 7_U87_MED1_5290_lociStitched | chr11 | 35188819 | 35225440 |
| 2_U87_MED1_27570_lociStitched | chr7 | 45982964 | 45992590 |
| 2_U87_MED1_14283_lociStitched | chr19 | 43180211 | 43188202 |
| 4_U87_MED1_15878_lociStitched | chr2 | 101801067 | 101827913 |
| 7_U87_MED1_3818_lociStitched | chr10 | 64389081 | 64435800 |
| 1_U87_MED1_1809_lociStitched | chr1 | 148122343 | 148127505 |
| 7_U87_MED1_4527_lociStitched | chr10 | 112142380 | 112177089 |
| 3_U87_MED1_779_lociStitched | chr1 | 37709463 | 37726142 |
| 3_U87_MED1_28080_lociStitched | chr7 | 104399029 | 104413643 |
| 8_U87_MED1_18902_lociStitched | chr22 | 19188215 | 19237227 |
| 2_U87_MED1_16544_lociStitched | chr2 | 173720790 | 173735078 |
| 3_U87_MED1_14022_lociStitched | chr19 | 12749117 | 12766578 |
| 4_U87_MED1_1829_lociStitched | chr1 | 148799756 | 148819583 |
| 3_U87_MED1_1539_lociStitched | chr1 | 99827254 | 99845083 |
| 3_U87_MED1_4484_lociStitched | chr10 | 106077029 | 106101948 |
| 5_U87_MED1_30974_lociStitched | chr9 | 96582128 | 96608518 |
| 5_U87_MED1_8539_lociStitched | chr13 | 109840351 | 109863235 |
| 2_U87_MED1_21146_lociStitched | chr3 | 147358174 | 147368300 |
| 3_U87_MED1_13125_lociStitched | chr18 | 3638374 | 3656877 |
| 6_U87_MED1_24416_lociStitched | chr5 | 131578682 | 131630139 |
| 6_U87_MED1_27818_lociStitched | chr7 | 80166238 | 80194389 |
| 4_U87_MED1_31023_lociStitched | chr9 | 100662763 | 100685315 |
| 2_U87_MED1_15229_lociStitched | chr2 | 40176624 | 40187049 |

TABLE 4

| SCLC Super-Enhancers Based on Gene Build hg 18 | | | |
|---|---|---|---|
| REGION_ID | CHROM | START | STOP |
| 1__H2171__MED1__1__1640__lociStitched | chr12 | 6920935 | 6927602 |
| 3__H2171__MED1__1__4743__lociStitched | chr20 | 20467079 | 20497912 |
| 7__H2171__MED1__1__1324__lociStitched | chr11 | 44999379 | 45032693 |
| 7__H2171__MED1__1__4739__lociStitched | chr20 | 20368291 | 20422337 |
| 3__H2171__MED1__1__4728__lociStitched | chr20 | 20127551 | 20146821 |
| 5__H2171__MED1__1__2525__lociStitched | chr14 | 100006544 | 100041089 |
| 10__H2171__MED1__1__1318__lociStitched | chr11 | 44914282 | 44976798 |
| 7__H2171__MED1__1__3367__lociStitched | chr17 | 52974161 | 53020737 |
| 5__H2171__MED1__1__2568__lociStitched | chr14 | 105386944 | 105407220 |
| 4__H2171__MED1__1__2193__lociStitched | chr13 | 70984696 | 70997790 |
| 4__H2171__MED1__1__1411__lociStitched | chr11 | 65001189 | 65034088 |
| 5__H2171__MED1__1__2727__lociStitched | chr15 | 67058222 | 67081109 |
| 4__H2171__MED1__1__4448__lociStitched | chr2 | 182187487 | 182216832 |
| 2__H2171__MED1__1__3306__lociStitched | chr17 | 38792864 | 38802484 |
| 7__H2171__MED1__1__3117__lociStitched | chr16 | 84027236 | 84077758 |
| 4__H2171__MED1__1__2523__lociStitched | chr14 | 99952877 | 99984071 |
| 4__H2171__MED1__1__6398__lociStitched | chr6 | 20798985 | 20817496 |
| 1__H2171__MED1__1__5368__lociStitched | chr3 | 73242222 | 73243091 |
| 2__H2171__MED1__1__1409__lociStitched | chr11 | 64938799 | 64950566 |
| 10__H2171__MED1__1__5063__lociStitched | chr22 | 28420926 | 28471660 |
| 3__H2171__MED1__1__1518__lociStitched | chr11 | 110675092 | 110687227 |
| 2__H2171__MED1__1__106__lociStitched | chr1 | 17094879 | 17105111 |
| 7__H2171__MED1__1__370__lociStitched | chr1 | 61124688 | 61164318 |
| 3__H2171__MED1__1__4670__lociStitched | chr20 | 5763423 | 5778470 |
| 3__H2171__MED1__1__2458__lociStitched | chr14 | 80493803 | 80524114 |
| 2__H2171__MED1__1__2703__lociStitched | chr15 | 63374895 | 63384854 |
| 2__H2171__MED1__1__196__lociStitched | chr1 | 27718317 | 27729348 |
| 1__H2171__MED1__1__1626__lociStitched | chr12 | 1909405 | 1917933 |
| 1__H2171__MED1__1__2022__lociStitched | chr12 | 119212791 | 119216166 |
| 7__H2171__MED1__1__2994__lociStitched | chr16 | 48115499 | 48154218 |
| 1__H2171__MED1__1__1385__lociStitched | chr11 | 62364199 | 62367040 |
| 3__H2171__MED1__1__355__lociStitched | chr1 | 60460911 | 60473852 |
| 8__H2171__MED1__1__4077__lociStitched | chr2 | 50900527 | 50957040 |
| 3__H2171__MED1__1__4992__lociStitched | chr21 | 45354314 | 45373451 |
| 3__H2171__MED1__1__4776__lociStitched | chr20 | 29744744 | 29765111 |
| 1__H2171__MED1__1__86__lociStitched | chr1 | 11890040 | 11892976 |
| 1__H2171__MED1__1__4772__lociStitched | chr20 | 29655198 | 29660784 |
| 1__H2171__MED1__1__1806__lociStitched | chr12 | 55914077 | 55924333 |
| 6__H2171__MED1__1__4832__lociStitched | chr20 | 44860383 | 44878078 |
| 7__H2171__MED1__1__2352__lociStitched | chr14 | 54625929 | 54653893 |
| 4__H2171__MED1__1__2589__lociStitched | chr15 | 29345063 | 29360788 |
| 9__H2171__MED1__1__1076__lociStitched | chr10 | 80658480 | 80712619 |
| 2__H2171__MED1__1__6438__lociStitched | chr6 | 26263284 | 26281349 |
| 5__H2171__MED1__1__4748__lociStitched | chr20 | 20518980 | 20554248 |
| 3__H2171__MED1__1__1797__lociStitched | chr12 | 53731066 | 53749016 |
| 5__H2171__MED1__1__259__lociStitched | chr1 | 41603873 | 41629260 |
| 2__H2171__MED1__1__4451__lociStitched | chr2 | 182245805 | 182255349 |
| 7__H2171__MED1__1__4066__lociStitched | chr2 | 50831888 | 50874042 |
| 3__H2171__MED1__1__1331__lociStitched | chr11 | 45063502 | 45081811 |
| 3__H2171__MED1__1__7960__lociStitched | chr9 | 131283833 | 131300537 |
| 1__H2171__MED1__1__3376__lociStitched | chr17 | 54062985 | 54065019 |
| 2__H2171__MED1__1__3964__lociStitched | chr2 | 8734984 | 8744081 |
| 1__H2171__MED1__1__844__lociStitched | chr1 | 232925154 | 232930496 |
| 2__H2171__MED1__1__3925__lociStitched | chr2 | 2305821 | 2317044 |
| 1__H2171__MED1__1__7716__lociStitched | chr9 | 72222711 | 72226329 |
| 1__H2171__MED1__1__3377__lociStitched | chr17 | 54090881 | 54092427 |
| 1__H2171__MED1__1__2879__lociStitched | chr16 | 2456826 | 2462820 |
| 3__H2171__MED1__1__2486__lociStitched | chr14 | 90046046 | 90059450 |
| 3__H2171__MED1__1__6363__lociStitched | chr6 | 17580996 | 17600893 |
| 4__H2171__MED1__1__2646__lociStitched | chr15 | 44378691 | 44396308 |
| 3__H2171__MED1__1__7981__lociStitched | chr9 | 133669354 | 133683692 |
| 5__H2171__MED1__1__7401__lociStitched | chr8 | 63107445 | 63135528 |
| 2__H2171__MED1__1__873__lociStitched | chr1 | 241942356 | 241953358 |
| 1__H2171__MED1__1__1285__lociStitched | chr11 | 31851717 | 31855125 |
| 4__H2171__MED1__1__7215__lociStitched | chr7 | 127256053 | 127272711 |
| 4__H2171__MED1__1__2597__lociStitched | chr15 | 29404315 | 29442687 |
| 2__H2171__MED1__1__4761__lociStitched | chr20 | 24646465 | 24652204 |
| 3__H2171__MED1__1__4781__lociStitched | chr20 | 30575765 | 30589140 |
| 2__H2171__MED1__1__3111__lociStitched | chr16 | 83975326 | 83989531 |
| 4__H2171__MED1__1__488__lociStitched | chr1 | 116596631 | 116613122 |
| 3__H2171__MED1__1__7399__lociStitched | chr8 | 62993333 | 63023912 |
| 4__H2171__MED1__1__4597__lociStitched | chr2 | 232245138 | 232257967 |
| 5__H2171__MED1__1__1703__lociStitched | chr12 | 28479296 | 28497904 |
| 4__H2171__MED1__1__8014__lociStitched | chr9 | 136814438 | 136833329 |
| 2__H2171__MED1__1__2533__lociStitched | chr14 | 100108519 | 100126673 |
| 5__H2171__MED1__1__6671__lociStitched | chr6 | 112078789 | 112091156 |

TABLE 4-continued

SCLC Super-Enhancers Based on Gene Build hg 18

| REGION_ID | CHROM | START | STOP |
|---|---|---|---|
| 3__H2171__MED1__1__6930__lociStitched | chr7 | 31684707 | 31699272 |
| 2__H2171__MED1__1__277__lociStitched | chr1 | 44959548 | 44969924 |
| 1__H2171__MED1__1__4770__lociStitched | chr20 | 29623515 | 29626066 |
| 3__H2171__MED1__1__3229__lociStitched | chr17 | 18824205 | 18838508 |
| 5__H2171__MED1__1__7373__lociStitched | chr8 | 53305190 | 53330760 |
| 2__H2171__MED1__1__4445__lociStitched | chr2 | 182146929 | 182160614 |
| 5__H2171__MED1__1__6182__lociStitched | chr5 | 142369672 | 142397549 |
| 3__H2171__MED1__1__3109__lociStitched | chr16 | 83939477 | 83957133 |
| 1__H2171__MED1__1__6436__lociStitched | chr6 | 26230266 | 26234969 |
| 2__H2171__MED1__1__5573__lociStitched | chr3 | 171666644 | 171672601 |
| 4__H2171__MED1__1__7990__lociStitched | chr9 | 133870805 | 133889409 |
| 7__H2171__MED1__1__324__lociStitched | chr1 | 54535842 | 54595884 |
| 3__H2171__MED1__1__4733__lociStitched | chr20 | 20330857 | 20340022 |
| 1__H2171__MED1__1__1286__lociStitched | chr11 | 31970692 | 31975143 |
| 3__H2171__MED1__1__6477__lociStitched | chr6 | 33819339 | 33828849 |
| 4__H2171__MED1__1__5144__lociStitched | chr22 | 41520431 | 41540832 |
| 2__H2171__MED1__1__5576__lociStitched | chr3 | 171727766 | 171734092 |
| 3__H2171__MED1__1__7552__lociStitched | chr8 | 125856085 | 125872149 |
| 3__H2171__MED1__1__7535__lociStitched | chr8 | 123754555 | 123765925 |
| 3__H2171__MED1__1__5948__lociStitched | chr5 | 14793111 | 14810119 |
| 2__H2171__MED1__1__5868__lociStitched | chr4 | 141377946 | 141394403 |
| 2__H2171__MED1__1__1526__lociStitched | chr11 | 110802193 | 110813715 |
| 1__H2171__MED1__1__3506__lociStitched | chr17 | 75396929 | 75402414 |
| 4__H2171__MED1__1__4283__lociStitched | chr2 | 134996095 | 135011003 |
| 3__H2171__MED1__1__6663__lociStitched | chr6 | 111978600 | 111995752 |
| 3__H2171__MED1__1__858__lociStitched | chr1 | 235546011 | 235556631 |
| 1__H2171__MED1__1__3207__lociStitched | chr17 | 8016708 | 8018589 |
| 4__H2171__MED1__1__303__lociStitched | chr1 | 53346865 | 53379175 |
| 3__H2171__MED1__1__6854__lociStitched | chr7 | 3273583 | 3282459 |
| 4__H2171__MED1__1__2201__lociStitched | chr13 | 71269244 | 71287635 |
| 2__H2171__MED1__1__5514__lociStitched | chr3 | 141542495 | 141547705 |
| 1__H2171__MED1__1__102__lociStitched | chr1 | 16712502 | 16713836 |
| 1__H2171__MED1__1__3304__lociStitched | chr17 | 38747760 | 38749588 |
| 4__H2171__MED1__1__3851__lociStitched | chr19 | 43240289 | 43257408 |
| 3__H2171__MED1__1__7984__lociStitched | chr9 | 133750060 | 133767255 |
| 2__H2171__MED1__1__2593__lociStitched | chr15 | 29374833 | 29382092 |
| 4__H2171__MED1__1__1632__lociStitched | chr12 | 3191844 | 3208689 |
| 3__H2171__MED1__1__613__lociStitched | chr1 | 181446125 | 181455812 |
| 1__H2171__MED1__1__515__lociStitched | chr1 | 147489769 | 147491715 |
| 1__H2171__MED1__1__7564__lociStitched | chr8 | 127859208 | 127871721 |
| 2__H2171__MED1__1__4141__lociStitched | chr2 | 70212694 | 70224525 |
| 1__H2171__MED1__1__3928__lociStitched | chr2 | 2827367 | 2830692 |
| 3__H2171__MED1__1__3104__lociStitched | chr16 | 83865721 | 83879079 |
| 3__H2171__MED1__1__7998__lociStitched | chr9 | 134078841 | 134097047 |
| 3__H2171__MED1__1__7465__lociStitched | chr8 | 93687205 | 93693913 |
| 3__H2171__MED1__1__2733__lociStitched | chr15 | 67212499 | 67237556 |
| 4__H2171__MED1__1__2715__lociStitched | chr15 | 64230622 | 64250211 |
| 2__H2171__MED1__1__1770__lociStitched | chr12 | 48729670 | 48733984 |
| 5__H2171__MED1__1__5251__lociStitched | chr3 | 16817691 | 16841285 |
| 2__H2171__MED1__1__8026__lociStitched | chr9 | 137161098 | 137170211 |
| 4__H2171__MED1__1__5775__lociStitched | chr4 | 80519421 | 80536721 |
| 3__H2171__MED1__1__4835__lociStitched | chr20 | 45030700 | 45042538 |
| 2__H2171__MED1__1__5461__lociStitched | chr3 | 127738334 | 127747382 |
| 1__H2171__MED1__1__3360__lociStitched | chr17 | 52949374 | 52952330 |
| 3__H2171__MED1__1__4792__lociStitched | chr20 | 31606072 | 31629076 |
| 3__H2171__MED1__1__5099__lociStitched | chr22 | 36154719 | 36175974 |
| 3__H2171__MED1__1__3453__lociStitched | chr17 | 69839454 | 69850658 |
| 2__H2171__MED1__1__606__lociStitched | chr1 | 180846204 | 180855565 |
| 3__H2171__MED1__1__2977__lociStitched | chr16 | 47549993 | 47564543 |
| 5__H2171__MED1__1__5509__lociStitched | chr3 | 141387464 | 141408827 |
| 4__H2171__MED1__1__6832__lociStitched | chr7 | 1281279 | 1305738 |
| 3__H2171__MED1__1__7419__lociStitched | chr8 | 64128807 | 64152294 |
| 3__H2171__MED1__1__392__lociStitched | chr1 | 67883445 | 67891831 |
| 3__H2171__MED1__1__7851__lociStitched | chr9 | 111073312 | 111081518 |
| 1__H2171__MED1__1__3482__lociStitched | chr17 | 73307672 | 73311962 |
| 1__H2171__MED1__1__677__lociStitched | chr1 | 200341028 | 200344953 |
| 4__H2171__MED1__1__2770__lociStitched | chr15 | 72303789 | 72325673 |
| 1__H2171__MED1__1__1390__lociStitched | chr11 | 63440196 | 63445356 |
| 5__H2171__MED1__1__5682__lociStitched | chr4 | 8071726 | 8098132 |
| 2__H2171__MED1__1__358__lociStitched | chr1 | 60514461 | 60520511 |
| 2__H2171__MED1__1__8028__lociStitched | chr9 | 137386784 | 137396443 |
| 4__H2171__MED1__1__4955__lociStitched | chr21 | 38139981 | 38165165 |
| 6__H2171__MED1__1__1142__lociStitched | chr10 | 112592513 | 112615109 |
| 4__H2171__MED1__1__672__lociStitched | chr1 | 200253434 | 200274407 |
| 2__H2171__MED1__1__1016__lociStitched | chr10 | 73690165 | 73706428 |
| 3__H2171__MED1__1__5762__lociStitehed | chr4 | 80338728 | 80352494 |

TABLE 4-continued

SCLC Super-Enhancers Based on Gene Build hg 18

| REGION_ID | CHROM | START | STOP |
|---|---|---|---|
| 2__H2171__MED1__1__6852__lociStitched | chr7 | 3187356 | 3195840 |
| 2__H2171__MED1__1__4985__lociStitched | chr21 | 44518734 | 44524811 |
| 3__H2171__MED1__1__4943__lociStitched | chr21 | 33430682 | 33447308 |
| 1__H2171__MED1__1__3368__lociStitched | chr17 | 53035354 | 53040644 |
| 4__H2171__MED1__1__2427__lociStitched | chr14 | 76442631 | 76461700 |
| 4__H2171__MED1__1__4558__lociStitched | chr2 | 217169924 | 217196187 |
| 3__H2171__MED1__1__7744__lociStitched | chr9 | 85109090 | 85122979 |
| 5__H2171__MED1__1__1691__lociStitched | chr12 | 28264210 | 28281514 |
| 3__H2171__MED1__1__2892__lociStitched | chr16 | 11047692 | 11059849 |
| 2__H2171__MED1__1__4899__lociStitched | chr20 | 60880400 | 60885360 |
| 1__H2171__MED1__1__7947__lociStitched | chr9 | 129461873 | 129464518 |
| 2__H2171__MED1__1__674__lociStitched | chr1 | 200292057 | 200306846 |
| 2__H2171__MED1__1__2203__lociStitched | chr13 | 71325559 | 71338429 |
| 2__H2171__MED1__1__3186__lociStitched | chr17 | 3729010 | 3741942 |
| 2__H2171__MED1__1__2909__lociStitched | chr16 | 11781980 | 11794751 |
| 2__H2171__MED1__1__4766__lociStitched | chr20 | 25613739 | 25620530 |
| 3__H2171__MED1__1__2897__lociStitched | chr16 | 11144367 | 11154452 |
| 1__H2171__MED1__1__5910__lociStitched | chr5 | 451422 | 454266 |
| 4__H2171__MED1__1__7415__lociStitched | chr8 | 63776687 | 63806155 |
| 1__H2171__MED1__1__1453__lociStitched | chr11 | 78328712 | 78331262 |
| 3__H2171__MED1__1__6678__lociStitched | chr6 | 112348676 | 112356273 |
| 2__H2171__MED1__1__1765__lociStitched | chr12 | 48546951 | 48555151 |
| 1__H2171__MED1__1__2433__lociStitched | chr14 | 76568042 | 76570777 |
| 1__H2171__MED1__1__7993__lociStitched | chr9 | 133904790 | 133908837 |
| 2__H2171__MED1__1__3164__lociStitched | chr17 | 1642357 | 1647888 |
| 4__H2171__MED1__1__1653__lociStitched | chr12 | 8501768 | 8523291 |
| 2__H2171__MED1__1__8030__lociStitched | chr9 | 138135585 | 138142078 |
| 4__H2171__MED1__1__6697__lociStitched | chr6 | 114858043 | 114874406 |
| 2__H2171__MED1__1__2731__lociStitched | chr15 | 67146253 | 67153108 |
| 1__H2171__MED1__1__676__lociStitched | chr1 | 200320223 | 200323463 |
| 3__H2171__MED1__1__7106__lociStitched | chr7 | 90891248 | 90904646 |
| 3__H2171__MED1__1__1282__lociStitched | chr11 | 31605924 | 31622763 |
| 1__H2171__MED1__1__6439__lociStitched | chr6 | 26304930 | 26308840 |
| 3__H2171__MED1__1__6542__lociStitched | chr6 | 43874271 | 43891627 |
| 2__H2171__MED1__1__362__lociStitched | chr1 | 61095855 | 61105484 |
| 3__H2171__MED1__1__4288__lociStitched | chr2 | 135067807 | 135078675 |
| 1__H2171__MED1__1__2649__lociStitched | chr15 | 44422399 | 44425293 |
| 4__H2171__MED1__1__1859__lociStitched | chr12 | 74259275 | 74282803 |
| 2__H2171__MED1__1__6347__lociStitched | chr6 | 15255876 | 15261598 |
| 3__H2171__MED1__1__3953__lociStitched | chr2 | 7321393 | 7328314 |
| 1__H2171__MED1__1__3540__lociStitched | chr17 | 77837805 | 77840024 |
| 2__H2171__MED1__1__6860__lociStitched | chr7 | 5429395 | 5446166 |
| 2__H2171__MED1__1__3999__lociStitched | chr2 | 23567475 | 23572888 |
| 1__H2171__MED1__1__5475__lociStitched | chr3 | 130776820 | 130781469 |
| 1__H2171__MED1__1__4528__lociStitched | chr2 | 207882381 | 207885158 |
| 2__H2171__MED1__1__842__lociStitched | chr1 | 232900985 | 232903673 |
| 2__H2171__MED1__1__3986__lociStitched | chr2 | 20412482 | 20420065 |
| 2__H2171__MED1__1__3326__lociStitched | chr17 | 43434796 | 43447830 |
| 3__H2171__MED1__1__5929__lociStitched | chr5 | 8720521 | 8737555 |
| 2__H2171__MED1__1__4569__lociStitched | chr2 | 218968606 | 218980938 |
| 3__H2171__MED1__1__890__lociStitched | chr10 | 1486532 | 1493897 |
| 1__H2171__MED1__1__7959__lociStitched | chr9 | 131260227 | 131263591 |
| 3__H2171__MED1__1__2166__lociStitched | chr13 | 58914764 | 58925684 |
| 1__H2171__MED1__1__8018__lociStitched | chr9 | 136926589 | 136930226 |
| 4__H2171__MED1__1__3837__lociStitched | chr19 | 40215562 | 40239946 |
| 2__H2171__MED1__1__6546__lociStitched | chr6 | 43906068 | 43912657 |
| 1__H2171__MED1__1__331__lociStitched | chr1 | 54796212 | 54799014 |
| 2__H2171__MED1__1__1637__lociStitched | chr12 | 3677173 | 3687680 |
| 2__H2171__MED1__1__4907__lociStitched | chr20 | 61600274 | 61610725 |
| 1__H2171__MED1__1__4771__lociStitched | chr20 | 29638614 | 29640239 |
| 1__H2171__MED1__1__6475__lociStitched | chr6 | 33043033 | 33048720 |
| 4__H2171__MED1__1__6405__lociStitched | chr6 | 21296380 | 21310734 |
| 2__H2171__MED1__1__5758__lociStitched | chr4 | 80183595 | 80191861 |
| 1__H2171__MED1__1__7556__lociStitched | chr8 | 126466494 | 126468843 |
| 2__H2171__MED1__1__4002__lociStitched | chr2 | 23606108 | 23613290 |
| 2__H2171__MED1__1__2058__lociStitched | chr12 | 123805217 | 123810213 |
| 2__H2171__MED1__1__849__lociStitched | chr1 | 233312827 | 233321459 |
| 3__H2171__MED1__1__3899__lociStitched | chr19 | 53527025 | 53546826 |
| 2__H2171__MED1__1__395__lociStitched | chr1 | 67912539 | 67916665 |
| 4__H2171__MED1__1__6138__lociStitched | chr5 | 134851883 | 134865995 |
| 2__H2171__MED1__1__4060__lociStitched | chr2 | 50612904 | 50617830 |
| 2__H2171__MED1__1__4365__lociStitched | chr2 | 155710278 | 155720040 |
| 2__H2171__MED1__1__7889__lociStitched | chr9 | 119201834 | 119207212 |
| 1__H2171__MED1__1__7587__lociStitched | chr8 | 134455564 | 134458775 |
| 3__H2171__MED1__1__2601__lociStitched | chr15 | 29458295 | 29478793 |
| 3__H2171__MED1__1__1260__lociStitched | chr11 | 22313265 | 22322600 |

TABLE 4-continued

SCLC Super-Enhancers Based on Gene Build hg 18

| REGION_ID | CHROM | START | STOP |
|---|---|---|---|
| 3_H2171_MED1_1_5218_lociStitched | chr3 | 10469904 | 10487109 |
| 3_H2171_MED1_1_6827_lociStitched | chr7 | 1204071 | 1217969 |
| 5_H2171_MED1_1_2046_lociStitched | chr12 | 123556670 | 123583312 |
| 2_H2171_MED1_1_193_lociStitched | chr1 | 27053645 | 27065430 |
| 2_H2171_MED1_1_4672_lociStitched | chr20 | 5798497 | 5808334 |
| 4_H2171_MED1_1_1335_lociStitched | chr11 | 45327480 | 45350583 |
| 2_H2171_MED1_1_3922_lociStitched | chr2 | 1989631 | 2000522 |
| 3_H2171_MED1_1_1783_lociStitched | chr12 | 51552711 | 51560557 |
| 1_H2171_MED1_1_4572_lociStitched | chr2 | 219568763 | 219574266 |
| 1_H2171_MED1_1_8038_lociStitched | chr9 | 138634973 | 138640138 |
| 2_H2171_MED1_1_450_lociStitched | chr1 | 107836814 | 107840728 |
| 1_H2171_MED1_1_6340_lociStitched | chr6 | 15092300 | 15095311 |
| 1_H2171_MED1_1_3904_lociStitched | chr19 | 53829063 | 53833837 |
| 5_H2171_MED1_1_5224_lociStitched | chr3 | 11299162 | 11324095 |
| 2_H2171_MED1_1_5986_lociStitched | chr5 | 35395346 | 35406891 |
| 3_H2171_MED1_1_1693_lociStitched | chr12 | 28296478 | 28309575 |
| 1_H2171_MED1_1_5922_lociStitched | chr5 | 3542098 | 3546382 |
| 3_H2171_MED1_1_2604_lociStitched | chr15 | 29544679 | 29560827 |
| 2_H2171_MED1_1_2254_lociStitched | chr13 | 99297247 | 99306503 |
| 4_H2171_MED1_1_2041_lociStitched | chr12 | 123445277 | 123474714 |
| 2_H2171_MED1_1_2141_lociStitched | chr13 | 52466506 | 52478601 |
| 6_H2171_MED1_1_817_lociStitched | chr1 | 230727775 | 230758255 |
| 3_H2171_MED1_1_2411_lociStitched | chr14 | 73925775 | 73939983 |
| 1_H2171_MED1_1_6346_lociStitched | chr6 | 15239481 | 15242062 |
| 2_H2171_MED1_1_31_lociStitched | chr1 | 6252175 | 6261523 |
| 2_H2171_MED1_1_6334_lociStitched | chr6 | 14651962 | 14658490 |
| 1_H2171_MED1_1_10_lociStitched | chr1 | 1355263 | 1360155 |
| 1_H2171_MED1_1_534_lociStitched | chr1 | 153237908 | 153244271 |
| 1_H2171_MED1_1_3988_lociStitched | chr2 | 20600392 | 20605649 |
| 1_H2171_MED1_1_5909_lociStitched | chr5 | 423764 | 428358 |
| 1_H2171_MED1_1_4170_lociStitched | chr2 | 86115761 | 86118411 |
| 1_H2171_MED1_1_7411_lociStitched | chr8 | 63579148 | 63586116 |
| 3_H2171_MED1_1_2624_lociStitched | chr15 | 37633152 | 37638629 |
| 1_H2171_MED1_1_5911_lociStitched | chr5 | 695232 | 697860 |
| 3_H2171_MED1_1_1253_lociStitched | chr11 | 19713467 | 19724753 |
| 3_H2171_MED1_1_2541_lociStitched | chr14 | 100247113 | 100254243 |
| 2_H2171_MED1_1_7301_lociStitched | chr7 | 157275487 | 157282112 |
| 1_H2171_MED1_1_5103_lociStitched | chr22 | 36214156 | 36218182 |
| 3_H2171_MED1_1_3372_lociStitched | chr17 | 53332524 | 53350328 |
| 2_H2171_MED1_1_2657_lociStitched | chr15 | 45586454 | 45593969 |
| 2_H2171_MED1_1_4694_lociStitched | chr20 | 12456692 | 12465019 |
| 2_H2171_MED1_1_6684_lociStitched | chr6 | 112571616 | 112582817 |
| 1_H2171_MED1_1_3996_lociStitched | chr2 | 22829298 | 22831811 |
| 2_H2171_MED1_1_8040_lociStitched | chr9 | 138704382 | 138711169 |
| 1_H2171_MED1_1_5920_lociStitched | chr5 | 3445869 | 3449196 |
| 1_H2171_MED1_1_5760_lociStitehed | chr4 | 80303607 | 80306058 |

What is claimed is:

1. A method of identifying a super-enhancer in a sample comprising chromatin, comprising: obtaining chromatin from a cell wherein said chromatin has been cross-linked such that chromosomal nucleic acid in the chromatin is cross-linked to a component selected from the group consisting of BRD4, a Mediator component and H3K27Ac with which the chromosomal nucleic acid is associated to form a cross-linked complex; contacting said cross-linked complex with a ligand having affinity for the component, said ligand selected from the group consisting of an antibody to BRD4, an antibody to a Mediator component, and an antibody to H3K27Ac, to form a complex between the cross-linked complex and the ligand;
  determining an amount of ligand bound to each enhancer in the cross-linked complex in the cell; and
  utilizing the determined amount of ligand bound to each enhancer to identify a super-enhancer,
  wherein the identified super-enhancer is bound to at least 10-fold more ligand than the median amount of ligand bound to enhancer within the cell.

2. The method of claim 1, wherein the component is BRD4 and the ligand is an antibody to BRD4.

3. The method of claim 1, wherein the component is a Mediator component and the ligand is an antibody to a Mediator component.

4. The method of claim 1, wherein the component is H3K27Ac and the ligand is an antibody to H3K27Ac.

5. The method of claim 1, comprising fragmenting the chromosomal nucleic acid of the cross-linked complex prior to the step of determining the amount of ligand bound.

6. The method of claim 5, comprising fragmenting the chromosomal nucleic acid after forming the complex between the cross-linked complex and the ligand.

7. The method of claim 1, wherein the cross-linking of the cross-linked complex comprises covalent cross-linking.

8. The method of claim 1, further comprising identifying a gene associated with said super-enhancer.

9. The method of claim 8, wherein said associated gene is identified by proximity to the super-enhancer.

10. The method of claim 8, wherein said associated gene is identified using high throughput chromatin conformation capture data.

11. The method of claim 8, wherein the gene associated with said super-enhancer is an endogenous gene within the cell.

12. The method of claim 1, wherein the component is endogenous to the cell.

13. The method of claim 1, wherein determining an amount of ligand bound to each enhancer in the cell is achieved by ChiP-Seq.

14. The method of claim 1, wherein at least a portion of the chromosomal nucleic acid is sequenced after contacting the cross-linked complex with the ligand.

15. The method of claim 1, wherein utilizing the determined amount of ligand bound to each enhancer to identify a super-enhancer comprises:
identifying a portion of the chromosomal nucleic acid that is bound to at least 10-fold more ligand than the median amount of ligand bound to enhancers within the cell.

16. The method of claim 1, wherein utilizing the determined amount of ligand bound to each enhancer to identify a super-enhancer comprises:
determining the median amount of ligand bound to enhancers within the cell;
identifying a portion of the chromosomal nucleic acid that is bound to at least 10-fold more ligand than the median as a super-enhancer.

17. A method of identifying a super-enhancer in a sample comprising chromatin, comprising:
obtaining chromatin from a cell wherein said chromatin has been cross-linked such that chromosomal nucleic acid in the chromatin is cross-linked to a component selected from the group consisting of BRD4, a Mediator component and H3K27Ac with which the chromosomal nucleic acid is associated to form a cross-linked complex;
contacting said cross-linked complex with a ligand having affinity for the component, said ligand selected from the group consisting of an antibody to BRD4, an antibody to a Mediator component, and an antibody to H3K27Ac, to form complex between the cross-linked complex and the ligand;
determining an amount of ligand bound to each enhancer in the cross-linked complex in the cell; and
utilizing the determined amount of ligand to each enhancer to identify a super-enhancer, wherein the identified super-enhancer has an amount of ligand bound that is above the point where the slope of the tangent is 1 in a rank-ordered graph of the amount of ligand bound to each of the enhancers in the cell.

18. The method of claim 17, wherein utilizing the determined amount of ligand bound to each enhancer to identify a super-enhancer comprises:
rank ordering the enhancers according to the amount of ligand bound;
identifying, with respect to the amount of ligand bound, the point where the slope of the tangent is 1 which would occur if said rank order were graphed; and
identifying any enhancer that falls above that point as a super-enhancer.

19. The method of claim 17, wherein utilizing the determined amount of ligand bound to each enhancer to identify a super-enhancer comprises:
graphing, in rank order of the amount of ligand bound, the enhancer and the amount of ligand bound to said enhancer;
identifying the point of the graph where the slope of the tangent is 1; and
identifying any enhancer that falls above that point as a super-enhancer.

20. The method of claim 17, wherein the component is BRD4 and the ligand is an antibody to BRD4.

21. The method of claim 17, wherein the component is a Mediator component and the ligand is an antibody to the Mediator component.

22. The method of claim 17, wherein the component is H3K27Ac and the ligand is an antibody to H3K27Ac.

23. The method of claim 17, comprising fragmenting the chromosomal nucleic acid of the cross-linked complex prior to the step of determining the amount of ligand bound.

24. The method of claim 23, comprising fragmenting the chromosomal nucleic acid after forming the complex between the cross-linked complex and the ligand.

25. The method of claim 17, wherein the cross-linking of the cross-linked complex comprises covalent cross-linking.

26. The method of claim 17, further comprising identifying a gene associated with said super-enhancer.

27. The method of claim 26, wherein said associated gene is identified by proximity to the super-enhancer.

28. The method of claim 17, wherein the component is endogenous to the cell.

29. The method of claim 17, wherein determining an amount of ligand bound to each enhancer in the cell is achieved by ChiP-Seq.

30. The method of claim 17, wherein at least a portion of the chromosomal nucleic acid is sequenced after contacting the cross-linked complex with the ligand.

* * * * *